(12) United States Patent
Ghaffari et al.

(10) Patent No.: US 9,545,285 B2
(45) Date of Patent: Jan. 17, 2017

(54) CARDIAC CATHETER EMPLOYING CONFORMAL ELECTRONICS FOR MAPPING

(71) Applicant: MC10, Inc., Cambridge, MA (US)

(72) Inventors: Roozbeh Ghaffari, Cambridge, MA (US); Stephen P. Lee, Cambridge, MA (US); Brian Elolampi, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 1020 days.

(21) Appl. No.: 13/646,613

(22) Filed: Oct. 5, 2012

(65) Prior Publication Data

US 2013/0274562 A1    Oct. 17, 2013

Related U.S. Application Data

(60) Provisional application No. 61/543,713, filed on Oct. 5, 2011, provisional application No. 61/543,748, filed on Oct. 5, 2011.

(51) Int. Cl.
*A61B 18/18* (2006.01)
*A61B 18/02* (2006.01)
(Continued)

(52) U.S. Cl.
CPC ........... *A61B 18/02* (2013.01); *A61B 5/02055* (2013.01); *A61B 5/02405* (2013.01); *A61B 5/036* (2013.01);
(Continued)

(58) Field of Classification Search
CPC ................... A61B 18/1492; A61B 2018/0022; A61B 2018/00267; A61B 2018/00654;A61B 2018/00011; A61B 2017/00243; A61B 2018/00351; A61B 8/445; A61B 18/02; A61B 2018/00744; A61B 5/6852; A61B 5/6853
See application file for complete search history.

(56) References Cited

U.S. PATENT DOCUMENTS 3,716,861 A    2/1973  Root
3,805,427 A    4/1974  Epstein
(Continued)

FOREIGN PATENT DOCUMENTS

WO    WO 2005/122285 A2    12/2005
WO    WO 2008/030960 A2    3/2008
(Continued)

OTHER PUBLICATIONS

Demura et al., "Immobilization of Glucose Oxidase with Bombyx Mori Silk Fibroin by Only Stretching Treatment and its Application to Glucose Sensor," Biotechnology and Bioengineering, vol. 33, 598-603 (6 pages) (1989).
(Continued)

*Primary Examiner* — Joseph Stoklosa
*Assistant Examiner* — Brian M Antiskay
(74) *Attorney, Agent, or Firm* — Nixon Peabody LLP

(57) ABSTRACT

An apparatus for medical diagnosis and/or treatment is provided. The apparatus includes a flexible substrate, an intermediate bus disposed on the flexible substrate, and a plurality of sensing elements disposed on the flexible substrate and coupled to the intermediate bus. The plurality of sensing elements and intermediate bus are disposed on the flexible substrate such that the sensing elements are disposed at areas of minimal strain of the flexible substrate.

51 Claims, 40 Drawing Sheets

(51) Int. Cl.

| | | |
|---|---|---|
| *A61B 5/00* | (2006.01) | |
| *A61B 5/042* | (2006.01) | |
| *A61B 5/046* | (2006.01) | |
| *A61B 18/14* | (2006.01) | |
| *A61B 5/024* | (2006.01) | |
| *A61B 5/03* | (2006.01) | |
| *A61B 5/044* | (2006.01) | |
| *A61B 5/145* | (2006.01) | |
| *A61B 5/0205* | (2006.01) | |
| *A61M 25/10* | (2013.01) | |
| *A61B 5/04* | (2006.01) | |
| *A61B 5/0215* | (2006.01) | |
| *A61B 5/053* | (2006.01) | |
| *A61N 7/00* | (2006.01) | |
| *A61B 18/20* | (2006.01) | |
| *A61B 18/00* | (2006.01) | |
| *A61B 5/01* | (2006.01) | |

(52) U.S. Cl.
CPC ........... *A61B 5/042* (2013.01); *A61B 5/044* (2013.01); *A61B 5/046* (2013.01); *A61B 5/0422* (2013.01); *A61B 5/14539* (2013.01); *A61B 5/14546* (2013.01); *A61B 5/4836* (2013.01); *A61B 5/6833* (2013.01); *A61B 5/6853* (2013.01); *A61B 18/1492* (2013.01); *A61M 25/10* (2013.01); *A61B 5/01* (2013.01); *A61B 5/0215* (2013.01); *A61B 5/053* (2013.01); *A61B 18/20* (2013.01); *A61B 2018/0016* (2013.01); *A61B 2018/0022* (2013.01); *A61B 2018/00357* (2013.01); *A61B 2018/00577* (2013.01); *A61B 2018/00648* (2013.01); *A61B 2018/00839* (2013.01); *A61B 2018/0212* (2013.01); *A61B 2018/0237* (2013.01); *A61B 2018/0262* (2013.01); *A61B 2562/0209* (2013.01); *A61B 2562/0247* (2013.01); *A61B 2562/125* (2013.01); *A61M 2025/105* (2013.01); *A61N 7/00* (2013.01); *Y10T 156/10* (2015.01)

(56) References Cited

U.S. PATENT DOCUMENTS

| | | |
|---|---|---|
| 5,817,008 A | 10/1998 | Rafert et al. |
| 5,907,477 A | 5/1999 | Tuttle et al. |
| 6,063,046 A | 5/2000 | Allum |
| 6,784,844 B1 | 8/2004 | Boakes et al. |
| 6,869,431 B2* | 3/2005 | Maguire ............... A61B 18/00 604/103 |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rodgers |
| 7,618,260 B2 | 11/2009 | Daniel et al. |
| 7,622,367 B1 | 11/2009 | Nuzzo |
| 7,759,167 B2 | 7/2010 | Vanfleteren |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rodgers |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,473,072 B2* | 6/2013 | Axelgaard ........... A61N 1/0452 600/372 |
| 8,536,667 B2 | 9/2013 | De Graff |
| 8,552,299 B2 | 10/2013 | Rodgers |
| 8,664,699 B2 | 3/2014 | Nuzzo |
| 8,679,888 B2 | 3/2014 | Rodgers |
| 8,729,524 B2 | 5/2014 | Rodgers |
| 8,754,396 B2 | 6/2014 | Rogers |
| 8,865,489 B2 | 10/2014 | Rodgers |
| 8,886,334 B2 | 11/2014 | Ghaffari |
| 8,905,772 B2 | 12/2014 | Rodgers |
| 9,012,784 B2 | 4/2015 | Arora |
| 2002/0094701 A1 | 7/2002 | Biegelsen et al. |
| 2002/0113739 A1 | 8/2002 | Howard |
| 2002/0145467 A1 | 10/2002 | Minch |
| 2003/0214408 A1 | 11/2003 | Grajales |
| 2004/0085469 A1 | 5/2004 | Johnson |
| 2004/0243204 A1 | 12/2004 | Maghribi |
| 2005/0096513 A1 | 5/2005 | Ozguz |
| 2005/0107716 A1 | 5/2005 | Eaton |
| 2006/0038182 A1 | 2/2006 | Rodgers |
| 2006/0264767 A1 | 11/2006 | Shennib |
| 2006/0286785 A1 | 12/2006 | Rogers |
| 2007/0123756 A1 | 5/2007 | Kitajima et al. |
| 2008/0046080 A1 | 2/2008 | Vanden Bulcke |
| 2008/0139894 A1 | 6/2008 | Szydlo-Moore et al. |
| 2008/0157235 A1 | 7/2008 | Rodgers |
| 2008/0204021 A1 | 8/2008 | Leussler et al. |
| 2008/0259576 A1 | 10/2008 | Johnson et al. |
| 2008/0312644 A1* | 12/2008 | Fourkas ............... A61B 18/02 606/22 |
| 2009/0000377 A1 | 1/2009 | Shipps et al. |
| 2009/0048556 A1 | 2/2009 | Durand |
| 2009/0107704 A1 | 4/2009 | Vanfleteren |
| 2009/0261828 A1 | 10/2009 | Nordmeyer-Massner |
| 2009/0294803 A1 | 12/2009 | Nuzzo |
| 2009/0322480 A1 | 12/2009 | Benedict et al. |
| 2010/0002402 A1 | 1/2010 | Rodgers |
| 2010/0059863 A1 | 3/2010 | Rogers |
| 2010/0072577 A1 | 3/2010 | Nuzzo |
| 2010/0087782 A1* | 4/2010 | Ghaffari ............. A61B 1/00082 604/103.01 |
| 2010/0090824 A1 | 4/2010 | Rowell et al. |
| 2010/0116526 A1 | 5/2010 | Arora |
| 2010/0178722 A1 | 7/2010 | De Graff |
| 2010/0245011 A1 | 9/2010 | Chatzopoulos et al. |
| 2010/0271191 A1 | 10/2010 | De Graff |
| 2010/0298895 A1 | 11/2010 | Ghaffari |
| 2010/0317132 A1 | 12/2010 | Rodgers |
| 2010/0321161 A1 | 12/2010 | Isabell |
| 2011/0034912 A1 | 2/2011 | De Graff et al. |
| 2011/0054583 A1 | 3/2011 | Litt |
| 2011/0101789 A1 | 5/2011 | Salter et al. |
| 2011/0121822 A1 | 5/2011 | Parsche |
| 2011/0140897 A1 | 6/2011 | Purks et al. |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0277813 A1 | 11/2011 | Rodgers |
| 2012/0016258 A1 | 1/2012 | Webster et al. |
| 2012/0051005 A1 | 3/2012 | Vanfleteren |
| 2012/0052268 A1 | 3/2012 | Axisa |
| 2012/0065937 A1 | 3/2012 | De Graff |
| 2012/0087216 A1 | 4/2012 | Keung et al. |
| 2012/0092178 A1 | 4/2012 | Callsen |
| 2012/0092222 A1 | 4/2012 | Kato et al. |
| 2012/0157804 A1 | 6/2012 | Rodgers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman et al. |
| 2012/0327608 A1 | 12/2012 | Rodgers |
| 2013/0041235 A1 | 2/2013 | Rogers et al. |
| 2013/0099358 A1 | 4/2013 | Elolampi |
| 2013/0100618 A1 | 4/2013 | Rogers |
| 2013/0118255 A1 | 5/2013 | Callsen |

(56) References Cited

U.S. PATENT DOCUMENTS

| | | |
|---|---|---|
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma et al. |
| 2013/0225965 A1 | 8/2013 | Ghaffari |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville et al. |
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora et al. |
| 2015/0099976 A1 | 4/2015 | Ghaffari et al. |
| 2015/0100135 A1 | 4/2015 | Ives |

FOREIGN PATENT DOCUMENTS

| | | |
|---|---|---|
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |

OTHER PUBLICATIONS

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

U.S. Appl. No. 12/921,808, filed Mar. 12, 2009, B. Litt, Flexible and Scalable Sensor Arrays for Recording and Modulating Physiologic Activity.

U.S. Appl. No. 12/968,637, filed Dec. 15, 2010, J. Rodgers, High-Speed, High-Resolution Electrophysiology In-Vivo Using Conformal Electronics.

U.S. Appl. No. 13/492,636, filed Jun. 8, 2012, J. Rodgers, Flexible and Stretchable Electronic Systems for Epidermal Electronics.

U.S. Appl. No. 14/155,010, filed Jan. 14, 2014, R. Nuzzo, Methods and Devices for Fabricating and Assembling Printable Semiconductor Elements.

U.S. Appl. No. 14/173,525, filed Feb. 5, 2014, J. Rodgers, Arrays of Ultrathin Silicon Solar Microcells.

U.S. Appl. No. 14/220,910, filed Mar. 20, 2014, J. Rodgers, Controlled Buckling Structures in Semiconductor Interconnnects and Nanomembranes for Stretchable Electronics.

U.S. Appl. No. 14/220,923, filed Mar. 20, 2014, J. Rodgers, Stretchable Form of Single Crystal Silicon for High Performance Electronics on Rubber Substrates.

U.S. Appl. No. 14/479,100, filed Sep. 5, 2014, J. Rodgers, Printed Assemblies of Ultrathin, Microscale Inorganic Light Emitting Diodes for Deformable and Semitransparent Displays.

U.S. Appl. No. 14/521,319, filed Oct. 22, 2014, J. Rodgers, Stretchable and Foldable Electronic Devices.

International Search Report for PCT/US12/59131, dated Apr. 8, 2013, 6 pages.

U.S. Appl. No. 12/575,008, filed Oct. 7, 2009, R. Ghaffari et al., Catheter Balloon Having Stretchable Circuitry and Sensor Array.

U.S. Appl. No. 12/972,073, filed Dec. 17, 2010, G. Callsen et al., Methods and Apparatus for Conformal Sensing of Force and/or Acceleration At a Person's Head.

U.S. Appl. No. 12/976,607, filed Dec. 22, 2010, G. Callsen et al., Methods and Apparatus for Conformal Sensing of Change in Motion At an Arbitrarily-Shaped Surface.

(56) References Cited

OTHER PUBLICATIONS

U.S. Appl. No. 12/976,814, filed Dec. 22, 2010, G. Callsen et al., Methods and Apparatus Having Power Control Features for Conformal Sensing of Change in Motion of a Body Part.
U.S. Appl. No. 12/976,833, filed Dec. 22, 2010, G. Callsen et al., Methods and Apparatus for Assessing Head Trauma Based on Conformal Sensing of Force and/or Change in Motion of a Person's Head.
U.S. Appl. No. 13/082,388, filed Apr. 7, 2011, B. De Graff et al., Methods and Apparatus for Measuring Technical Parameters of Equipment, Tools and Components Via Conformal Electronics.
U.S. Appl. No. 14/004,408, filed Mar. 9, 2012, R. Ghaffari et al., Integrated Devices to Facilitate Quantitative Assays and Diagnostics.
U.S. Appl. No. 13/481,843, filed May 27, 2012, B. Elolampi et al., Electronic, Optical and/or Mechanical Apparatus and Systems and Methods for Fabricating Same.
U.S. Appl. No. 13/499,626, filed Jun. 12, 2012, R. Ghaffari et al., Protective Cases With Integrated Electronics.
U.S. Appl. No. 13/550,254, filed Jul. 16, 2012, J. Carbeck et al., Detection of a Force on a Foot or Footwear.
U.S. Appl. No. 13/568,022, filed Aug. 6, 2012, R. D'angelo et al., Catheter Balloon Methods and Apparatus Employing Sensing Elements.
U.S. Appl. No. 13/603,290, filed Sep. 4, 2012, C. Rafferty et al., Electronics for Detection of a Condition of Tissue.
U.S. Appl. No. 13/631,739, filed Sep. 28, 2012, C. Rafferty et al., Electronics for Detection of a Property of a Surface.
U.S. Appl. No. 13/646,613, filed Oct. 5, 2012, R. Ghaffari et al., Cardiac Catheter Employing Conformal Electronics for Mapping.
U.S. Appl. No. 13/747,826, filed Jan. 23, 2013, B. De Graff et al., Methods and Applications of Non-Planar Imaging Arrays.
U.S. Appl. No. 13/640,280, filed Feb. 25, 2013, B. De Graff et al., Methods and Apparatus for Measuring Technical Parameters of Equipment, Tools and Components Via Conformal Electronics.
U.S. Appl. No. 13/843,873, filed Mar. 15, 2013, Y. Hsu, Strain Isolation Structures for Stretchable Electronics.
U.S. Appl. No. 13/843,880, filed Mar. 15, 2013, Y. Hsu, Strain Relief Structures for Stretchable Interconnects.
U.S. Appl. No. 13/844,399, filed Mar. 15, 2013, S. Fastert et al., Conformal Electronics Integrated With Apparel.
U.S. Appl. No. 13/844,508, filed Mar. 15, 2013, S. Fastert et al., Monitoring Hit Count for Impact Events.
U.S. Appl. No. 13/844,635, filed Mar. 15, 2013, R. Ghaffari et al., Catheter Balloon Having Stretchable Integrated Circuitry and Sensor Array.
U.S. Appl. No. 13/844,638, filed Mar. 15, 2013, C. Rafferty et al., Embedding Thin Chips in Polymer.
U.S. Appl. No. 13/844,677, filed Mar. 15, 2013, S. Lee et al., Catheter Device Including Flow Sensing.
U.S. Appl. No. 13/844,767, filed Mar. 15, 2013, R. Ghaffari et al., Catheter Balloon Employing Force Sensing Elements.
U.S. Appl. No. 13/963,778, filed Aug. 9, 2013, B. De Graff et al., Systems, Methods and Devices Having Stretchable Integrated Circuitry for Sensing and Delivering Therapy.
U.S. Appl. No. 14/093,329, filed Nov. 29, 2013, R. Ghaffari, Systems, Methods, and Devices Having Stretchable Integrated Circuitry for Sensing and Delivering Therapy.
U.S. Appl. No. 14/147,347, filed Jan. 3, 2014, R. Ghaffari et al., Catheter or Guidewire Device Including Flow Sensing and Use Thereof.
U.S. Appl. No. 14/276,413, filed May 13, 2014, Y. Hsu et al., Conformal Electronics Including Nested Serpentine Interconnects.
U.S. Appl. No. 14/294,808, filed Jun. 3, 2014, I Kacyvenski et al., Motion Sensor and Analysis.
U.S. Appl. No. 14/311,686, filed Jun. 23, 2014, J. Fenuccio et al., Band With Conformable Electronics.
U.S. Appl. No. 14/451,981, filed Aug. 5, 2014, X. Li et al., Flexible Temperature Sensor Including Conformable Electronics.
U.S. Appl. No. 14/488,544, filed Sep. 17, 2014, W. Arora et al., Extremely Stretchable Electronics.
U.S. Appl. No. 14/510,868, filed Oct. 9, 2014, B. Ives, Utility Gear Including Conformal Sensors.
U.S. Appl. No. 29/506,439, filed Oct. 15, 2014, X. Li et al., Electronic Device Having Antenna.
U.S. Appl. No. 14/518,856, filed Oct. 20, 2014, R. Ghaffari et al., Systems, Methods, and Devices Using Stretchable or Flexible Electronics for Medical Applications.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.
U.S. Appl. No. 14/630,335, filed Feb. 24, 2015, B. Keen, Conformal Electronics with Deformation Indicators.
U.S. Appl. No. 14/656,046, filed Mar. 12, 2015, R. Ghaffari et al., Quantification of a Change in Assay.

\* cited by examiner

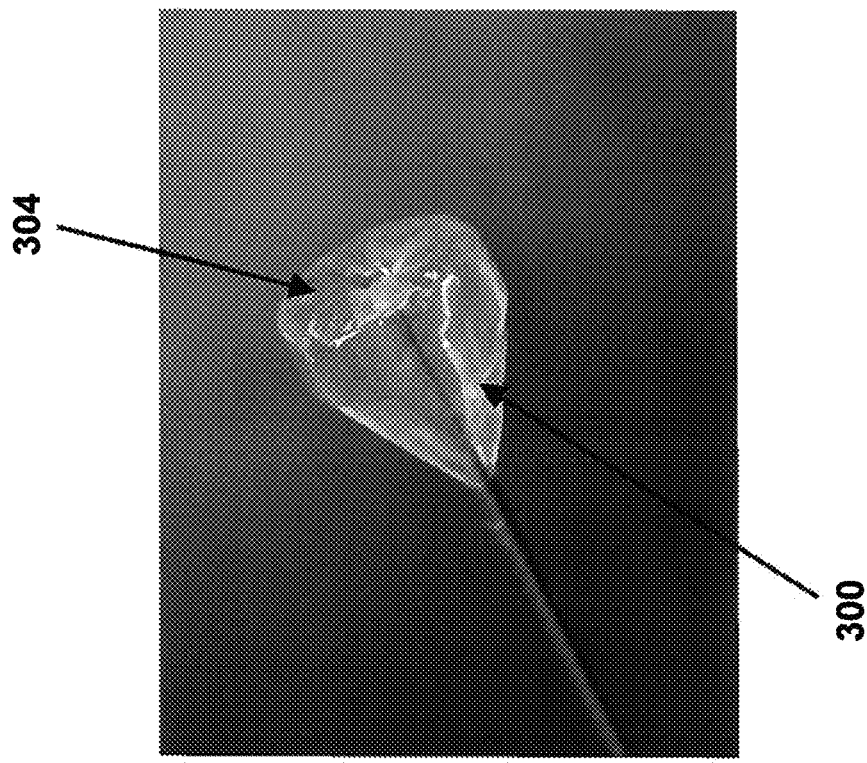
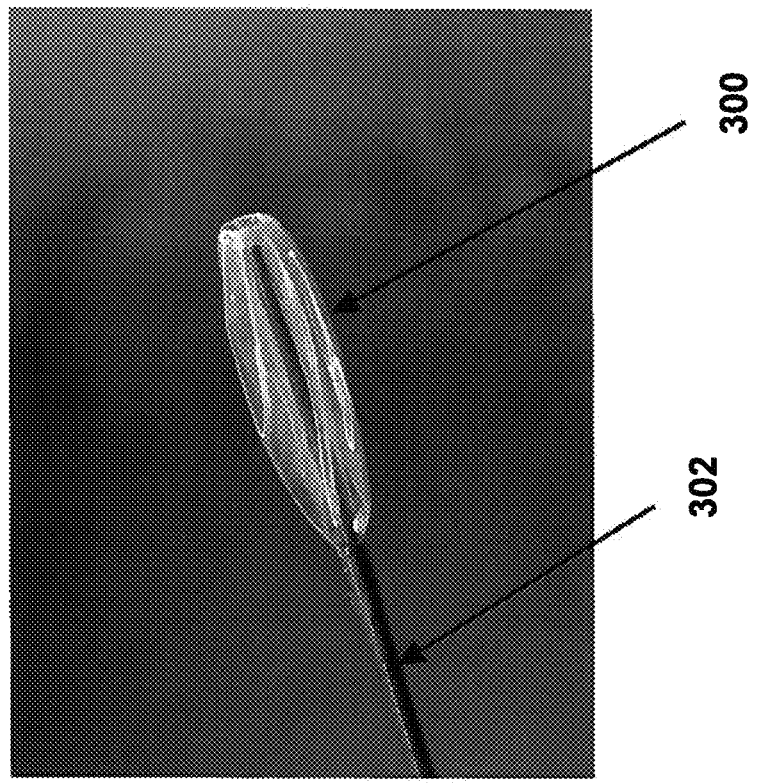

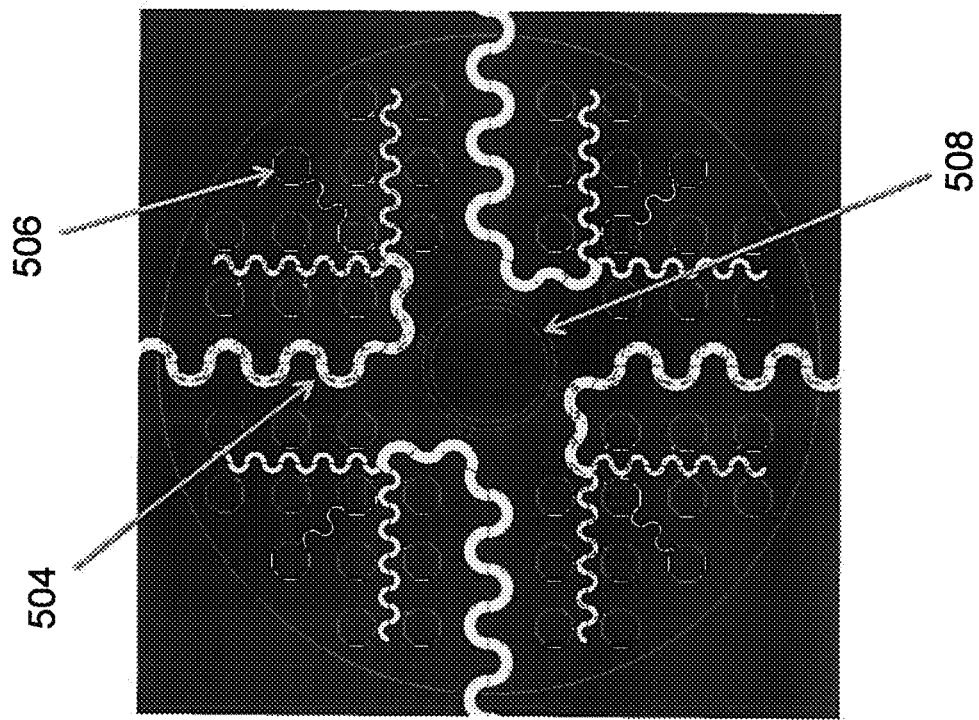
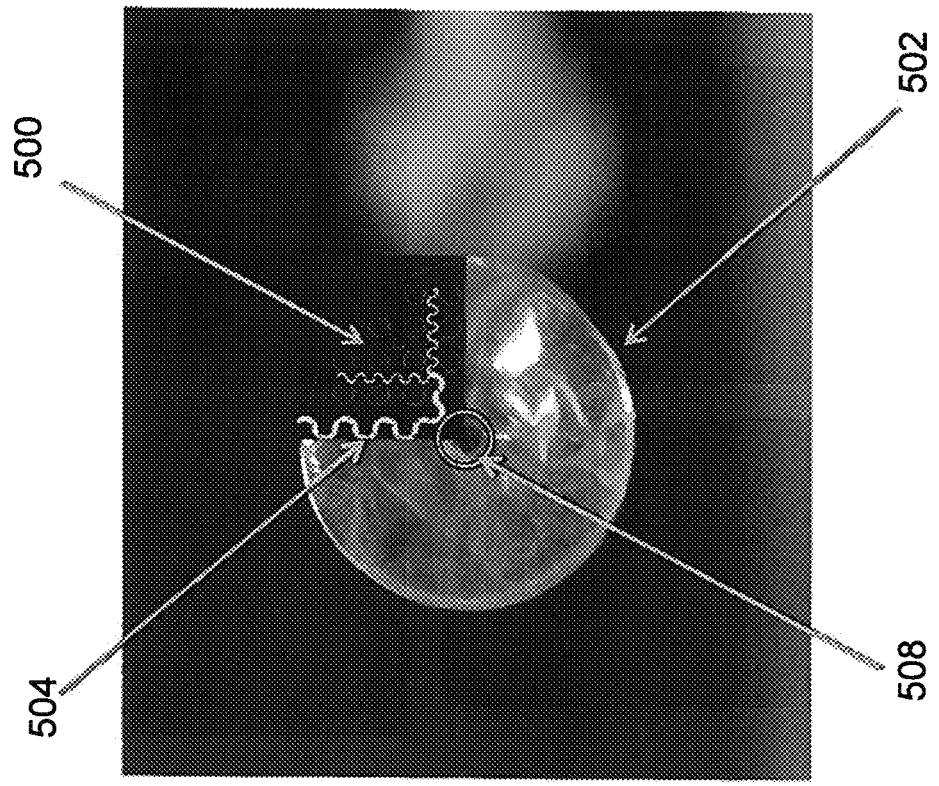
Fig. 5B
Fig. 5A

CARDIAC CATHETER EMPLOYING CONFORMAL ELECTRONICS FOR MAPPING

CROSS-REFERENCES TO RELATED APPLICATIONS

This application claims priority to U.S. provisional application Ser. No. 61/543,713, filed Oct. 5, 2011, entitled "CARDIAC CATHETER METHODS AND APPARATUS AND SYSTEMS EMPLOYING CONFORMAL ELECTRONICS FOR CARDIAC MAPPING," and U.S. provisional application Ser. No. 61/543,748, filed Oct. 5, 2011, entitled "CONFORMAL ELECTRONICS EMPLOYING ELECTRODE ARRAYS," each of which is hereby incorporated herein by reference in its entirety.

BACKGROUND

Existing sensing and therapeutic devices can have limited applicability due to a lack of sophistication related to the sensing, imaging, and therapeutic functions. The precision and speed of sensing, imaging and therapeutic functions is beneficial for treating certain cardiac diseases, such as atrial fibrillation.

According to some research, atrial fibrillation (AF) affects 5 million patients in the developed world and is the leading cause of stroke in cardiac patients. With up to 400,000 new cases diagnosed yearly, the adverse outcomes of various types of AF range from congestive heart failures to sudden death. Catheter ablation techniques have become increasingly prevalent as interventional strategies for treating various forms of cardiac arrhythmia, including AF, ventricular fibrillation (VF), and ventricular tachycardia (VT). Some catheter ablation techniques generate linear lesions in a "point-by-point" fashion with radio frequency (RF) electrodes; however, such techniques have not had an effective success rate in patients with persistent AF, at least in part because the ablation targets are not well defined because the techniques are generally lengthy procedure requiring highly skilled operators to minimize risk of stroke and other clinical complications. Current ablation targets in persistent AF include areas exhibiting "complex fractionated atrial electrograms" (CFAEs). These are electrical recordings with a highly disorganized appearance. It is believed that CFAEs represent rapid electrical activity from a nearby driving force (rotor).

Studies on isolated hearts using high resolution optical mapping have revealed the presence of rotors (re-entrant circuits) as an underlying mechanism for AF. It is believed that high-frequency impulses emanating from the rotors are subject to spatially distributed intermittent blockade imposed by the presence of functional and anatomical obstacles in their path, resulting in the seemingly disorganized activity that characterizes AF. Thus far, the demonstration of rotors in the clinical setting has been limited by the lack of high resolution voltage mapping. As a result, treatment strategies, such as catheter ablation, remain marginally effective in persistent AF cases because of the inability to define clear targets.

SUMMARY

The Inventors have recognized and appreciated that inflatable bodies that include sensing elements can provide data measurements that could beneficial medical diagnosis and/ or treatment. The inventors have also recognized that such systems can be made more robust to the use in medical diagnosis and/or treatment environment, provide useful measurements of tissue states (including amount of contact with the tissue), and maintain optimal performance, if the sensing elements are selectively disposed at certain regions of a flexible substrate. In view of the foregoing, various examples herein are directed generally to methods, apparatus and systems for medical diagnosis and/or treatment that include a flexible substrate and a plurality of sensing elements disposed on the flexible substrate, where the sensing elements are selectively disposed at certain regions of the flexible substrate. A distributed arrangement of electrical circuitry for read-out of signals from such sensing elements are also provided.

The present disclosure provides some examples of an apparatus for medical diagnosis and/or treatment that include a flexible substrate, an intermediate bus disposed on the substrate, and a plurality of sensing elements disposed on the flexible substrate. The plurality of sensing elements are coupled to the intermediate bus. The plurality of sensing elements and the intermediate bus are disposed on the flexible substrate such that the sensor elements are disposed at areas of minimal curvature and/or flexing of the flexible substrate.

In some examples herein, an apparatus is provided for medical diagnosis and/or treatment that includes a flexible substrate forming an inflatable body and a plurality of sensing elements disposed on the flexible substrate. The plurality of sensing elements is disposed about a distal region of the inflatable body such that the sensing elements are disposed at areas of minimal curvature of the inflatable body in a deflated state.

An example apparatus is provided for medical diagnosis and/or treatment, according to the principles described herein. The apparatus includes a flexible substrate, at least one intermediate bus disposed on the flexible substrate, and a plurality of sensing elements disposed in a close-packed array proximate to an end of the at least one intermediate bus. Each sensing element of the plurality of sensing elements is coupled to the at least one intermediate bus.

In various examples, the sensing elements can be disposed at areas of minimal bending and/or flexing of the flexible substrate.

In an example, the flexible substrate can be an adhesive patch or a bandage.

In an example, a measurement of the plurality of sensing elements can be used to provides a measure of an amount of contact between the inflatable body and a surface.

The surface can be a portion of a tissue. In an example, a measurement from the plurality of sensing elements provides an indication of an arrhythmia condition of the tissue. In another example, a measurement from the plurality of sensing elements provides an indication of an artial fibrillation or a ventricular fibrillation of the tissue.

The flexible substrate can form an inflatable body, where a portion of the at least one intermediate bus is disposed about a distal region of the inflatable body.

The inflatable body can be a disposed on a catheter, where a measurement of the plurality of sensing elements provides a measure of an amount of contact between the inflatable body and a tissue. In an example, the measurement of the plurality of sensing elements can be used to provide a mapping of the tissue. In another example, the measurement of the plurality of sensing elements can be used to provide a spatial mapping and/or a temporal mapping of an arrhythmia.

In another example according to the principles described herein, an apparatus is provided for medical diagnosis and/or treatment, the apparatus including a flexible substrate forming an inflatable body, at least one intermediate bus, and a plurality of sensing elements disposed on the flexible substrate proximate to the distal region of the inflatable body in an array. A portion of the at least one intermediate bus is disposed about a distal region of the inflatable body. At least one sensing element of the plurality of sensing elements is coupled to the at least one intermediate bus.

In an example, the at least one intermediate bus is electrically conductive. In some examples, portions of the at least one intermediate bus can be formed from a non-conductive material.

The apparatus can include at least one coupling structure disposed about a distal region of the inflatable body. A portion of the at least one intermediate bus can be coupled to a portion of the at least one coupling bus.

In an example, the coupling structure can be a non-conductive structure.

In an example, the plurality of sensing elements can be disposed in an array at an area of minimal curvature of the inflatable body proximate to the distal region of the inflatable body.

Each of the at least one intermediate bus may electronically connect each sensing element of the plurality of sensing elements with an electrical source.

The plurality of sensing elements can be disposed in an array in a quadrant of the distal region of the inflatable body.

In an example, the intermediate bus can be a collection of serpentine buses, where the serpentine buses electrically couple to the plurality of sensing elements.

The apparatus can also include an encapsulation material disposed over substantially a portion of the intermediate bus and/or the plurality of sensing elements.

In an example, the encapsulation layer positions the sensing elements at a neutral mechanical plane of the apparatus.

The encapsulation material can include a polyurethane.

In an example, the at least one intermediate bus comprises a first intermediate bus and a second intermediate bus. The first intermediate bus couples to sensing elements of the plurality of sensing elements disposed in a first quadrant of the distal region of the inflatable body. The second intermediate bus couples to sensing elements of the plurality of sensing elements disposed in a second quadrant of the distal region of the inflatable body. The first quadrant can be disposed opposite to the second quadrant. In another example, the apparatus also can include a third intermediate bus and a fourth intermediate bus. The third intermediate bus can couple to sensing elements of the plurality of sensing elements disposed in a third quadrant of the distal region of the inflatable body. The fourth intermediate bus can couple to sensing elements of the plurality of sensing elements disposed in a fourth quadrant of the distal region of the inflatable body. The third quadrant can be disposed opposite to the fourth quadrant, where the third quadrant is oriented at substantially a 90° angle relative to the first quadrant.

The inflatable body can be disposed about a shaft, where the shaft includes a cryoablation device, a laser ablation device, a high intensity ultrasound, and/or a RF device.

The plurality of sensing elements can include at least one of a pressure sensor and/or at least one impedance sensor.

One or more of the sensing elements of the plurality of sensing elements can include contact sensors.

The inflatable body can be a balloon. In different examples, the balloon can be cylindrical, onion-shaped, cone-shaped, dog-bone-shaped, or barrel-shaped.

The sensing elements can be formed from a conductive material.

In an example according to the principles herein, a method of fabricating an apparatus for medical diagnosis and/or treatment is provided. The method can include providing an electronic structure that includes a first intermediate bus and a plurality of sensing elements. A first sensing element of the plurality of sensing elements can be coupled to the first intermediate bus. The method includes disposing a portion of the first intermediate bus at a first distal region of an inflatable body, and disposing the first sensing element of the plurality of sensing elements about a portion of the inflatable body proximate to the first distal region.

In an example, the plurality of sensing elements can be disposed about the portion of the inflatable body proximate to the distal region such that the sensor elements are disposed at areas of minimal curvature of the inflatable body.

The method further can include extracting the electronic structure from a carrier substrate prior to disposing the electronic structure about the inflatable body.

The disposing the electronic structure about the inflatable body can include applying the first intermediate bus and/or the plurality of sensing elements using a dissolvable tape.

The electronic structure further can include a coupling structure, where the first intermediate bus is coupled to a portion of the coupling structure, and where the disposing the electronic structure about the inflatable body comprises disposing the coupling structure about the inflatable body and aligning the plurality of sensing elements at the distal region of the inflatable body.

The electronic structure can be fabricated using a CMOS process.

In an example, the electronic structure further can include a second intermediate bus, where a second sensing element of the plurality of sensing elements is coupled to the second intermediate bus.

The method further can include disposing a portion of the second intermediate bus at a second distal region of the inflatable body different from the first region and disposing the second sensing element of the plurality of sensing elements about a portion of the inflatable body proximate to the second distal region.

The method can further include coupling the first intermediate bus and the second intermediate bus to a signal processor, where the electronic structure is configured to transmit one or more multiplexed signals to the at least one signal processor via the first intermediate bus and the second intermediate bus.

In another example according to the principles described herein, a method of performing a medical diagnosis and/or treatment on a tissue is provided. The method includes disposing in proximity to the tissue an apparatus that includes a flexible substrate forming an inflatable body, at least one intermediate bus, where a portion of the at least one intermediate bus is disposed at a distal region of the inflatable body, and a plurality of sensing elements disposed on the flexible substrate proximate to the distal region of the inflatable body. At least one sensing element of the plurality of sensing elements is coupled to the at least one intermediate bus. The method further includes recording a measurement of at least one sensing element of the plurality of sensing elements, where the measurement provides an indication of a state of a portion of the tissue.

In an example, the measurement can provide an indication of a disease state of the portion of the tissue. In another example, the measurement can provide an indication of a contact state of the portion of the tissue with the at least one sensing element of the plurality of sensing elements. The plurality of sensing elements can be disposed in an array at areas of minimal curvature of the inflatable body proximate to the distal region of the inflatable body.

In another example according to the principles described herein, a system for mapping contact with a surface is described. The system includes an inflatable body having a distal portion, a plurality of sensing elements disposed on the inflatable body proximate to the distal portion, at least one intermediate bus, and an electronic display electrically coupled to the plurality of sensing elements. The at least one sensing element of the plurality of sensing elements can be coupled to the at least one intermediate bus. The electronic display can provide a visual representation of the spatial orientation of the plurality of sensing elements on the inflatable body, and changing a visual attribute of an electrode in the plurality of sensing elements in response to a change in an electrical signal produced by the electrode. The change in the electrical signal can be used to identify a contact condition of the electrode with respect to the surface.

The visual attribute can be a binary representation or a quantitative representation.

The present disclosure also provides examples of a stretchable electronic system that include a flexible interconnect and a plurality of impedance based electrode pairs coupled to the flexible interconnect. The electrode pairs measure impedance between two electrodes of the electrode pair.

In accordance with examples disclosed herein, co-locating contact sensors (electrical, pressure, thermal or otherwise) with the therapeutic facility (which may comprise any circuitry and elements to delivery ablation described herein) can reduce or eliminate the need for dyes and may reduce the time to complete the procedure. Further, example systems and apparatus disclosed herein can be implemented to both deliver the ablative therapy and the same device during the same procedure can be implemented to generate data regarding of the electrical conductivity of the site post-ablation.

Various examples according to the principles described herein include an apparatus having a flexible substrate and a plurality of active electrical circuits coupled to the flexible substrate. The active electrical circuits in the plurality of active electrical circuits may be coupled to at least one adjacent active electrical circuit in the plurality of active electrical circuits via at least one conductive flexible interconnection. The plurality of active electrical circuits may be configured to transmit one or more multiplexed signals to at least one signal processor.

One or more of the active electrical circuits in the plurality of active electrical circuits may include at least one electrode. One or more of the active electrical circuits in the plurality of active electrical circuits may include at least one multiplexing transistor. One or more of the active electrical circuits in the plurality of active electrical circuits may include at least one amplifier. One or more of the active electrical circuits in the plurality of active electrical circuits may include at least one current mirror and the mirror may be switchable between an off state and an on state.

One or more of the active electrical circuits in the plurality of active electrical circuits may include at least one current limiting resistor.

One or more of the active electrical circuits in the plurality of active electrical circuits may include a differential pair of transistors coupled to third transistor configured as a current mirror switchable from an on state to an off state. The one or more active circuit may further include a resistor coupled to the third transistor configured to collapse the differential pair when the third transistor is in an on state.

In various examples the plurality of active electrical circuits are positioned in a plurality of arrays on the flexible substrate.

In some examples the at least one signal processor is configured to receive a multiplexed signal from each active circuit In some examples the substrate may be stretchable and in some examples the substrate may be elastic.

The conductive flexible interconnection may be buckled in some examples and may have a serpentine geometric configuration in some examples.

The active electrical circuits may include one or more components selected from the group consisting of: a transistor, a resistor, a capacitor, an inductor, and a diode.

In some examples at least one circuit in the plurality of active electrical circuits may include at least one of, temperature sensor, a pressure sensor, a contact sensor, a conductivity sensor, a strain gauge, a complementary metal-oxide-semiconductor, metal oxide semiconductor field effect transistor, a light emitting diode, an electrode, a pH sensor, a chemical sensor, a biological sensor, and a calcium sensor.

In some examples the processor may be configured to construct a map of at least one physiological parameter by associating a portion of the multiplexed signal with one or more originating active electrical circuits in the plurality of active electrical circuits.

The apparatus may have an active electrical circuit density of at least 64 circuits per $cm^2$ in some examples. The apparatus of may have an active electrical circuit density ranging from 200 to 500 circuits per $cm^2$ in some examples.

In an example according to the principles herein, the present disclosure provide an apparatus for readout of one or more multiplexed signals. The apparatus includes a flexible substrate, and a plurality of active electrical circuits disposed on the substrate in a distributed arrangement, the plurality of active electrical circuits being configured to transmit one or more multiplexed signals to at least one signal processor. At least one active electrical circuit of the plurality of active electrical circuits includes at least one electrode, and at least one differential pair amplifier coupled to the at least one electrode. The plurality of active electrical circuits are disposed in a distributed arrangement on the substrate such that the apparatus is conformable to a contour of a surface to be measured.

The flexible substrate can be a portion of an inflatable body, where the plurality of active electrical circuits are disposed at areas of minimal curvature of the inflatable body in the distributed arrangement.

Each active electrical circuit of the plurality of active electrical circuits can be coupled to at least one adjacent active electrical circuit of the plurality of active electrical circuits via at least one conductive flexible interconnection.

The apparatus can further include at least one conductive intermediate bus, where the at least one active electrical circuit of the plurality of active electrical is coupled to the at least one conductive intermediate bus.

The plurality of active electrical circuits can be configured to transmit one or more multiplexed signals to the at least one signal processor via the at least one conductive intermediate bus.

The at least one active electrical circuit of the plurality of active electrical circuits can further include a tail, where the at least one differential pair amplifier is coupled to the tail.

In an example, each of the active electrical circuit of the plurality of active electrical circuits can include at least one electrode and at least one differential pair amplifier coupled to the at least one electrode. Each of the at least one differential pair amplifier can include a pair of transistors whose sources are connected in a common connection to provide a common source. The pair of transistors can be PMOS transistors. Each of the transistors can be connected in series with a current limiting resistor.

In an example, each of the at least one differential pair amplifier can be coupled to a tail. The tail can be a transistor, where the common source of the at least one differential pair amplifier is coupled to a drain of the tail. The gate of the tail can be driven by a current-mirror.

In an example, at least one electrode can be coupled to a gate of a transistor of the pair of transistors.

In an example, the plurality of active electrical circuits can be read in a row-column arrangement, where each row-column element of the row-column arrangement corresponds to at least one active electrical circuit of the plurality of active electrical circuits, and where a drain of a first transistor of the pair of transistors of each respective active electrical circuit is coupled to a column output of each respective row-column element. A second transistor of the pair of transistors of each respective active electrical circuit can be coupled to a load resistor. All columns of the row-column arrangement can be read substantially simultaneously, where a single row of the row-column arrangement is active when the columns of the row-column arrangement are read. The drain of the first transistor of the pair of transistors of at least two active electrical circuits can be coupled to the column output of each respective row-column element.

In an example, each of the at least one differential pair amplifier of each active electrical circuit is coupled to a tail, where each row input of the row-column arrangement is coupled to a gate of a tail of each active electrical circuit of the plurality of active electrical circuits. Each row input of the row-column arrangement can be coupled to a gate of a tail of each active electrical circuit of the plurality of active electrical circuits.

In an example, the at least one active electrical circuit of the plurality of active electrical circuits can include two electrodes, and a differential pair amplifier, where the two electrodes are coupled to the differential pair amplifier. The differential pair amplifier can include a pair of transistors whose sources are connected in a common connection to provide a common source. Each electrode can be coupled to a gate of each transistor of the pair of transistors. A read-out of the at least one active electrical circuit can be based on a differential of signals from the two electrodes.

In another example, the present disclosure also provides a method for readout of one or more multiplexed signals. The method includes disposing an apparatus proximate to a surface. The apparatus includes a plurality of active electrical circuits disposed on a flexible substrate in a distributed arrangement, the plurality of active electrical circuits being configured to transmit one or more multiplexed signals to at least one signal processor. At least one active electrical circuit of the plurality of active electrical circuits includes an electrode, a differential pair amplifier coupled to the electrode, and a tail coupled to the differential pair amplifier, where the tail is coupled to a row control switch, where the differential pair amplifier is coupled to a column output, and where activating the row control switch activates the differential pair amplifier such that a signal from the electrode is transmitted to the column output. The method can further include applying a voltage to the row control switch and reading an output at the column output thereby providing the one or more multiplexed signals.

The plurality of active electrical circuits can be coupled to a flexible substrate forming an inflatable body. Each active electrical circuit of the plurality of active electrical circuits is coupled to at least one adjacent active electrical circuit of the plurality of active electrical circuits via at least one conductive flexible interconnection.

In an example, the method can further include transmitting the one or more multiplexed signals from the plurality of active electrical circuits to the at least one signal processor via the at least one conductive flexible interconnection.

The apparatus can further include at least one conductive intermediate bus, where the at least one active electrical circuit of the plurality of active electrical is coupled to the at least one conductive intermediate bus.

In an example, the method can further include transmitting the one or more multiplexed signals from the plurality of active electrical circuits to the at least one signal processor via the at least one conductive intermediate bus.

The electrode can be coupled to a first gate of the differential pair amplifier.

The apparatus can further include a second electrode, where a second gate of the differential pair amplifier is coupled to the second electrode.

The apparatus can further include a second electrode, where a second gate of the differential pair amplifier is biased to a ground potential.

The tail can be coupled to the row control switch via a current-mirror, where activating the row control switch biases the current-mirror, thereby activating the differential pair amplifier.

The at least one active electrical circuits can include two active electrical circuits, where each of the two active electrical circuits is coupled to a respective row control switch, where the two active electrical circuits are coupled to a common column output, and where one of the row control switches is activated during the reading of the output from the common column output.

In another example, the present disclosure provides an apparatus for readout of one or more multiplexed signals. The apparatus includes a flexible substrate forming an inflatable body and a plurality of active electrical circuits disposed on the flexible substrate, the plurality of active electrical circuits being configured to transmit one or more multiplexed signals to at least one signal processor. The at least one active electrical circuit of the plurality of active electrical circuits includes at least one electrode and at least one source-follower amplifier coupled to the at least one electrode. The plurality of active electrical circuits are disposed in a distributed arrangement on the substrate such that the apparatus is conformable to a contour of a surface to be measured.

The plurality of active electrical circuits can be disposed at areas of minimal curvature of the inflatable body in the distributed arrangement.

Each active electrical circuit of the plurality of active electrical circuits can be coupled to at least one adjacent active electrical circuit of the plurality of active electrical circuits via at least one conductive flexible interconnection.

The apparatus can further include at least one conductive intermediate bus, where the at least one active electrical circuit of the plurality of active electrical circuits is coupled to the at least one conductive intermediate bus, and each active electrical circuit of the plurality of active electrical includes at least one sensing element.

The plurality of active electrical circuits can be configured to transmit one or more multiplexed signals to the at least one signal processor via the at least one conductive intermediate bus.

The at least one active electrical circuit of the plurality of active electrical circuits further can include at least one pass-through switch, where the at least one source-follower amplifier is coupled to the at least one pass-through switch.

Each of the active electrical circuit of the plurality of active electrical circuits can include at least one electrode, at least one source-follower amplifier coupled to the at least one electrode, and at least one pass-through switch coupled to the at least one source-follower amplifier.

The at least one source-follower amplifier can be an input transistor having a drain coupled to ground, where the pass-through switch is a pass-through transistor coupled to the input transistor.

A source of the input transistor can be coupled to a drain of the pass-through transistor.

A source of the pass-through transistor can be coupled to the drain of that respective pass-through transistor, where the respective at least one electrode of each active electrical circuit is coupled to a gate of the respective input transistor.

The input transistor can be a NMOS transistor.

The pass-through transistor can be a NMOS transistor.

The plurality of active electrical circuits can be read in a row-column arrangement, where each row-column element of the row-column arrangement corresponds to at least one active electrical circuit of the plurality of active electrical circuits.

The source of the pass-through transistor of each respective active electrical circuits can be coupled to a column output of each respective row-column element.

All columns of the row-column arrangement can be read substantially simultaneously, where a single row of the row-column arrangement is active when the columns of the row-column arrangement are read.

The source of the pass-through transistor of at least two active electrical circuits can be coupled to the column output of each respective row-column element.

Each row input of the row-column arrangement can be coupled to a gate of a pass-through transistor of each active electrical circuit of the plurality of active electrical circuits.

The voltage at the gate of the input transistor can determine the voltage at the source of the input transistor.

The present disclosure also provides a method for readout of one or more multiplexed signals. The method can include disposing an apparatus proximate to a surface. The apparatus includes a plurality of active electrical circuits disposed in a distributed arrangement on a flexible substrate forming an inflatable body, the plurality of active electrical circuits being configured to transmit one or more multiplexed signals to at least one signal processor. At least one active electrical circuit of the plurality of active electrical circuits includes an electrode, a source-follower amplifier coupled to the electrode, and a pass-through switch coupled to the source-follower amplifier, a row control switch and a column output. A voltage applied to the row control switch activates the pass-through switch such that a signal from the electrode is transmitted to the column output. The method further includes applying a voltage to the row control switch and reading an output at the column output thereby providing the one or more multiplexed signals.

The plurality of active electrical circuits can be are disposed proximate to the electrode in the distributed arrangement.

Each active electrical circuit of the plurality of active electrical circuits can be coupled to at least one adjacent active electrical circuit of the plurality of active electrical circuits via at least one conductive flexible interconnection. In an example, the method can further include transmitting the one or more multiplexed signals from the plurality of active electrical circuits to the at least one signal processor via the at least one conductive flexible interconnection.

The apparatus can also include at least one conductive intermediate bus, where the at least one active electrical circuit of the plurality of active electrical is coupled to the at least one conductive intermediate bus. In an example, the method further includes transmitting the one or more multiplexed signals from the plurality of active electrical circuits to the at least one signal processor via the at least one conductive intermediate bus.

The electrode can be coupled to a gate of the source-follower amplifier.

A source of the at least one source-follower amplifier is coupled to a drain of the at least one pass-through switch, where a gate of the pass-through switch is coupled to the row control switch, and where a source of the pass-through switch is coupled to the column output.

The drain of the source-follower amplifier can be biased to a ground potential.

The at least one active electrical circuits can include two active electrical circuits, where each of the two active electrical circuits is coupled to a respective row control switch, where the two active electrical circuits are coupled to a common column output, and where the voltage is applied to one of the row control switches during the reading of the output from the common column output.

The following publications, patents, and patent applications are hereby incorporated herein by reference in their entirety:

Kim et al., "Stretchable and Foldable Silicon Integrated Circuits," Science Express, Mar. 27, 2008, 10.1126/science.1154367;

Ko et al., "A Hemispherical Electronic Eye Camera Based on Compressible Silicon Optoelectronics," Nature, Aug. 7, 2008, vol. 454, pp. 748-753;

Kim et al., "Complementary Metal Oxide Silicon Integrated Circuits Incorporating Monolithically Integrated Stretchable Wavy Interconnects," Applied Physics Letters, Jul. 31, 2008, vol. 93, 044102;

Kim et al., "Materials and Noncoplanar Mesh Designs for Integrated Circuits with Linear Elastic Responses to Extreme Mechanical Deformations," PNAS, Dec. 2, 2008, vol. 105, no. 48, pp. 18675-18680;

Meitl et al., "Transfer Printing by Kinetic Control of Adhesion to an Elastomeric Stamp," Nature Materials, January, 2006, vol. 5, pp. 33-38;

U.S. Patent Application publication no. 2010 0002402-A1, published Jan. 7, 2010, filed Mar. 5, 2009, and entitled "STRETCHABLE AND FOLDABLE ELECTRONIC DEVICES;"

U.S. Patent Application publication no. 2010 0087782-A1, published Apr. 8, 2010, filed Oct. 7, 2009, and entitled "CATHETER BALLOON HAVING STRETCHABLE INTEGRATED CIRCUITRY AND SENSOR ARRAY;"

U.S. Patent Application publication no. 2010 0116526-A1, published May 13, 2010, filed Nov. 12, 2009, and entitled "EXTREMELY STRETCHABLE ELECTRONICS;"

U.S. Patent Application publication no. 2010 0178722-A1, published Jul. 15, 2010, filed Jan. 12, 2010, and entitled "METHODS AND APPLICATIONS OF NON-PLANAR IMAGING ARRAYS;" and U.S. Patent Application publication no. 2010 027119-A1, published Oct. 28, 2010, filed Nov. 24, 2009, and entitled "SYSTEMS, DEVICES, AND METHODS UTILIZING STRETCHABLE ELECTRONICS TO MEASURE TIRE OR ROAD SURFACE CONDITIONS."

Kim, D. H. et al. (2010). Dissolvable films of silk fibroin for ultrathin conformal bio-integrated electronics. *Nature Materials*, 9, 511-517.

Omenetto, F. G. and D. L. Kaplan. (2008). A new route for silk. *Nature Photonics*, 2, 641-643.

Omenetto, F. G., Kaplan, D. L. (2010). New opportunities for an ancient material. *Science*, 329, 528-531.

Halsed, W. S. (1913). Ligature and suture material. *Journal of the American Medical Association*, 60, 1119-1126.

Masuhiro, T., Yoko, G., Masaobu, N., et al. (1994). Structural changes of silk fibroin membranes induced by immersion in methanol aqueous solutions. *Journal of Polymer Science*, 5, 961-968.

Lawrence, B. D., Cronin-Golomb, M., Georgakoudi, I., et al. (2008). Bioactive silk protein biomaterial systems for optical devices. *Biomacromolecules*, 9, 1214-1220.

Demura, M., Asakura, T. (1989). Immobilization of glucose oxidase with *Bombyx mori* silk fibroin by only stretching treatment and its application to glucose sensor. *Biotechnology and Bioengineering*, 33, 598-603.

Wang, X., Zhang, X., Castellot, J. et al. (2008). Controlled release from multilayer silk biomaterial coatings to modulate vascular cell responses. *Biomaterials*, 29, 894-903.

U.S. patent application Ser. No. 12/723,475 entitled "SYSTEMS, METHODS, AND DEVICES FOR SENSING AND TREATMENT HAVING STRETCHABLE INTEGRATED CIRCUITRY," filed Mar. 12, 2010.

U.S. patent application Ser. No. 12/686,076 entitled "Methods and Applications of Non-Planar Imaging Arrays," filed Jan. 12, 2010.

U.S. patent application Ser. No. 12/636,071 entitled "Systems, Methods, and Devices Using Stretchable or Flexible Electronics for Medical Applications," filed Dec. 11, 2009.

U.S. Patent Application publication no 2012-0065937-A1, published Mar. 15, 2012, and entitled "METHODS AND APPARATUS FOR MEASURING TECHNICAL PARAMETERS OF EQUIPMENT, TOOLS AND COMPONENTS VIA CONFORMAL ELECTRONICS."

U.S. patent application Ser. No. 12/616,922 entitled "Extremely Stretchable Electronics," filed Nov. 12, 2009.

U.S. patent application Ser. No. 12/575,008 entitled "Catheter Balloon Having Stretchable Integrated Circuitry and Sensor Array," filed on Oct. 7, 2009.

U.S. patent application Ser. No. 13/336,518 entitled "Systems, Methods, and Devices Having Stretchable Integrated Circuitry for Sensing and Delivering Therapy," filed Dec. 23, 2011.

Further combinations and sub-combinations of various concepts are provided below in the claims section. It should be appreciated that all combinations of such concepts and additional concepts described in greater detail below (provided such concepts are not mutually inconsistent) are contemplated as being part of the subject matter disclosed herein. In particular, all combinations of subject matter appearing as numbered claims at the end of this disclosure are contemplated as being part of the subject matter disclosed herein. In addition, all combinations of subject matter supported by this disclosure, including the drawings, the description and the claims, are contemplated as being part of the subject matter even if not expressly recited as one of the numbered claims.

It should be appreciated that all combinations of the foregoing concepts and additional concepts described in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the subject matter described herein. The drawings are not necessarily to scale; in some instances, various aspects of the subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-3B show an example of an inflatable body, according to the principles herein.

FIG. 5A illustrates an example placement of the electronic structure of FIG. 5B on an inflatable body, according to the principles herein.

FIG. 5B illustrates an example electronic structure, according to the principles herein.

Figure 1:
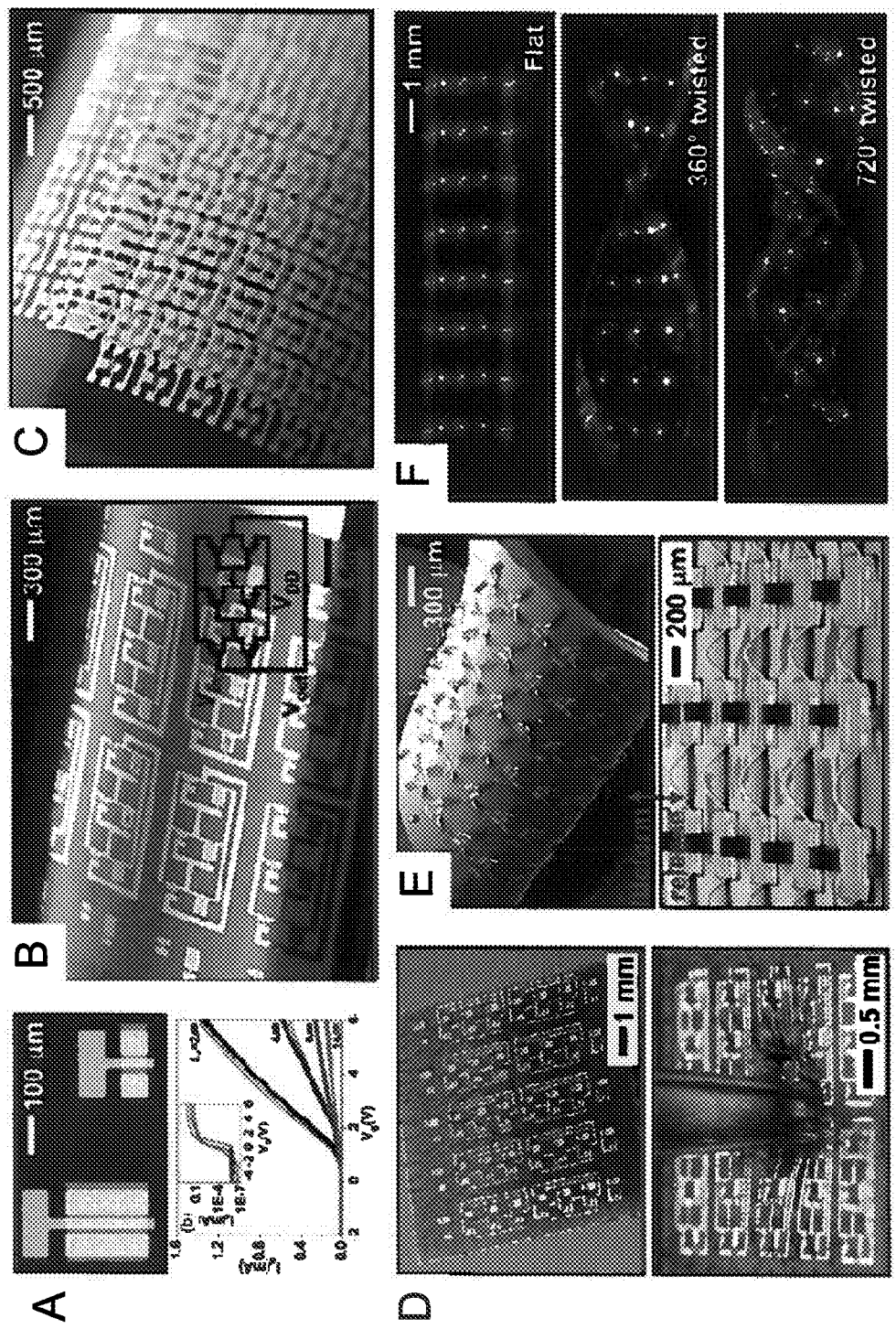
FIGS. 1A-1F depict example flexible and stretchable electronic and optoelectronic devices, according to the principles herein.

The features and advantages of the various examples will become more apparent from the detailed description set forth below when taken in conjunction with the drawings.

DETAILED DESCRIPTION

Following below are more detailed descriptions of various concepts related to, and examples of systems, methods and apparatus for use with balloon catheters and other types of catheters. The systems, methods and apparatus can be used for high density mapping and for multiplexed ready-out of sensing elements. It should be appreciated that various concepts introduced above and described in greater detail below may be implemented in any of numerous ways, as the disclosed concepts are not limited to any particular manner of implementation. Examples of specific implementations and applications are provided primarily for illustrative purposes.

As used herein, the term "includes" means includes but not limited to, the term "including" means including but not limited to. The term "based on" means based at least in part on.

As used herein, the term "disposed on" or "disposed above" is defined to encompass "at least partially embedded in."

Flexible, stretchable electronics address a multitude of applications found in nature that rigid electronics cannot. One example is a flexible neural array to map EEG data on the surface of the brain or of portions of cardiac tissue. Rigid electronics cannot conform to such surfaces.

Existing systems fail to provide implementations suitable for environments such as the surface of the brain or heart, particularly where such a system can quickly assess the relevant parameter at high spatial resolutions (e.g., through high-density mapping).

The present disclosure provides some examples of an apparatus for medical diagnosis and/or treatment that include a flexible substrate, an intermediate bus disposed on the substrate, and a plurality of sensing elements disposed on the flexible substrate. The plurality of sensing elements are coupled to the intermediate bus. The plurality of sensing elements and the intermediate bus are disposed on the flexible substrate such that the sensor elements are disposed at areas of minimal curvature and/or flexing of the flexible substrate.

In an example, the sensing elements are disposed in a close-packed array proximate to an end of the at least one intermediate bus. For example, the sensing elements can be formed in a square, circular, triangular, or diamond-shaped arrangement, or any other close packed arrangement, with each sensing element including an electrical connection that connects or otherwise communicates with a single intermediate bus.

In an example, the flexible substrate is a portion of an inflatable body. The flexible substrate or the inflatable body can be formed from any suitable flexible and/or stretchable material in the art. Non-limiting examples include polyethylene terephthalate (PET), polyurethane, and nylon.

In an example, the inflatable body can be configured as an expandable portion positioned near an end of a catheter. In non-limiting examples, the inflatable body can be a balloon catheter. For example, the inflatable body can be a balloon having a cylindrical morphology, a cone shaped morphology or dog-bone shaped morphology, an "onion"-shaped morphology (i.e., a shape that can exhibit different curvatures in x- and y-directions), or a barrel-like morphology. In another example, the inflatable body may have a compound shape. For example, the inflatable body may be rounded in shape in certain portions, and include at least one portion that is flattened. In another example, the inflatable body may be configured as a flattened stretchable portion that can be expanded or collapsed. In an example implementation, such a flattened portion of the inflatable body may be deployed to make substantially full contact with a portion of a tissue, e.g., as part of a tissue lumen.

In an example, the inflatable body may be mounted to a catheter such that the tip of the catheter does not protrude beyond the substantially flattened distal region of the inflatable body. For example, an inflatable body that ordinarily has the catheter extend beyond the tip may be inverted inside out such that the neck is popped inward. The inverted inflatable body may be adhered to an inner coaxial guidewire of a catheter and mounted on the catheter such that the catheter tip does not extend beyond the substantially flattened portion of the inflatable body. The inner guidewire can be extended for deployment of the inverted inflatable body and then retracted to form the flattened surface.

Non-limiting examples of a tissue lumen according to the principles of any of the examples described herein include the channel within a tubular tissue structure, such as but not limited to a blood vessel (including an artery or a vein), or to the cavity within a hollow portion of an organ, such as but not limited to an intestine, an oral canal, a heart, a kidney, or auditory canal, In an example, the intermediate bus can include conductive portions that facilitate electrical communication between the sensing elements and an external circuit. For example, the external circuit can include a signal processor. For applications where a high conductivity is beneficial, a metal or metal alloy may be used, including but not limited to aluminum or a transition metal (including copper, silver, gold, platinum, zinc, nickel, chromium, or palladium, or any combination thereof) and any applicable metal alloy, including alloys with carbon. Suitable conductive materials may include a semiconductor-based conductive material, including a silicon-based conductive material, indium tin oxide, or Group III-IV conductor (including GaAs).

In another example, the intermediate bus can include such conductive portions and also non-conductive portions. Such non-conductive portions can be used to achieve a symmetric shape and/or weight distribution of the intermediate bus, to introduce a mechanical stability to the intermediate bus-sensing elements system, to reduce or eliminate a strain at a junction between a connector from the sensing element and the intermediate bus, to encapsulate the conductive portions for performance, electrical and or mechanical stability, and/or to isolate the conductive portions from an external strain applied to the system during use in a medical diagnostic and/or treatment procedure. The non-conductive portion can be a polymeric material, such as but not limited to a polyimide, a polyethylene terephthalate (PET), or a polyeurethane. Other non-limiting examples of applicable polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer herein can be a DYMAX® polymer (Dymax Corporation, Torrington, Conn.) or other UV curable polymer.

In an example, the plurality of sensing elements can include one or more of multiple sensor types, such as but not limited to, impedance sensors (including bipolar electrodes), lateral strain sensors, temperature sensors, intracardiac electrogram (EGM) sensors, light-emitting diodes (LEDs), including micro-LEDs, transistors (including switches), multiplexors, recording electrodes, radiofrequency (RF) electrodes (including RF ablation electrodes), temperature sensors, and/or contact sensors (including impedance-based contact sensors).

In an example, the plurality of sensing elements can include combinations of different sensor types. In an example, the plurality of sensing elements can include components such as pacing electrodes, EGM electrodes, and bipolar electrodes. In another example, the plurality of sensing elements can include components such as impedance electrodes and contact sensing electrodes. In another example, the plurality of sensing elements can include power control components such as components that can perform ablation. In another example, the plurality of sensing elements can include active components such as components that can provide for local signal amplification, e.g., for buffering or to provide signal gain. In any example where the sensing elements include active components, the activation of the active component and the measurements from the active component can be multiplexed.

In any example according to the principles described herein, the sensing elements, including electrodes, can be formed as conformal components, to conform to a shape and/or movement of a surface over which they are disposed, including in flexibility and/or stretchability.

The example systems and apparatus described herein employ thin, conformal arrays of sensory electronics (sensing elements) embedded in flexible substrates. Non-limiting examples of such flexible substrates include silicone or polyurethane substrates. According to the principles described herein, the example systems and apparatus herein integrate conformal sensors along with semiconductor-based electronics on flexible substrates, such as but not limited to deployable sheets and balloons (inflatable body). The example systems and apparatus described herein facilitate integration of amplification, logic and switching capabilities onboard the systems or apparatus, thereby optimizing sensing and minimizing wiring schemes inside the apparatus or system.

Methods for fabricating an apparatus for medical diagnosis and/or treatment are also described. An example method includes providing an intermediate bus that is coupled to a plurality of sensing elements, disposing the intermediate bus about a region of an inflatable body, and disposing the plurality of sensing elements about a distal portion of the inflatable body such that the sensor elements are disposed at areas of minimal curvature of the inflatable body.

In any example described herein, an area of minimal curvature may correspond to, and/or lie proximate to, regions of low and/or minimal strain in the flexible substrate. For example, where the flexible substrate is part of an inflatable body, the area of minimal curvature may correspond to, and/or lie proximate to, regions of low and/or minimal strain in inflatable body in the deflated state.

In an example, the areas of minimal curvature may be determined from am understanding of the stress-strain behavior of the flexible substrate, such as by determining the repeatable folding behavior of an inflatable body, and of the flexing or bending behavior of another type of flexible substrate. In another example, Finite element analysis of the stress-strain profiles o a flexible substrate also enables mechanical optimization. The functional elements, such as sensing elements, intermediate buses, active electrical circuits and flexible interconnections described herein, can be positioned on the flexible substrate in the area(s) of minimal curvature of stretchable substrate (including the inflatable body), thereby minimizing failure modes during operation. In another example, failure modes can be minimized during operation when an inflatable body is being introduced into a tissue lumen prior to being deployed near a tissue region of interest by placing the functional elements at or near areas of minimal curvature. In another example, the distributed arrangement of circuit elements described herein can be positioned at areas of a flexible substrate away from regions of bending or flexing stress, to aid in the conformability of a system or apparatus to a surface.

An example method for fabricating an apparatus for medical diagnosis and/or treatment can include extracting the intermediate bus and the plurality of sensing elements from a carrier substrate prior to disposing the intermediate bus about the region of the inflatable body as described herein. In an example method, disposing the intermediate bus about the region of the inflatable body can include applying the coupling bus using a dissolvable tape backing.

In an example, the plurality of electrodes elements can include one or more of bipolar electrodes, intracardiac electrogram (EGM) electrodes, recording electrodes, and radiofrequency (RF) electrodes (including RF ablation electrodes).

In an example, any system or apparatus according to the principles described herein may be entirely or at least partially encapsulated by an encapsulating material, such as a polymer material (including any of the polymer materials described herein). An encapsulating material can be any material that can be used to laminate, planarize, or encase at least one component of a system or apparatus described herein, including any electronic or other type of component. For example, a method of fabricating any system or apparatus according to the principles described herein can further include encapsulating the system or apparatus. In an example, an encapsulating material can be disposed over, or otherwise applied to, an apparatus that includes the flexible substrate forming the inflatable body, the intermediate bus and the plurality of sensing elements disposed on the flexible substrate. In various examples, an encapsulating material can be disposed over, or otherwise applied to, solely to the plurality of sensing elements, and/or to the intermediate bus. In an example, a polyurethane can be used as the encapsulating material. In another example, the encapsulating material can be the same material as the material for the flexible substrate. Encapsulating any portion of the systems or apparatus described herein can be useful to enhance the mechanical stability and robustness of the system or apparatus, or to maintain electronic performance of the electronic components of the system or apparatus against a stress or strain applied to the system or apparatus during use.

In an example, any of the systems or apparatus according to the principles herein can be disposed on the inflatable body such that a functional layer of the system or apparatus lies at a neutral mechanical plane (NMP) or neutral mechanical surface (NMS) of the system or apparatus. The NMP or NMS lies at the position through the thickness of the device layers for the system or apparatus where any applied strains are minimized or substantially zero. In an example, the functional layer of a system or apparatus according to the principles described herein includes the plurality of sensing elements and/or the intermediate bus.

The location of the NMP or NMS can be changed relative to the layer structure of the system or apparatus through introduction of materials that aid in strain isolation in various layers of the system or apparatus. In various examples, polymer materials described herein can be introduced to serve as strain isolation materials. For example, the encapsulating material described hereinabove can be used to position the NMP or NMS, e.g., by varying the encapsulating material type and/or layer thickness. For example, the thickness of encapsulating material disposed over the functional layers described herein may be modified (i.e., decreased or increased) to depress the functional layer relative to the overall system or apparatus thickness, which can vary the position of the NMP or NMS relative to the functional layer. In another example, the type of encapsulating, including any differences in the elastic (Young's) modulus of the encapsulating material.

In another example, at least a partial intermediate layer of a material capable of providing strain isolation can be disposed between the functional layer and the flexible substrate to position the NMP or NMS relative to the functional layer. In an example, the intermediate layer can be formed from any of the polymer materials described herein, aerogel materials or any other material with applicable elastic mechanical properties.

Based on the principles described herein, the NMP or NMS can be positioned proximate to, coincident with or adjacent to a layer of the system or apparatus that includes the strain-sensitive component, such as but not limited to the functional layer. The layer can be considered "strain-sensitive" if it is prone to fractures or its performance can be otherwise impaired in response to a level of applied strain. In an example where the NMP or NMS is proximate to a strain-sensitive component rather than coincident with it, the position of the NMP or NMS may still provide a mechanical benefit to the strain-sensitive component, such as substantially lowering the strain that would otherwise be exerted on the strain-sensitive component in the absence of strain isolation layers. In various examples, the NMS or NMP layer is considered proximate to the strain-sensitive component that provides at least 10%, 20%, 50% or 75% reduction in strain in the strain-sensitive component for a given applied strain, e.g., where the inflatable body is inflated.

As a non-limiting example, ultrathin conformal nanomembrane sensors (about 250 nm in size), embedded in a substrate (such as but not limited to thin polyimide and elastomeric substrates of thickness about 50 µm to about 100 µm) in neutral mechanical plane layouts can accommodate significant mechanical durability with radii of curvature less than about 1 mm.

In various examples, the encapsulating material and/or the intermediate layer material may be disposed at positions coincident with the strain-sensitive component, including in the functional layer. For example, portions of the encapsulating material and/or the intermediate layer material may be interspersed with the strain-sensitive component, including at positions within the functional layer.

In an example, a system, apparatus and method herein can be used to administer a type of therapy to tissue during a medical diagnosis and/or treatment. The system, apparatus and method can be based on an apparatus that includes the flexible substrate forming the inflatable body and the plurality of sensing elements disposed on the flexible substrate, or a stretchable electronic system that includes a flexible annular interconnect and a plurality of electrodes coupled to the flexible annular interconnect, where the stretchable electronic system is disposed on an inflatable body. For example, any of the inflatable bodies described herein may be disposed near a distal portion of a catheter, and a type of therapy may be introduced to a region of tissue during the medical diagnosis and/or treatment. In an example, the type of therapy may be introduced through a shaft of the catheter. In an example, the therapy may be an ablative therapy and/or a drug administration. Non-limiting examples of ablative therapy include cryoablation, laser ablation, and high intensity ultrasound.

An example method of performing a medical diagnosis and/or treatment on a tissue includes disposing in proximity to the tissue an apparatus that includes a flexible substrate forming an inflatable body, a coupling bus, and a plurality of sensing elements that are coupled to the coupling bus. The one or more sensing elements of the plurality of sensing elements include contact sensors. The coupling bus is disposed near a distal end of the inflatable substrate, and the plurality of sensing elements are disposed about the inflatable body such that the sensing elements are disposed at areas of minimal curvature of the inflatable body. The method includes recording a measurement of at least one sensing element of the plurality of sensing elements. The measurement provides an indication of a state of a portion of the tissue.

In an example, the measurement can be used to provide an indication of a disease state of the portion of the tissue. In another example, the measurement can be used to provide an indication of a contact state of the portion of the tissue with the at least one sensing element of the plurality of sensing elements.

An example instrument and user interface is also described herein that can be used to display a representation of measurements of a plurality of sensing elements or active electrical circuits that are positioned proximate to surface (such as but not limited to a tissue lumen). In an example, a instrument and user interface described herein also can be used for mapping contact between a plurality of sensing elements or active electrical circuits with a surface. The measurement or mapping data can be used to provide a representation of a degree of contact between an inflatable body supporting the plurality of sensing elements or active electrical circuit and the surface. An example instrument and/or user interface can be used with any of the example systems, methods or apparatus described herein.

Example apparatus are also described for displaying a representation of measurements of a plurality of sensing elements or active electrical circuits that are positioned proximate to surface during a medical diagnosis and/or treatment of a tissue. In this example, the display apparatus includes a display, a memory storing machine-readable instructions, and one or more processor units to execute the machine-readable instructions. Execution of the machine-readable instructions causes the display to display the representation of the measurements. The representation includes a plurality of first indicators and a plurality of second indicators. Each first indicator corresponds to a sensing element of the plurality of sensing elements (or active electrical circuit) that measures a signal below a threshold value. Each second indicator corresponding to a sensing element of the plurality of sensing elements (or active electrical circuit) that measures a signal above the threshold value.

In an example, a measurement below the threshold value can be used as an indication that the corresponding sensing element of the plurality of sensing elements (or active electrical circuit) is not in contact with the tissue.

In an example, a measurement above the threshold value can be used as an indication that at least a portion of the corresponding sensing element of the plurality of sensing elements (or active electrical circuit) is in contact with the tissue.

In an example, a measurement below a first threshold value can be used to indicate a state of "no contact" or "no measurement" for a sensing element. In another example, a measurement above a second threshold value can be used to indicate a state of "contact" or "measurement" for a sensing element. In another example, a measurement between the first threshold value and the second threshold value can be used to indicate a state of "poor contact" or "poor measurement" for a sensing element or active electrical circuit.

In an example, each of the first spatial representations or each of the second spatial representations displays a first indication if the corresponding sensing element measures a signal above a threshold value. In another example, each of the first spatial representations or each of the second spatial representations displays a second indication if the corresponding sensing element measures a signal below a threshold value.

In an example, a system described herein can be used for mapping contact with a surface. The system includes an inflatable body, plurality of electrodes coupled to the inflatable body, an electronic display electrically coupled to the plurality of electrodes. The electronic display provides a visual reproduction of the spatial location of the plurality of electrodes on the inflatable body. The electronic display also changes a visual attribute of an electrode in the plurality of electrodes in response to a change in an electrical signal produced by the electrode, where the change in the electrical signal can be used to identify a contact condition of the electrode with respect to the surface.

In an example, the visual attribute can be a binary representation or a quantitative representation.

In another example, the active electrical circuits or sensing elements described herein include a flexible interconnect, and a plurality of impedance based electrode pairs coupled to the flexible interconnect. The electrode pairs are configured to measure impedance between two electrodes of the electrode pair.

For example, the tissue can be cardiac tissue, and the lumen can be the pulmonary veins of a subject.

The present disclosure describe example results that show the utility of contact sensing in connection with medical diagnostic and/or treatment procedures using an inflatable and/or expandable body, including cryoballoon ablation procedures.

Example systems and apparatus disclosed herein permit integration of components, including one or more electrodes, photodiodes, thermistors, micro-LEDs, and/or force sensors, or arrays of electrodes, photodiodes, thermistors, micro-LEDs, and/or force sensors, which may be deployed on flexible substrates. The systems and apparatus according to the principles herein can have a wide range of applications in the medical device industry.

An example therapy based on cryothermal energy represents an alternative ablation therapy to radio frequency (RF) energy for treating certain conditions, including cardiac arrhythmias. A cryoballoon system is capable of delivering cryothermal energy through the transition of nitrous oxide from liquid to gaseous phase. In this example implementation, the transition of nitrous oxide from liquid to gaseous phase may be caused by an increase in pressure and a concomitant decrease in temperature to about −50° C. during the cryoablative procedure. The pulmonary vein ostium may be the structural target for ablation in paroxysmal AF patients. Achieving occlusion near the antrum of the pulmonary veins assists with achieving effective lesion formation with cryoballoons.

Conformal electronics provided in various non-limiting examples herein may be adhered to polymeric and elastomeric surfaces (including balloons and sheets) and may be mechanically unfurl from the distal end of a catheter tube without causing signal degradation. The example implementations described herein facilitate multiple sensing modalities to be deployed in vivo in intracardial and epicardial spaces at high density arrangements of sensing elements. The low bending stiffness of the electronics described herein facilitate strong conformal contact to soft tissues (such as of the heart), without requiring pins or separate adhesives. Accordingly, high density mapping within the atria is afforded and insights into the mechanisms underlying CFAEs are allowed, including analysis of rotors and wave fronts in persistent AF cases. The example implementations described herein may be used to detect the presence of AF mechanisms at significantly reduce electrical mapping times while decreasing safety risks and improving clinical outcomes during ablation procedures.

Examples of inflatable bodies are described herein relative to a type of balloon catheter. However, the inflatable bodies applicable to the systems, methods and apparatus herein as not so limited. It is to be understood that the principles herein apply to any type of inflatable body (including an expandable body) on which stretchable electronic systems described herein can be disposed.

FIGS. 1A-1F depict example flexible and stretchable electronic and optoelectronic devices that can be implemented in accordance with the principles herein. FIG. 1A shows microscope images of a p-type (left) and n-type (right) metal oxide semiconductor (MOS) field effect transistor (FET) that can be implemented in various examples described herein. The bottom frame of FIG. 1A shows characterization result of a n-type MOSFET, including I-V and transfer characteristics. FIG. 1B shows example flexible devices implemented in various examples on a 25 μm polyimide substrate that includes n-type and p-type transistors (left), CMOS inverters (right) and three stage ring oscillator (center). FIG. 1D shows an example 3D multi-layer of active circuit positioned on a plastic substrate and FIG. 1D shows example 2D wavy stretchable CMOS circuits on an elastomeric substrate. The example wavy stretchable implementation shown in FIG. 1D is deformed in the figure pursuant to pushing down in the center of the substrate. FIG. 1E provides scanning electron microscopy (SEM) images of deformed (top) and un-deformed (bottom) CMOS inverter array with buckled or pop-up interconnections in accordance with illustrative examples of the present disclosure. Implementations of the present disclosure may be on thin elastomers, such as a elastomer that is approximately 1 mm thick. FIG. 1E shows example implementations of GaAs iLED arrays connected via serpentine pop-up interconnections under flat, 360° and 720° twisted state in accordance with various stretchable examples. Each of the example interconnections, substrates, and active circuits or components of an active circuit demonstrated in FIGS. 1A-1F demonstrate components that may be implemented in example systems, methods and apparatus according to the principles herein for diagnostic and/or therapeutic purposes.

In a non-limiting example, the high resolution mapping capabilities of the example systems, methods and apparatus described can assist in improving the understanding of "complex fractionated atrial electrograms" (CFAEs), rotors and the underlying causes of persistent AF and in the treatment thereof. For example, it is believed that CFAEs represent rapid electrical activity from a nearby driving force (rotor). This knowledge may also be implemented to diagnose and treat other complex arrhythmias, including, but not limited to ventricular fibrillation. Example systems, methods and apparatus disclosed herein can be used to provide a route to shorter, safer and more efficacious diagnosis and treatment of arrhythmias.

Figure 2:
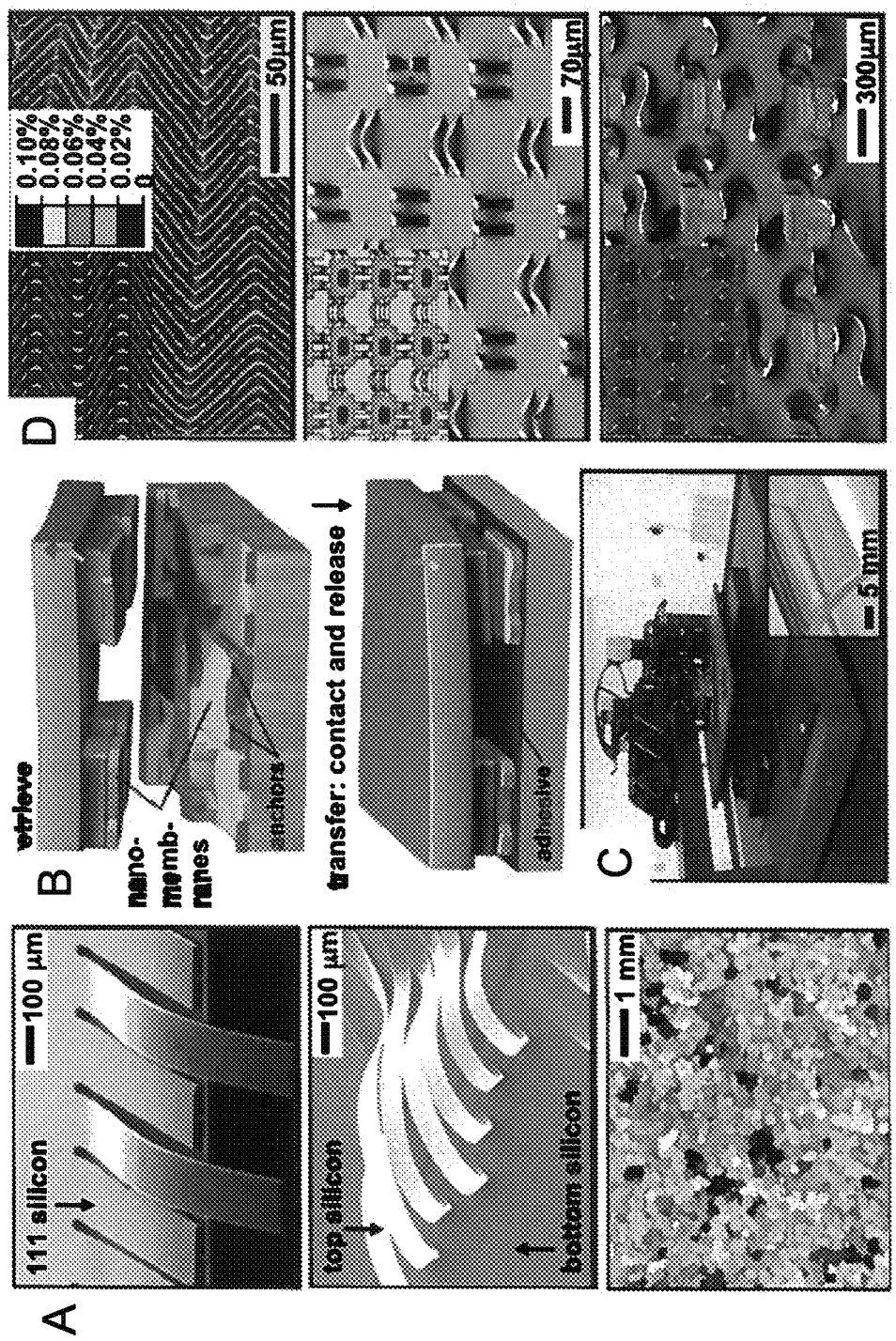
FIGS. 2A-2D illustrate non-limiting example processing methods and designs of electronic structures, according to the principles herein.

FIGS. 2A-2D illustrate non-limiting example processing methods and designs in accordance with the principles described herein. High density mapping techniques provided by various examples of the present disclosure may be achieved using micro-fabrication processing techniques applicable to ultrathin, flexible and stretchable single crystal nanomaterials. These processes may be based on silicon, including high quality single crystal wafers of (111) silicon (top), (100) silicon-on-insulator (SOI) (middle), or epitaxially grown III-V semiconductors (bottom) as shown in FIG. 2A. Lithography and a variety of etching techniques may be applied in various examples to define intricate patterns, which are subsequently released in ultrathin layers (for example hundreds of nanometers thick) from the fabrication wafer.

The released nanostructures may be integrated with flexible substrates using transfer print technology. FIG. 2B illustrates the transfer printing process which, in some example implementations, begin with a soft, rubber-like stamp called (poly)dimethylsiloxane (PDMS) that retrieves nanomaterials via van der Waals forces. As shown in the top frame of FIG. 2B, a stamp can be used to extract a fabricated structure from a fabrication wafer. As shown in the bottom frame of FIG. 2B, the stamp can contacted with a second substrate, such as a flexible substrate described herein, and the fabricated structure released onto the second substrate. This transfer process may be performed over large areas of segmented nanomembrane sensors using a flat stamp or over selected areas using a structured stamp. The extracted nano-membrane sensors can be selectively placed in pre-defined locations with microscale precision (bottom frame of FIG. 2B). An adhesive can be used to mount the fabricated structure to the flexible substrate to promote better adhesion strength and higher yield. For example, thin glue layers, such as polyimide or epoxies, can be used as the adhesive. An image of a representative GaAs nanomembrane array demonstrating the concept on a curved surface is shown in the inset of FIG. 2C. FIG. 2D shows example nanostructures that can be used to form the electronic structures described herein, including the "herringbone" structures (top frame of FIG. 2D), buckled structures (middle frame of FIG. 2D), and non-coplanar serpentine-shaped structures (bottom frame of FIG. 2D).

FIGS. 3A-3B show a non-limiting example of an inflatable body that is applicable to a system, method, or apparatus according to the principles herein. FIG. 3A shows the inflatable body 300 in a deflated state and FIG. 3B shows the inflatable body 300 in a partially inflated state. The inflatable body also includes a substantially flattened portion, i.e., a portion 304 of less or minimal curvature as compared to other regions of the balloon (see FIG. 3B). In this non-limiting example, the inflatable body is a balloon. As described above, the inflatable body can have a cylindrical morphology, a cone shaped morphology, dog-bone-shaped morphology, an "onion"-shaped morphology (i.e., a shape that can exhibit different curvatures in x- and y-directions), or a barrel-like morphology. In another example, the inflatable body may have a combination of any of these shapes.

In the non-limiting example of FIG. 3B, the inflatable body 300 is disposed on a catheter 302. As shown in FIG. 3A, the inner guidewire of catheter 302 can be extended to deflate n the inflatable body for deployment in a lumen. As shown in FIG. 3A, the inner guidewire of catheter 302 can be retracted to inflate the inflatable body and to form substantially flattened surface 304. The inflatable body 300 can have a more rounded shape when it is fully inflated. In an example method for performing a mapping of a surface according to the principles described herein, the inflatable body may be used for the mapping while it is only partially-inflated. In the partially-inflated state, much of the substantially flattened surface 304 can be placed proximate to, and make substantial contact with, a tissue or other surface to be mapped.

Figure 4:
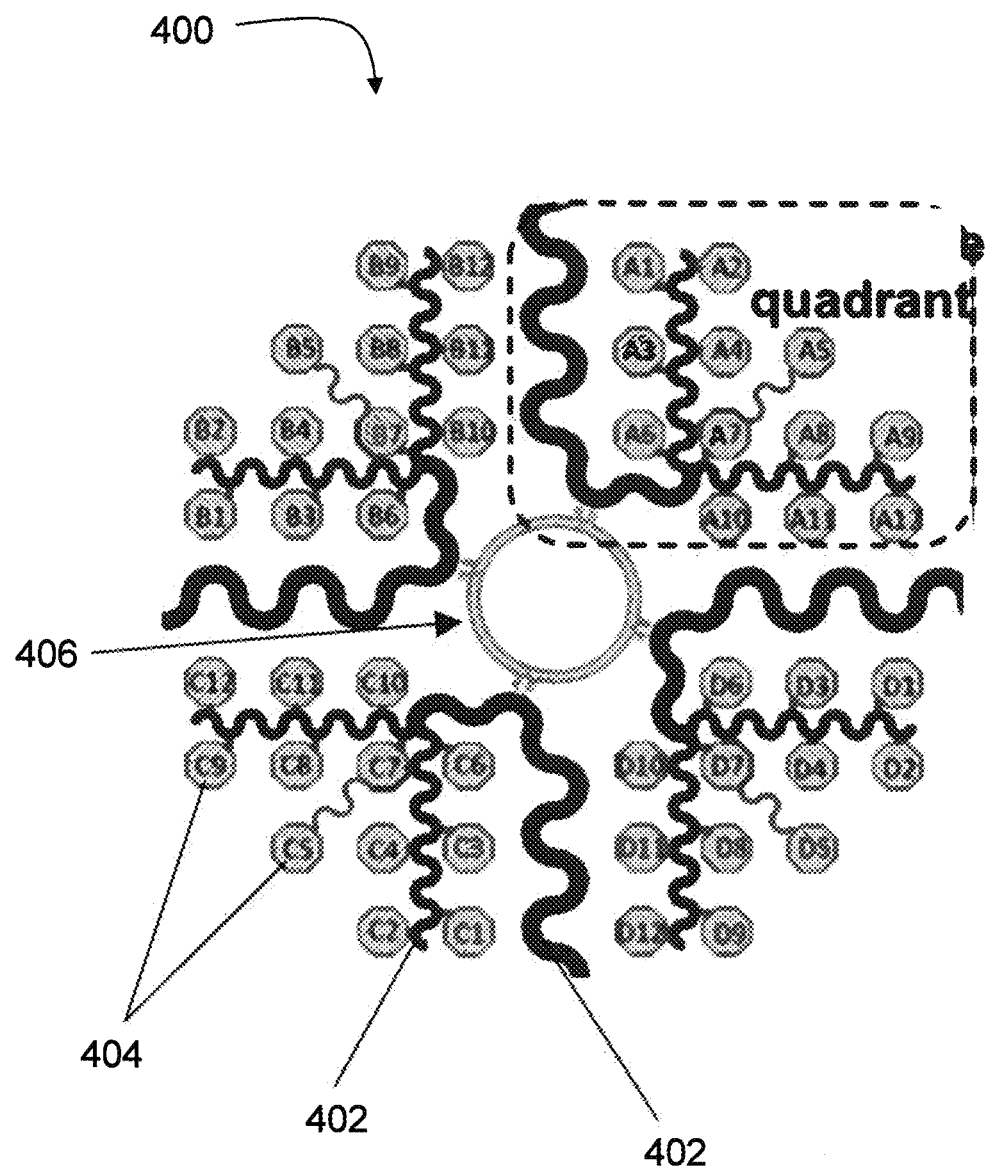
FIG. 4 shows an example computer-aided design (CAD) drawing of an electronic structure, according to the principles herein.

FIG. 4 shows a non-limiting example computer-aided design (CAD) drawing of an electronic structure 400 according to the principles described herein. The electronic structure 400 includes an intermediate bus 402 and sensing elements 404. The intermediate bus 402 can be coupled to a number of the sensing elements 404. For example, as shown in FIG. 4, intermediate bus 402 can be coupled to the sensing elements 404 in a quadrant of the electronic structure 404.

In the non-limiting example of FIG. 4, the electronic structure 400 includes four intermediate buses 402, each coupled to a number of sensing elements 404, and disposed in four quadrants. In other examples, the electronic structure can be formed from one intermediate bus, two intermediate buses, three intermediate buses, or more intermediate buses. In addition, the sensing elements can be disposed in arrangements with different symmetries.

As shown in the example of FIG. 4, a portion of the intermediate buses 402 may be coupled to a coupling structure 406. In other examples, the coupling structure 406 may be eliminated. The coupling structure 406 can be formed from a non-conductive material, including a non-conductive polymer-based material.

FIG. 5A illustrates an example placement of an electronic structure 500 (shown in FIG. 5B) on an inflatable body 502. As shown in FIG. 5A, the electronic structure 500 can be positioned at a distal region of the surface of the inflatable body 502. In this example, the electronic structure 500 is disposed at a substantially flattened portion of the inflatable body 502 (such as shown in FIG. 3B). A portion of the intermediate bus 504 of the electronic structure 500 is disposed about the distal region of the inflatable body 502; and the sensing elements 506 are disposed in an array on the inflatable body proximate to the distal region.

As shown in the example of FIGS. 5A and 5B, the electronic structure 500 can include a coupling structure 508 can be disposed about the distal region of the inflatable body 502. The coupling structure 508 can be used to provide mechanical stability to the electronic structure while it is being fabricated, extracted from the carrier substrate, and/or being disposed on the inflatable body. The coupling structure 508 also can aid in aligning the electronic structure 500 with the inflatable body 502. For example, the coupling structure 508 can be formed as a hollow ring structure that is disposed about an end of a catheter to which the inflatable body is attached.

Some of the examples herein, including the example of FIG. 5A, are described relative to the electronic structure being disposed on a flexible substrate that is part of an inflatable body. However, the flexible substrate is not limited to inflatable bodies. That is, in other examples, the electronic structures can be disposed on a flexible substrate that is not part of an inflatable body. For example, the electronic structures, including the intermediate bus and the sensing elements, can be disposed on a flexible substrate that is part of a patch, a bandage, or other substantially flat substrate.

Figure 6A:
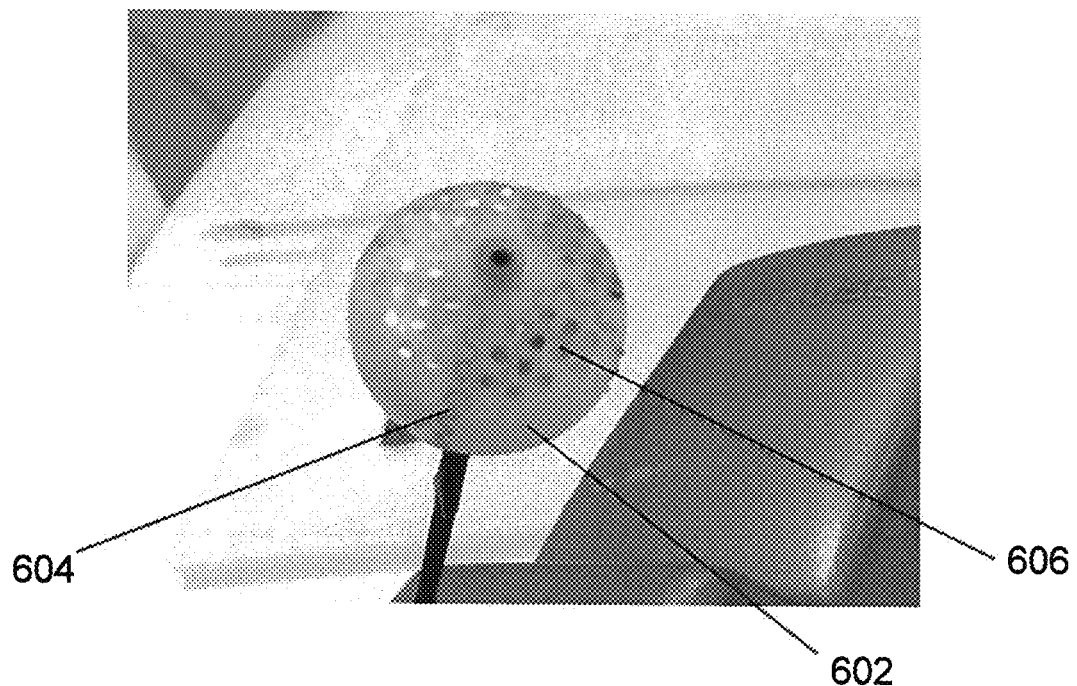
FIGS. 6A-6D show a non-limiting example implementation of an apparatus, according to the principles herein.

FIGS. 6A-6D show a non-limiting example implementation of an apparatus according to the principles described herein. FIG. 6A shows an inflatable body 602 in an inflated state. At least two intermediate buses 604 and a number of sensing elements 606 are disposed on portions of the surface of the inflatable body at or near to the distal portion of the inflatable body 602.

Figure 6B:
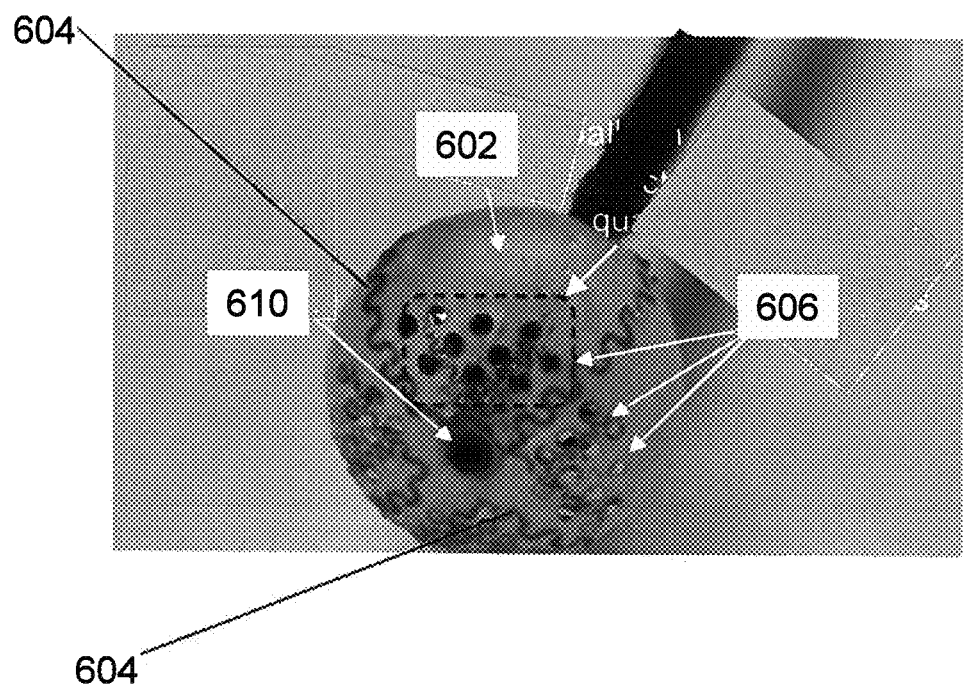

FIG. 6B shows a different perspective view of the apparatus shown in FIG. 6A. FIG. 6B also shows a port 610 in which other diagnostic and/or treatment devices can be positioned, including a cryoablation device.

Figure 6C:
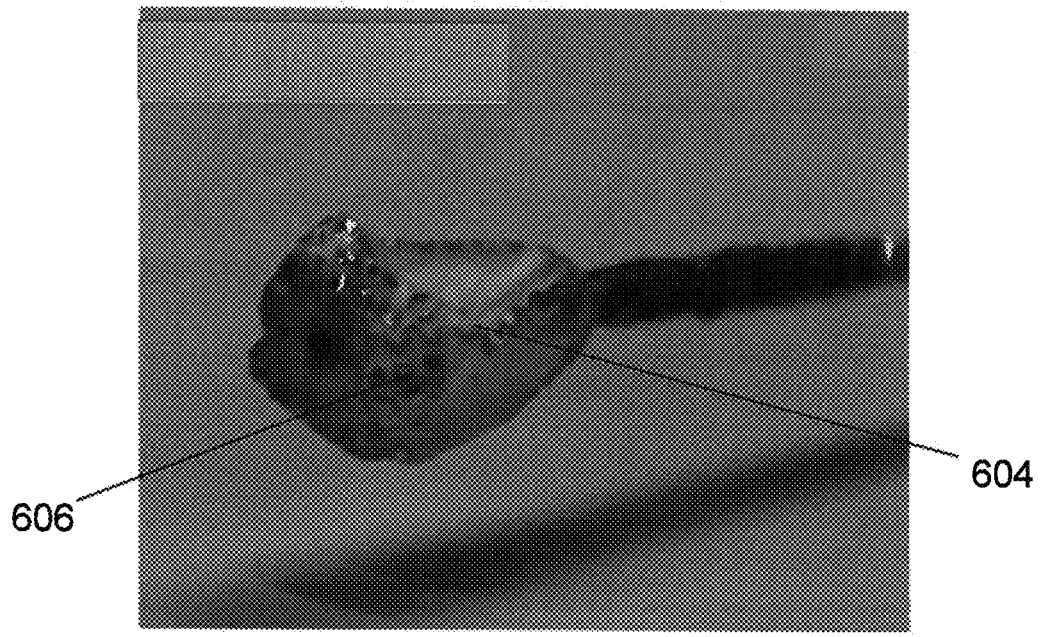
Figure 6D:
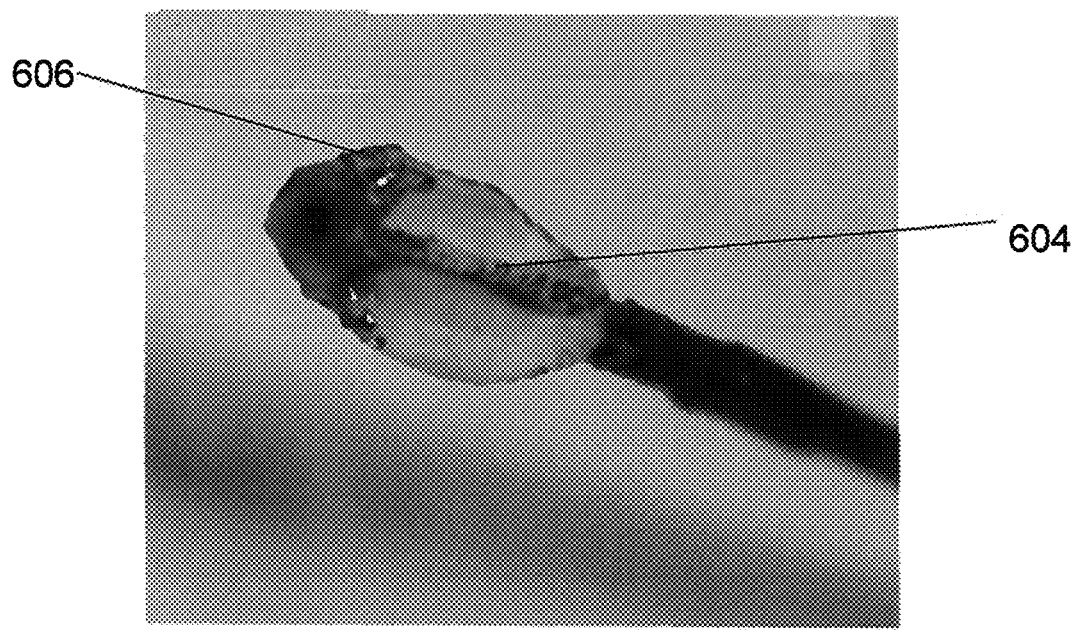

FIG. 6C shows the apparatus in a partially inflated state. FIG. 6D shows the apparatus in a deflated state. FIGS. 6C-6D show how the sensing elements (including various sensors) and the interconnects (including the intermediate bus) undergo compression when the inflatable body is deflated. As shown in FIG. 6C, the distal portion of the inflatable body that includes the sensing elements has less curvature than other portions of the inflatable body during the different stages of the deflation.

The electronic structure according to any of the examples described herein can be fabricated according to the processes described herein. The sensing elements of the electronic structure can be fabricated to include electrodes, including unipolar electrodes or bipolar electrodes, contact sensors or other types of sensors, and even integrated circuits. As described above in connection with FIGS. 2B-2C, the electronic structure can be printable, due to their ability to be removed and placed onto a target substrate using a soft, elastomeric stamp and transferred onto an inflatable body. This fabrication approach facilitates ultra-thin circuit layouts for mechanical flexibility to conform to lumen with different contours (such as but not limited to the unusual, surface roughness of the atria). This fabrication approach also facilitates the ability to perform multimodal sensing using a single system. As a non-limiting example, the single system can be a single catheter that includes an electronic structure according to an example herein and another diagnosis and/or treatment device, such as but not limited to a cryoablation device.

Figure 7:
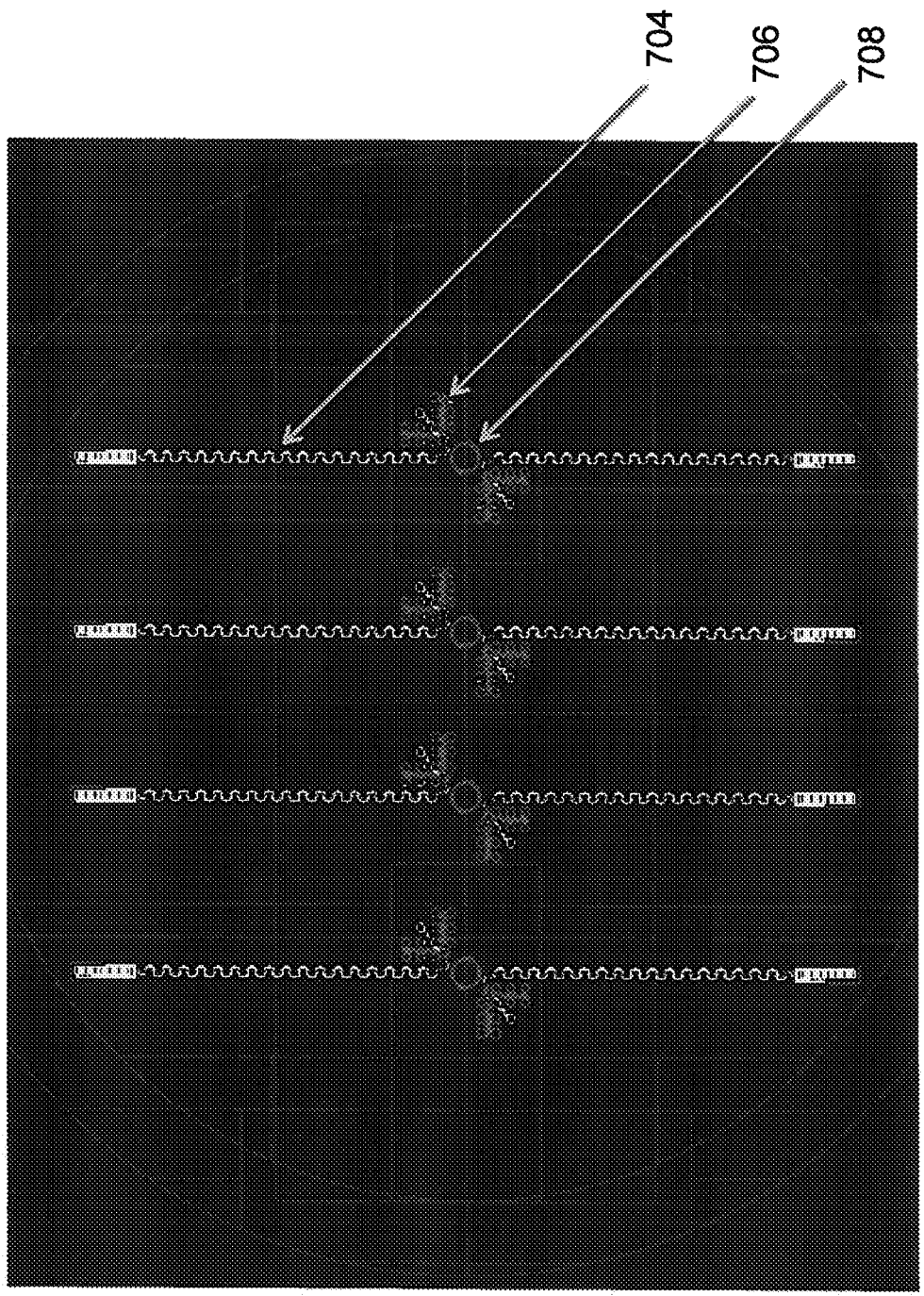
FIG. 7 shows an example representation for the fabrication of multiple electronic structures on a fabrication wafer, according to the principles herein.

FIG. 7 shows an example representation for the fabrication of multiple electronic structures on a fabrication wafer. Each example electronic structure includes at least one intermediate bus 704 and at least one array of sensing elements 706. The electronic structures can be fabricated in a packed arrangement, such as depicted in FIG. 7, on a fabrication wafer. In an example, lithographic processing and vertical trench wet-etching techniques can be used to yield isolated chiplets, such as but not limited to chiplets of area of about 0.1×0.1 mm$^2$, and about 1-5 μm thickness, that remain tethered to the underlying fabrication wafer through 'anchor' structures. This process can be used to yield the intermediate buses and sensing elements (including electrodes, contact sensors and other sensors), and even integrated circuits. These structures are printable due to their ability to be removed from the fabrication wafer, such as by using a stamp, and placed onto a target substrate, such as a flexible substrate, including a portion of an inflatable body, a patch or a bandage.

As also shown in FIG. 7, the electronic structure may be fabricated with a coupling structure 708. The coupling structure 708 can be formed from non-conductive materials. In an example, the coupling structure 708 can aid in providing mechanical stability to the electronic structure during the extraction using the stamp. In an example, the coupling structure 708 can aid in aligning the electronic structure when it is disposed on the inflatable body. In another example, the coupling structure 708 can include conductive portions. These conductive portions can be used as electrically conductive pathways such that sensing elements disposed in one section of the electronic structure can be electronically coupled to sensing elements and/or an intermediate bus disposed in a different section of the electronic structure.

Figure 8:
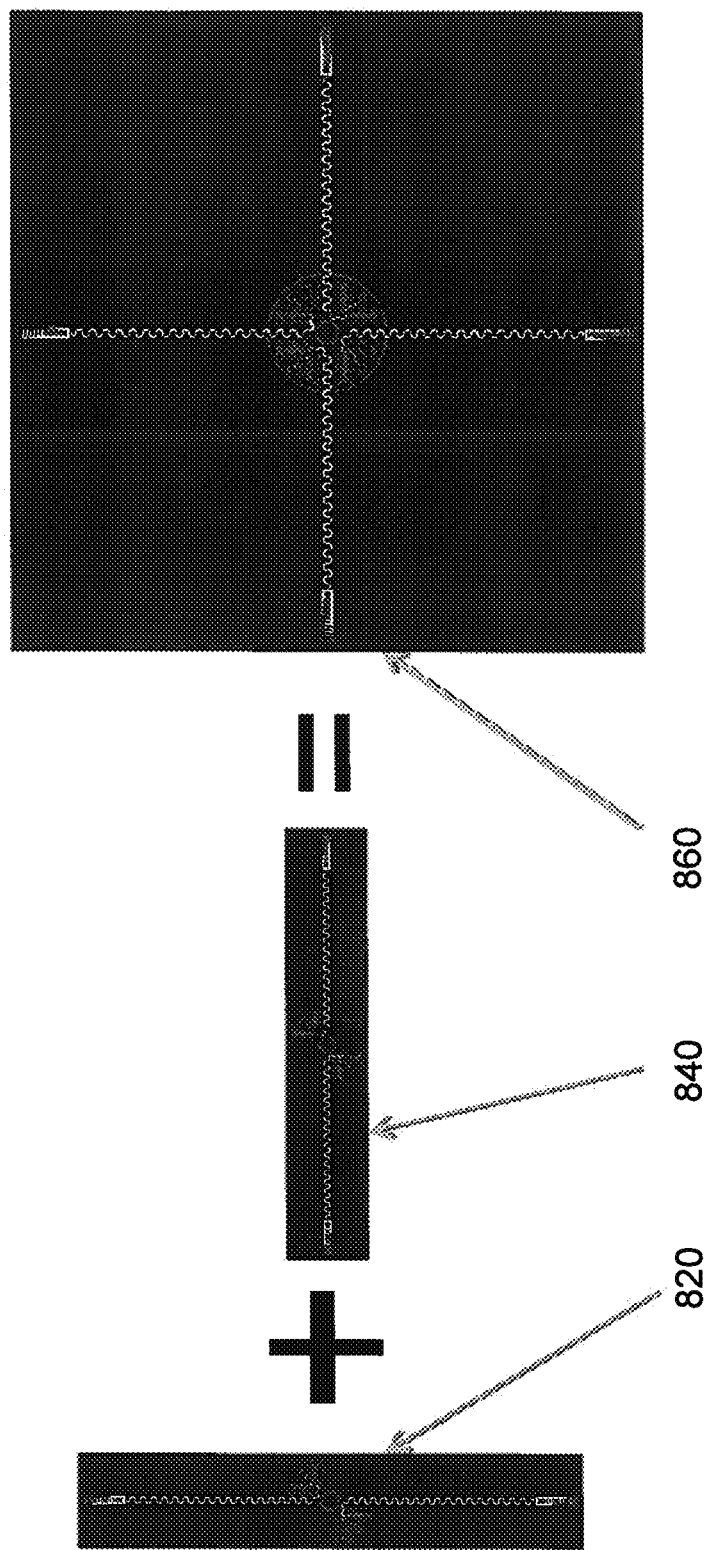
FIG. 8 shows an example method of integrating fabricated electronic structures, according to the principles herein.

FIG. 8 shows an example method of integrating fabricated electronic structures 820 and 840 to form an integrated electronic structure 860 with a larger number of sensing elements. For example, electronic structure 820 is rotated relative to electronic structure 840 and then coupled together to provide integrated electronic structure 860. The integrated electronic structure 860 can be disposed on a flexible substrate, such as a portion of an inflatable body, a patch, a bandage, or other flexible structure. In addition, the intermediate buses of the integrated electronic structure 860 can be coupled to one or more signal processors such that the signals from the plurality of sensing elements that form integrated electronic structure 860 can be read to provide one or more multiplexed signals from the measurements of the sensing elements.

In an example implementation, the electronic structures of FIGS. 4 through 8 can be used for mapping of a surface. The example systems and apparatus based on the electronic structures of FIGS. 4 through 8 can be used to obtain a high-density mapping of a surface. That is, the mapping implementation according to the principles herein can provide greater mapping capabilities and enhances signal to noise as compared to an electrical mapping catheter or other system that use sparse arrays of bipolar electrodes to gather electrical information at sparse points on a surface. In a system based on sparse arrays of bipolar electrodes, multiple, sequential recordings are superimposed via software to produce a static representation of electrical activity over a region of interest. This serial approach can be time consuming and can increase a risk of clinical complications in a medical application (such as a risk of stroke during use to map a portion of an atrium. A mapping implementation using a system or apparatus according to the principles herein can provide one or more multiplexed signals from a high density of sampled data points on a surface of interest, to provide a dynamic, high density map of the surface.

As a non-limiting example, the systems or apparatus according to the principles herein can present sensing elements arranged with packing densities of ranging from about 48 to about 64 per $cm^2$ to map a surface (such as but not limited to cardiac tissue) with proper contact feedback.

In addition to electrical mapping of a surface, sensing elements described herein that are impedance based contact sensors can be used to assess contact between the flexible substrate and the surface to be measured.

Figure 9:
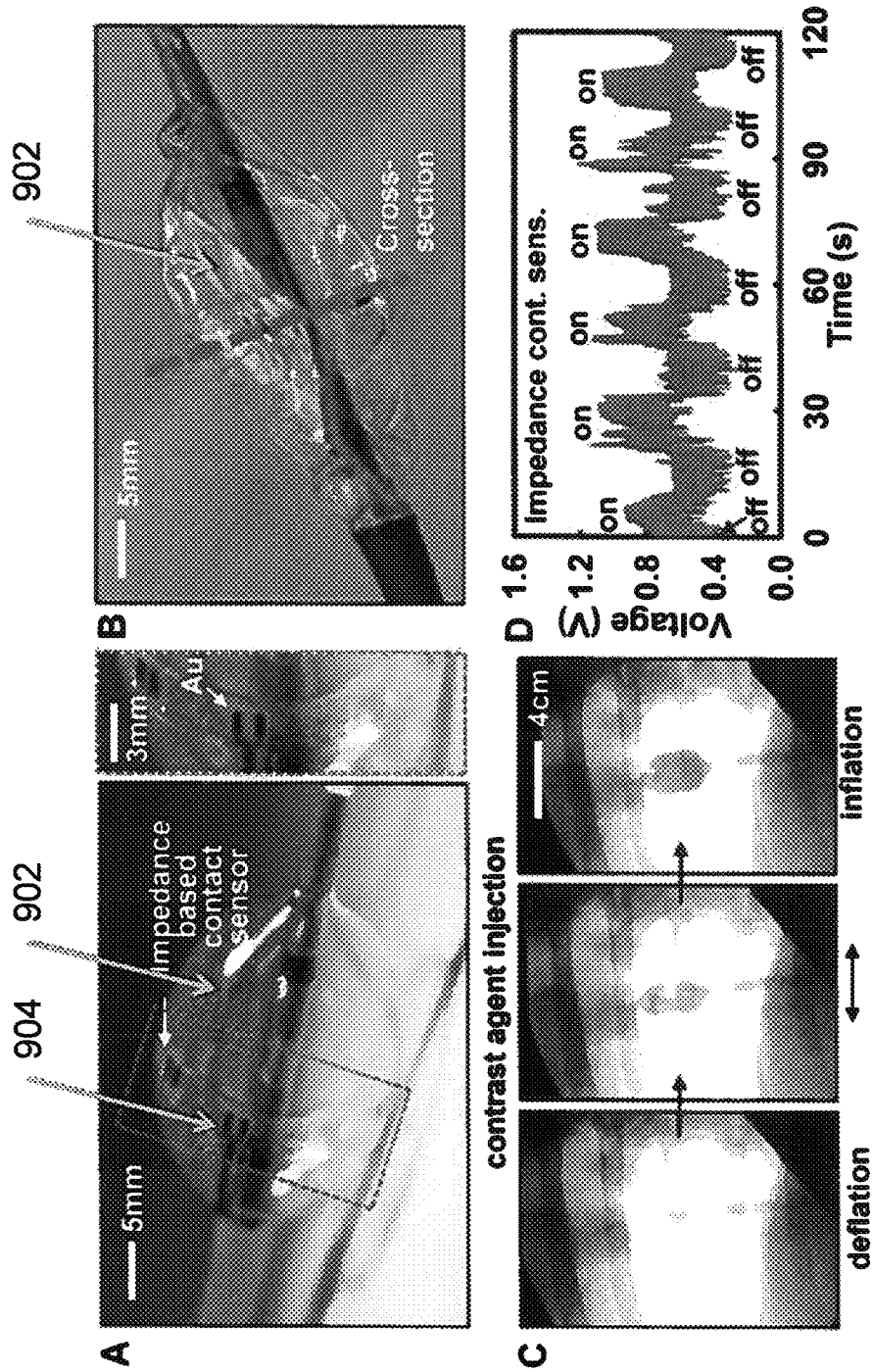
FIGS. 9A-9D illustrate an example operation of sensing elements that are impedance-based contact sensor, according to the principles herein.

Contact sensing during electrical mapping activity monitoring can provide a powerful capability. In a single platform, such a capability can enhance the safety and efficacy of a mapping procedure, such as but not limited to cardiac mapping. FIGS. 9A-9D illustrate an example operation of sensing elements that are impedance-based contact sensor. The impedance-based contact sensors can be bipolar electrodes. In this example, the sensing elements 904 are disposed on an inflatable body 902. FIG. 9A shows the inflatable body 902 in an inflated state, and FIG. 9B shows the inflatable body 902 in a deflated state. FIG. 9C shows an X-ray image of the inflatable body to demonstrate contact and non-contact conditions of measurements of a surface. In this example, the surface is near the superior vena cava in a live porcine model. The impedance-based contact sensors used in this non-limiting example can have simple and thin profiles (<5 µm), offer high sensitivity, fast response and mapping ability (including EGM mapping ability in medical applications). In other example implementations, the sensing elements may include conductive-silicone pads that provide quantitative measures of pressure.

In the example operation of the sensing elements including the impedance-based contact sensors, small amounts of AC current (<10 µA) are injected across the two terminals of the bipolar electrodes, and voltage changes caused by differences in conductivities of the surface of the surrounding media are measured. Example results show changes in impedance during on/off contacts. For example, FIG. 9D shows the results of measurements of the impedance contact sensors. The inflation and deflation cycling are seen to be coincident with sudden changes in values of the impedance, which coincide with the contact events.

A system, apparatus or method according to the principles described herein can be used as a platform for heterogeneous collections of high-performance sensor and actuator devices. They can provide versatile modes of operation with high sensor densities. For example, a system, apparatus or method according to the principles described herein can be used to facilitate measurement of electrophysiological activity of a surface and assessment of contact sensing using a single instrument. In an example, a system, apparatus or method that includes the intermediate bus and sensing elements disposed on a flexible substrate as described herein can be deployed through sheaths, provide signal fidelity, and be used to perform ablation procedures.

Any example apparatus or system described herein can be coupled to a data acquisition system for measurement and/or collection of one or more multiplexed signals from a measurement of the plurality of sensing elements. An example data acquisition system according to the principles described herein can be coupled with a voltage mapping user interface. The signals from the sensing elements can be conducted to the data acquisition system using the one or more intermediate buses.

In a non-limiting example implementation, the data acquisition system includes two modules to measure contact and electrograms. A transistor, such as but not limited to a MMBT4403 PNP transistor, can be placed in the feedback path of an operational amplifier, such as but not limited to a AD8671 operational amplifier, to create a voltage-controlled current source. For contact sensing, two custom, multichannel software-controlled current sources can be used to operate the array of sensing elements. A National Instruments PXI-6289 data acquisition card, controlled with custom LABVIEW™ software, controls voltages across the sensing elements. The excitation is provided using a DC current between 50 µA to 1 mA. The electrophysiological signals detected by the sensing elements arrays are conditioned with an Intan Technologies RHA1016 multiplexed biopotential amplifier. A digital signal processing system (Grapevine system, Ripple Inc) is used to convert the multiplexed analog signal from the RHA1016 to digital output. The output of the RHA1016 biopotential amplifier is sampled at 300 ksps and decimated at 1 ksps for individual channels. In addition, the Grapevine system is used to apply a digital 50/60 Hz notch filter to the signal. The data is recorded in the Cyberkinetics NEV2.2 NS2 format and viewed with custom Matlab software for real time analysis of voltage and isochronal maps of depolarization/hyperpolarization wave fronts. In another example, the electrogram data can be processed with a commercial GE Prucka Cardiolab system (unipolar and bipolar modes). Missing or noisy electrograms can be synthesized with a wave equation based (WEB) interpolation strategy. The electrograms can be subsequently analyzed and visualized using spatio-temporal voltage and phase mapping algorithms.

Figure 10:
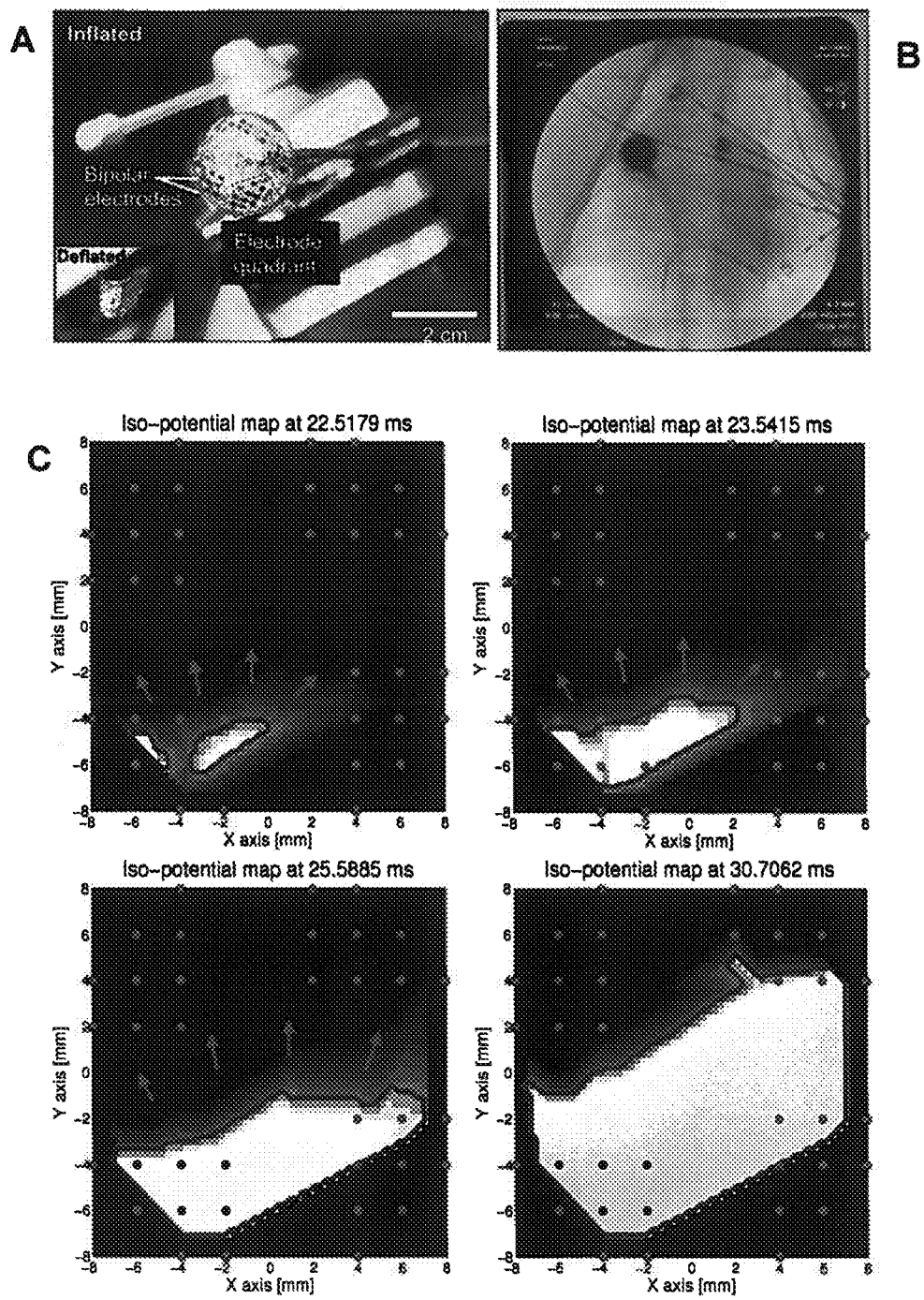
FIG. 10 shows results of an example implementation of use of sensing elements disposed on a flexible substrate, according to the principles herein.

FIG. 10 shows results of an example implementation of use of sensing elements disposed on a flexible substrate of an inflatable body for performing measurements of a surface. The one or more multiplexed signals from the sensing elements are transmitted to the data acquisition system via the one or more intermediate buses. FIG. 10A shows the sensing elements configured as bipolar electrodes in four quadrants on the inflatable body, each quadrant including about 12 to 16 bipolar electrodes. FIG. 10B shows an X-ray image of the inflatable body deployed inside a right atrium near the superior vena cava. FIG. 10C shows four isopotential maps in the right atrium, representing four different snapshots of measurements in time. The activation pattern in the panels of FIG. 10C shows propagation of a wavefront at about 1.5 m/s. The electrograms are synthesized using a wave-equation based interpolation.

In a non-limiting example implementation, an inflatable body according to the principles described herein can be mounted to a catheter having a steerable sheath. The steerable sheath allows the catheter including the inflatable body and the electronic structure to achieve substantially full contact with a surface (such as but not limited to atrial walls). Once contact is established, the mode of sensor measurement (such as but not limited to electrical sensing) can be toggled from measuring unipolar and bipolar electrograms to measuring monophasic action potentials (MAPs). In the MAP configuration, extracellular measurements can be used to provide improved performance over unipolar/bipolar recordings, including increased robustness to far field interference, local identification of polarization and depolarization timings, and substantially accurate recordings of action potential duration. Having the mapping electrodes in good contact can facilitate obtaining stable MAP recordings, since the waveform amplitude can be approximated as proportional to the applied pressure. A catheter that includes an inflatable body and electronic structure according to the principles of the present disclosure (such as with flattened surface geometries) can provide better performance as compared to existing devices and provide multimodal sensing (electrical mapping and contact sensing). Measurements performed using the apparatus, systems and methods according to the principles described herein provide for advanced signal processing techniques such as filtering, time-frequency analysis, and instantaneous phase singularity tracking. These high-density multisensory mapping and ablation capabilities can facilitate identification and treatment of persistent AF with a single device.

Figure 11:
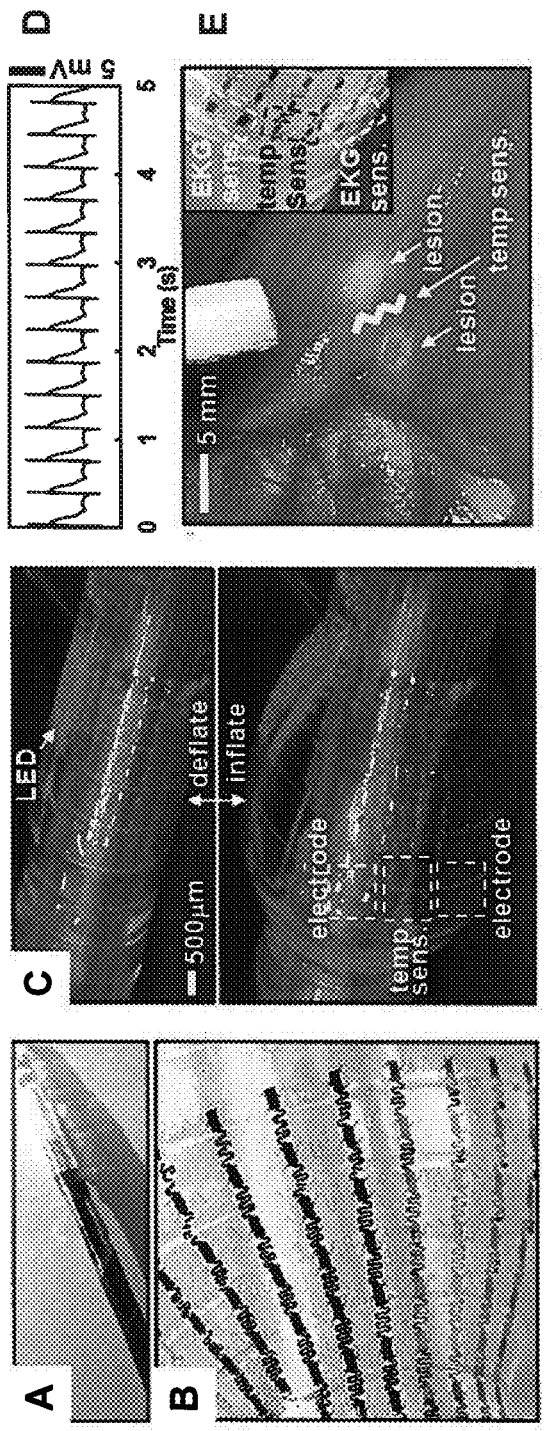
FIG. 11A-11C illustrate a non-limiting example multifunctional apparatus and systems according to the principles described herein, according to the principles herein.

FIG. 11A-11C illustrate a non-limiting example multifunctional apparatus and systems according to the principles described herein. FIGS. 11A-11C show examples of arrays of sensing elements disposed on inflatable bodies. The non-limiting example apparatus and systems use thin, conformal arrays of sensing elements embedded on flexible substrates. FIG. 11A shows an image of multifunctional sensor arrays mounted on an inflatable body, such as a catheter balloon. FIG. 11B presents a magnified view of the apparatus of FIG. 11A, where the inflatable body is inflatably stretched to approximately 120% and includes electronic structures disposed on its surface. FIG. 11C shows another perspective view of the multifunctional apparatus demonstrated in FIGS. 11A and 11B in deflated and inflated states, without external illumination. The example apparatus of FIG. 11C includes temperature sensors and stretchable arrays of m-ILEDs. In an example, the multifunctional apparatus includes a plurality of sensing elements as described herein, and at least one other device. In various examples, devices such as but not limited to electrophysiology (EP) electrodes, radio frequency (RF) ablation electrodes, temperature sensors, contact sensors and array of iLEDs may be mounted in or on the example apparatus or system.

FIG. 11D shows example electrogram recordings from an inflated balloon substrate positioned in direct mechanical contact with a live porcine heart. This mode of operation can be useful for balloon ablation catheters, where assessment of ablation can be achieved quickly, without the need for separate diagnostic devices. In addition to electrical and temperature sensors, impedance-based contact sensors and stimulation electrodes also can be included in or on various example apparatus. Contact sensors can be used to report the time and/or degree of contact between the inflatable body (the balloon skin) and the surface to be measured (endocardial tissue), thereby providing feedback (without x-ray imaging) on how to adjust and maneuver the inflated body to achieve optimal contact with cardiac tissue.

Figure 12:
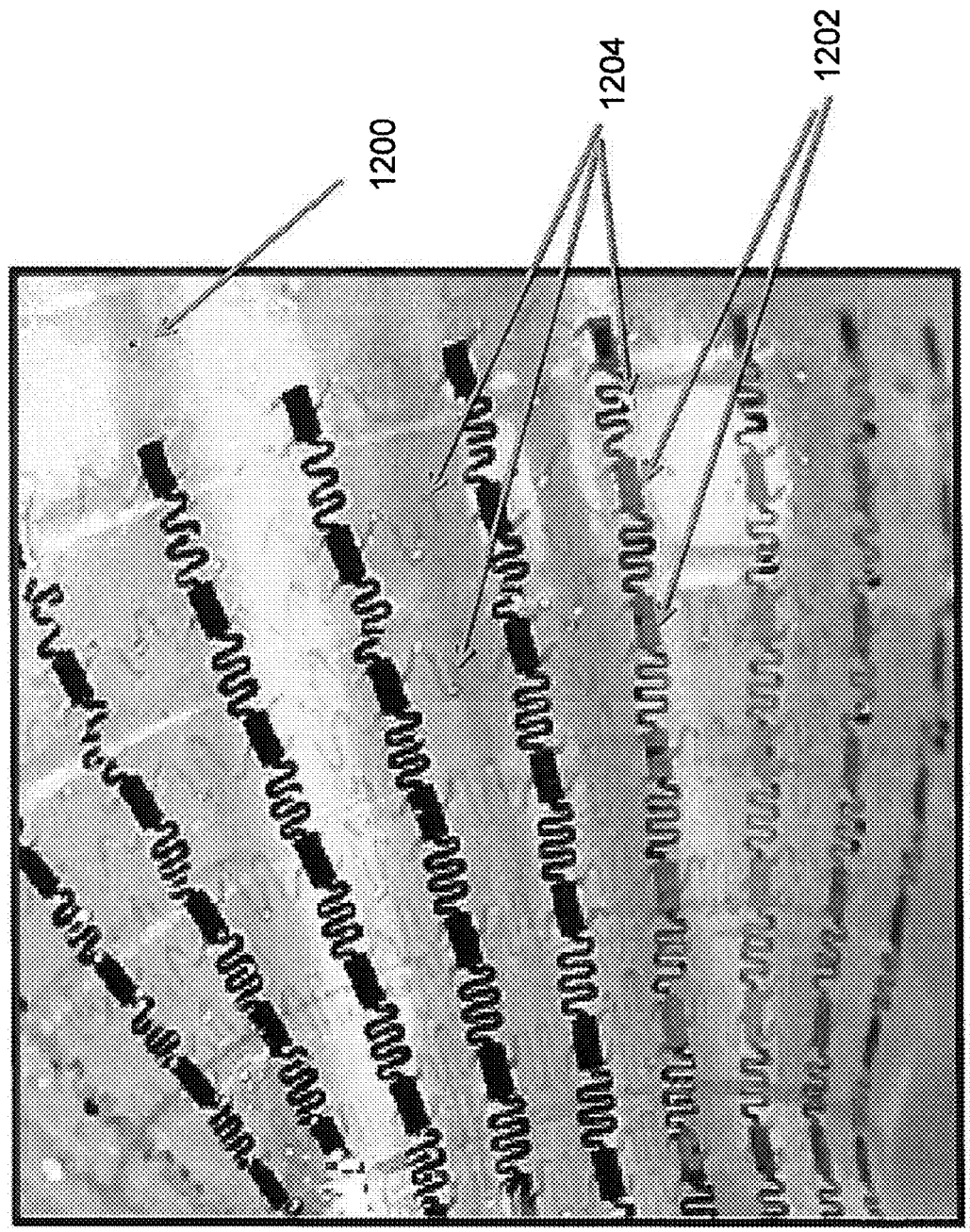
FIG. 12 shows a magnified view of the apparatus of FIG. 11B, according to the principles herein.
Figure 13:
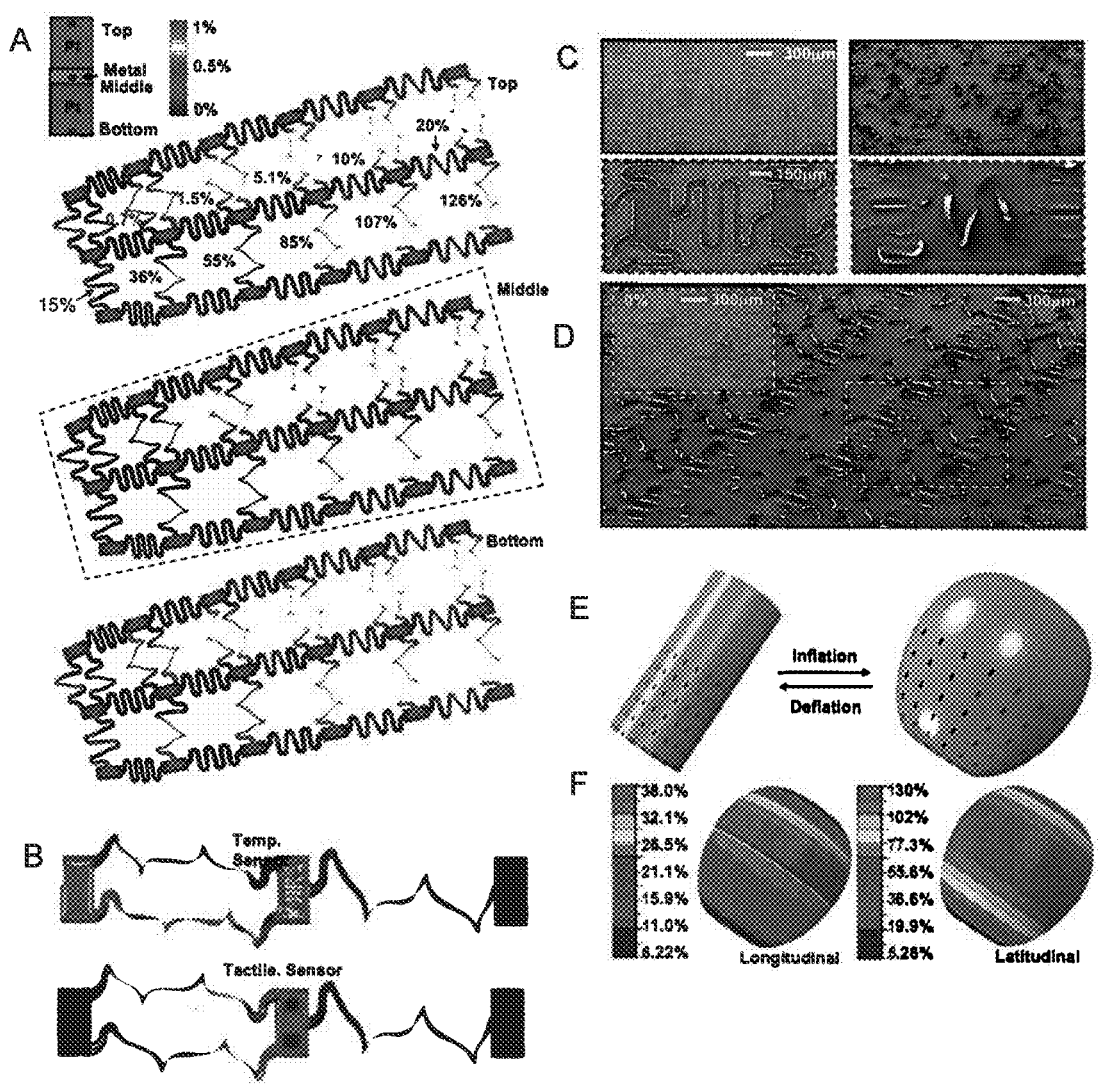
FIGS. 13A-13F show modeling result for an example apparatus according to the principles of FIG. 12, according to the principles herein.

FIG. 12 shows a magnified view of the apparatus of FIG. 11B. The apparatus for generating one or more multiplexed signals includes a flexible substrate 1200, and a plurality of active electrical circuits 1202 coupled to the flexible substrate 1200. As shown in FIG. 12, each active electrical circuit 1202 is coupled to another active electrical circuit 1202 via at least one conductive flexible interconnection 1204. The plurality of active electrical circuits are configured to transmit the one or more multiplexed signals to at least one signal processor.

In this non-limiting example structure, the active sensor circuits are connected via serpentine interconnections in accordance with the principles described herein. In a non-limiting example, the active electrical circuits 1202 can include electrodes for electrical mapping integrated on the flexible substrate.

FIGS. 13A-13F show modeling result for an example apparatus according to the principles of FIG. 12. Using modeling simulations, the dynamic material and mechanical properties of conformal sensor arrays and balloons can be characterized. Analytical and finite element modeling of the mechanics of stretchable electronics affixed to balloon catheters are performed. FIGS. 13A-13F also illustrate the impact of stretching to strain and positions of active electronic circuits positioned on a stretchable substrate in accordance with various examples. The strain distributions obtained through analytical and computational modeling can capture, quantitatively, the nature of deformations in the electronics layers of various examples. Characterization of the effective strain and displacement distributions in the sensor islands and serpentine interconnects can provide insight into critical fracture strains and buckling phenomena. Such characterization of conformal sensors can improve the way stretchable electronics on highly flexible substrates are implemented. The modeling can also be used to estimate mechanical stresses involved during catheter deployment in vivo.

In a non-limiting example, systems and methods according to the principles herein may be implemented in Langendorff-perfused hearts to demonstrate the capability of high density conformal sensors. In a non-limiting example, conformal sensors using more than 288 active circuits per $cm^2$ are used to provide insight into depolarization wave fronts in live porcine hearts. Examples of the present disclosure may be implemented using active circuit densities ranging from approximately 200 to 512 per $cm^2$. The data obtained from such a system may be analyzed using custom data acquisition.

Ultrathin geometries of sensing elements and interconnects implemented in the example systems and apparatus described herein can impart flexibility to otherwise rigid and brittle materials. Ultrathin conformal nanomembrane sensors, for example approximately 250 nm, embedded in or coupled to thin polyimide and elastomeric substrates, for example substrates approximately 50-100 μm, in neutral mechanical plane layouts, can accommodate mechanical durability with radii of curvature greater than about 1 mm. To achieve conformal sensors with such designs, densely packed arrays of electrodes may be formed on silicon wafers (0.6 μm CMOS process) or by thinning conventional semiconductor wafers (such as silicon wafers). Lithographic processing and vertical trench wet-etching techniques may be used to yield isolated chiplets, for example chiplets approximately 0.1×0.1 mm$^2$, and approximately 1-5 μm thick, that remain tethered to the underlying wafer through 'anchor' structures. This process may be used to yield electrodes, temperature sensors, contact sensors and even integrated circuits that we refer to as 'printable', due to their ability to be removed and placed onto a target substrate with a soft, elastomeric stamp. Measurement of individual sensors and transistors formed in this manner indicate high performance. The electrodes generally have 100-300 ohms characteristic impedances and the Si-based transistors had relatively high electron and hole mobilities (approximately 530 and approximately 150 cm$^2$/Vs; ON/OFF ratios greater than 105) similar to conventional electronics. These processes provide a route to developing amplifiers and multiplexers in accordance with various examples to significantly reduce the number of wires running along catheters.

Figure 14:
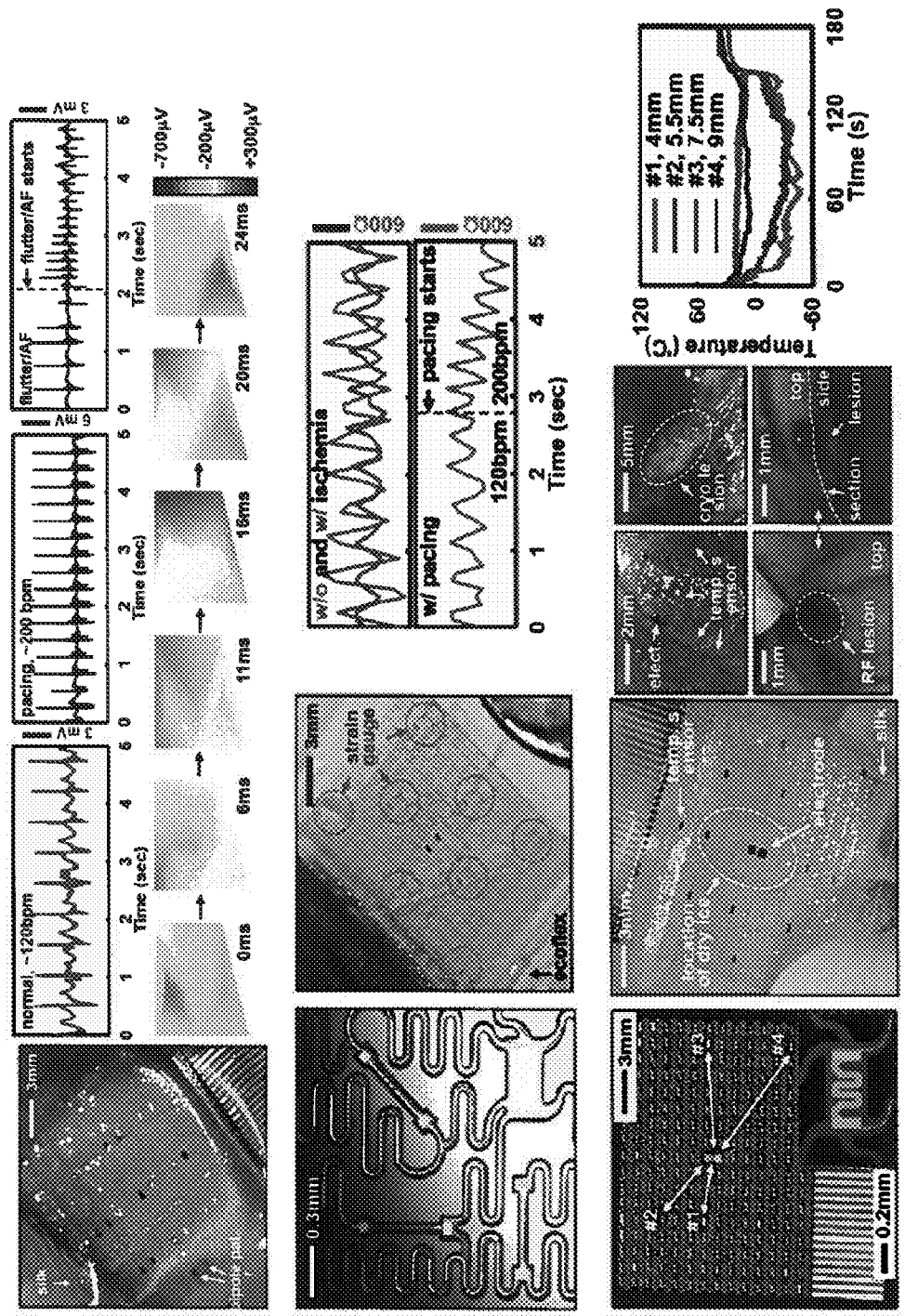
FIG. 14 shows epicardial recordings of EGM, temperature, and strain readings obtained from a rabbit heart, according to the principles herein.

FIG. 14 shows epicardial recordings of EGM, temperature, and strain readings obtained from a rabbit heart via various examples. The examples illustrated in FIG. 14 implement Au electrodes (16 channels) deployed on the epicardial surface of a live rabbit heart. These arrays include bipolar electrodes for electrical mapping. More specifically, FIG. 14 shows photographs of electrodes on a live rabbit heart. FIG. 14 also shows EGM recordings demonstrating activity during normal, pacing, and abnormal rhythms. Surface contour map of depolarization show that 16 channels may provide insight into wave front propagation even at low densities of conformal sensors. FIG. 14 also illustrates 24 channel strain gauge sensors which may be used to rhythmic beating of heart during normal, abnormal, and pacing rhythm. FIG. 14 also demonstrates conformal temperature sensor array (16 channels) with bipolar electrodes. FIG. 14 also shows temperature measurements on epicardial surface of rabbit heart during cryolesion formation. Temperatures down to −50° C. are recorded with conformal sensors. The attractive features of this approach include: (1) ultrathin circuit layouts for mechanical flexibility to conform to the unusual, surface roughness of the atria, (2) custom data acquisition system to select and process data across many rows and columns of electrodes, along with contact sensors, and temperature sensors, which operate by applying constant current and recording changes in voltage.

A non-limiting example data acquisition system for high-density mapping systems in accordance with various examples may acquire differential signals from up to 1024 individual channels. A suite of data-acquisition consoles may be provided that include temperature sensing and pressure-sensing modules, and an electrophysiological-mapping module. The temperature and pressure sensing circuits send controlled programmable current across their respective sensor terminals. The AD8639 operational amplifier with an MMBT5088 in feedback generates the voltage-controlled constant current. A switch toggles between two current ranges. Voltage changes across these sensors are monitored by an NI PXI-6289 and PXIe-10731 data acquisition board.

The electrophysiological signals detected by the electrode arrays are conditioned with the Intan RHA1016, a multiplexed biopotential amplifier array. The RHA1016 provides common-mode rejection, gain, low-pass filtering at 5 kHz and multiplexing. A Ripple Grapevine system converts the multiplexed analog signal (32-64 channels) from the RHA1016 to digital output. It samples the output of the RHA1016 at 300 ksps and decimates the signal to 1 ksps. In addition, it applies a digital 50/60 Hz notch filter to the signal. The preliminary data may be recorded in the Cyberkinetics NEV2.2 NS2 format. The data may then be viewed with software, such as custom MATLAB™ software. This implementation provides a foundation for building larger multichannel systems with more than 512 bipolar electrode channels.

Examples achieving data acquisition system including 100s to 1000s of channels may implement circuitry with local row and column select functionality on the flexible substrate. After the active electrodes gain and multiplex the signal, the signal can be high-pass filtered on a custom signal conditioning board to remove DC offsets. The signal then passes through a multi-pole linear phase low-pass/anti-aliasing filter to remove high, out of band frequencies. Thirty-two 1.3MSPS SAR ADCs can simultaneously sample the signal providing enough conversion speed to oversample 1024 channels and still provide digitally-filtered signals of 2 kHz bandwidth. Real-time digital filtering can be performed by Xilinx Virtex5 FPGAs to provide clarity and improve the visualization of the depolarization wave fronts. In addition, the FPGA can control the row/column multiplexing and data demultiplexing of the active electrode array. Once collected, the data can be demultiplexed, stored, and displayed with custom MATLAB™ software (The MathWorks). Fast Fourier transforms (FFTs), frequency gradient and dominant frequency analysis during AF are supported by this platform.

Figure 15:
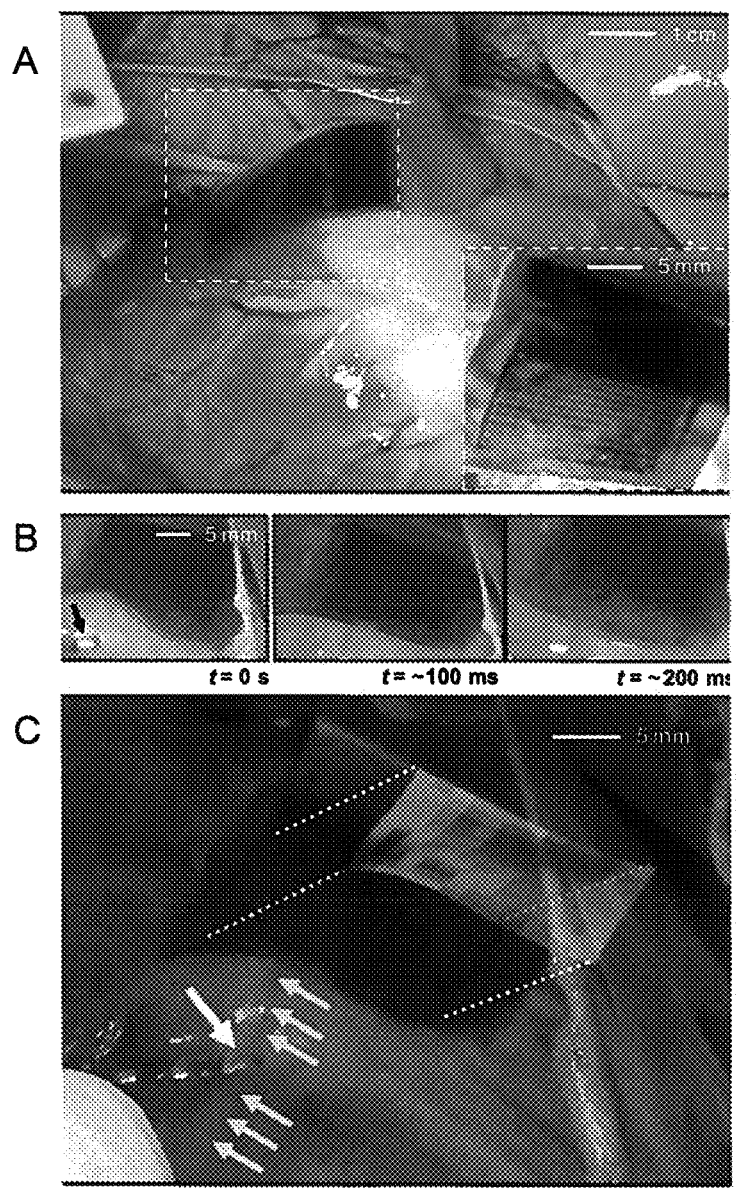
FIGS. 15A and 15B show an example device, according to the principles herein.

The performance of high density electrodes and data acquisition systems may be implemented for mapping arrhythmias spatially and temporally. FIGS. 15A and 15B show an example device according to the principles herein that includes 288 electrodes. During testing, the device is placed on the epicardial surface during normal rhythm and pacing. Unipolar voltage data are recorded from all 288 electrodes with the sampling and multiplexing strategy described above. Baseline data are collected in sinus rhythm with the array in multiple positions on the ventricles. Data is also recorded while pacing the heart. The distance of the pacing electrode from the array varies from 2 to 5 cm during preliminary experiments.

FIGS. 15A to 15C show photographs of a flexible electrophysiology mapping device according to various examples. FIG. 15A illustrates a flexible device conforming to cardiac tissue via surface tension. The inset of that FIG. 15A provides a magnified image at a different viewing angle. FIG. 15B demonstrates a sequence of movie frames collected at different times during the contraction cycle of the heart, illustrating the ability of the device to bend in a way that maintains intimate, conformal contact with the tissue during cardiac rhythm. Dotted lines highlight the degree of bending along the device. A conventional pacing electrode is indicated in the left-most frame (black arrow). FIG. 15C shows a photograph of a device on the LAD coronary artery (arrows), with overlaid color map of the relative time of depolarization.

The system illustrated in FIGS. 15A to 15C had sufficient resolution (with 288 electrodes) to detect propagation of wave fronts over approximately 1 cm$^2$ of areal coverage on the ventricles. Bipolar electrodes with a similar data acquisition architecture may be used to visually map activation during acute AF in Langendorff hearts.

Figure 16:
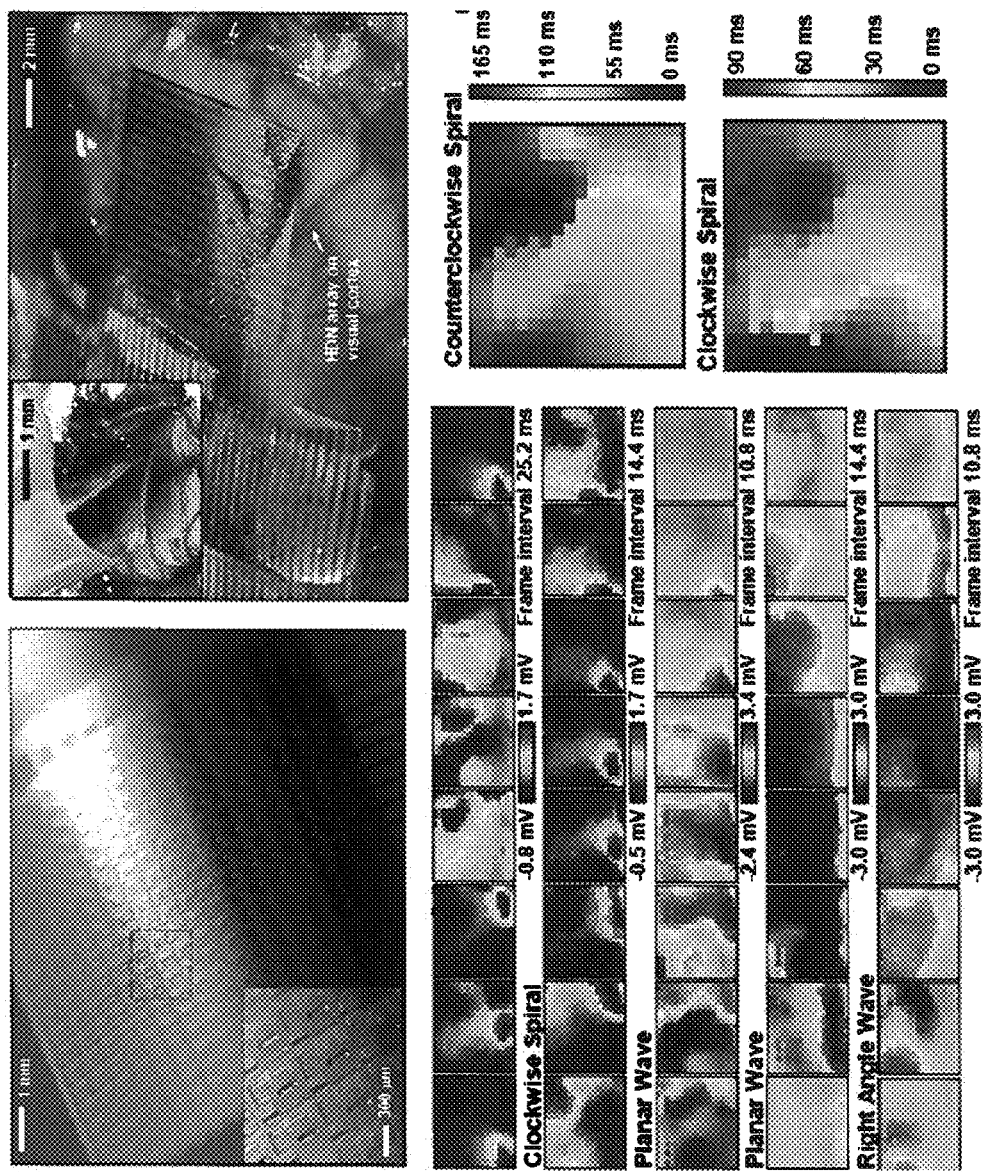
FIG. 16 illustrates flexible high-density electrode array with multiplexing circuits and measurements, according to the principles herein.

In other related preliminary measurements conducted on the live brain surface, examples demonstrate the capability to map rotors and wave fronts existent during epilepsy episodes. This work demonstrates extremely high spatio-temporal resolution, which is particularly relevant to arrhythmia mapping. FIG. 16 shows high-density sheets of active electrical circuits (approximately 360 circuits per cm$^2$) that can produce a detailed map of rotors and wave fronts on the surface of the brain (FIG. 16). Accordingly, epicardial and endocardial mapping capabilities at these high densities demonstrated by various examples described herein facilitate direct contact with the surface of the walls of the atria.

FIG. 16 illustrates flexible high-density electrode array with multiplexing circuits and measurements taken therewith in accordance with various examples. Preliminary measurements conducted on the brain, and shown in FIGS. 7c-7e, demonstrate the true capability of various examples to map electrical patterns of rotors and wave fronts with unparalleled spatio-temporal resolution. This unique capability may provide significant insight into the underlying mechanisms of AF.

Conformal sensor arrays and data acquisition consoles according to examples of the present disclosure are useable to make measurements in live ovine models with acute AF. Atrial signals may be measured during normal rhythm and acute cases of AF and where acute AF may be induced by rapid atrial pacing and the infusion of isoproterenol if needed. This strategy allows demonstrative mapping of AF in vivo and provides insight into rotor mechanism of AF. Because the left atrial anatomy is complex, different catheter designs may be implemented in various examples to map different areas of the atria. While balloon based catheters are optimal for mapping regions surrounding the pulmonary vein ostia, they may not be adequate for mapping areas along the atrial walls. As a result, catheters including deformable sheets may be used. These balloon- and sheet-based catheters may be used endocardially to evaluate mechanical and electrical performance.

Figure 17:
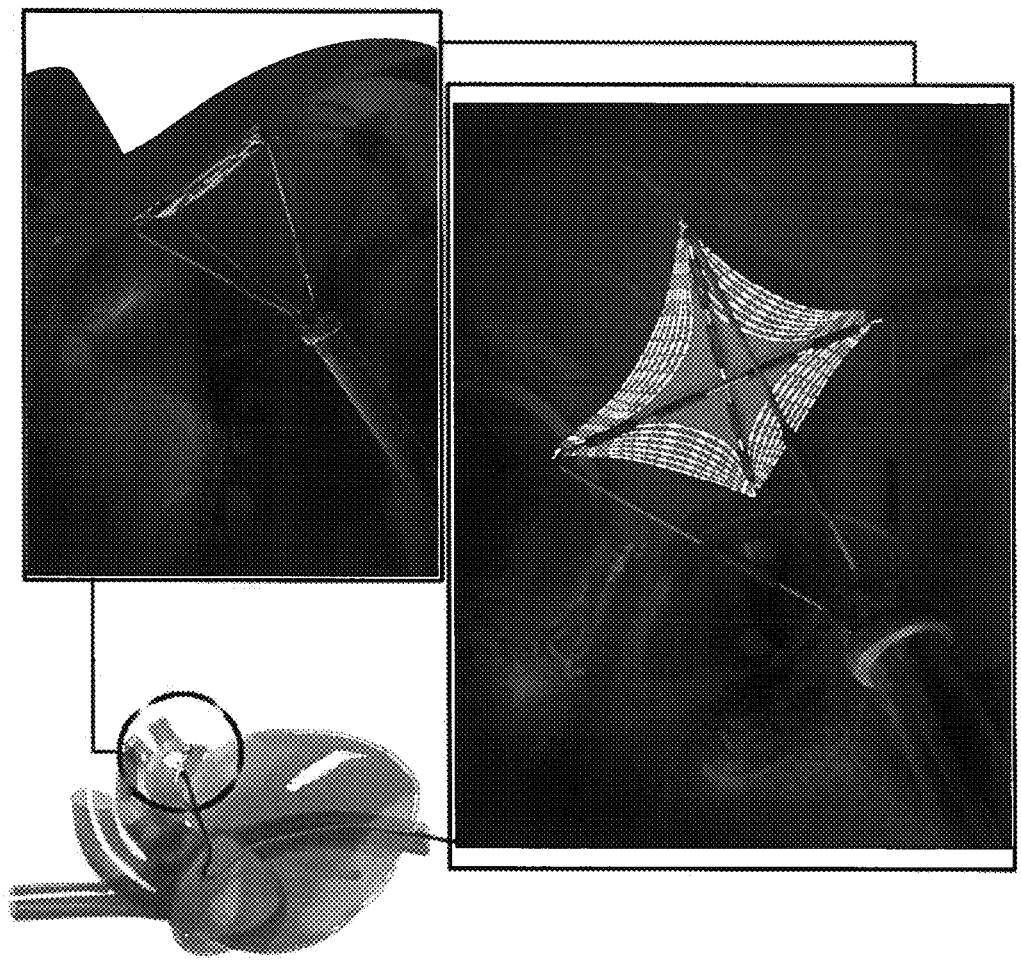
FIG. 17 shows dense arrays of conformal electrodes with metal serpentine interconnections, according to the principles herein.

FIG. 17 shows dense arrays of conformal electrodes with metal serpentine interconnections on thin polymeric sheets in accordance with various examples. Simple nitinol cage designs coupled with highly elastic sheets provide a new platform for cardiac ablation catheters (FIG. 17). At its proximal end, the catheter shown in FIG. 17 includes a simple cage attached to the catheter shaft at the proximal end and to a polymer sheet including conformal electrodes at its distal end. Metal traces and wiring can route via thin flex ribbon along the nitinol arms and converge to form a larger ribbon within the catheter shaft (approximately 10 F). The sheet can retract into the catheter shaft by folding inward so that the polymer material compresses (by 50-80%) and folds down inside the guiding sheath. Preliminary test show that sheets including conformal sensors can conform to the deformable shape of the beating heart with sufficient durability (FIG. 14) to wrap and unfurl in ways that are compatible with this catheter design. This approach provides a new way to deploy conformal sensors from the distal end of catheter systems for mapping atrial signals in areas outside of the pulmonary veins.

Figure 18:
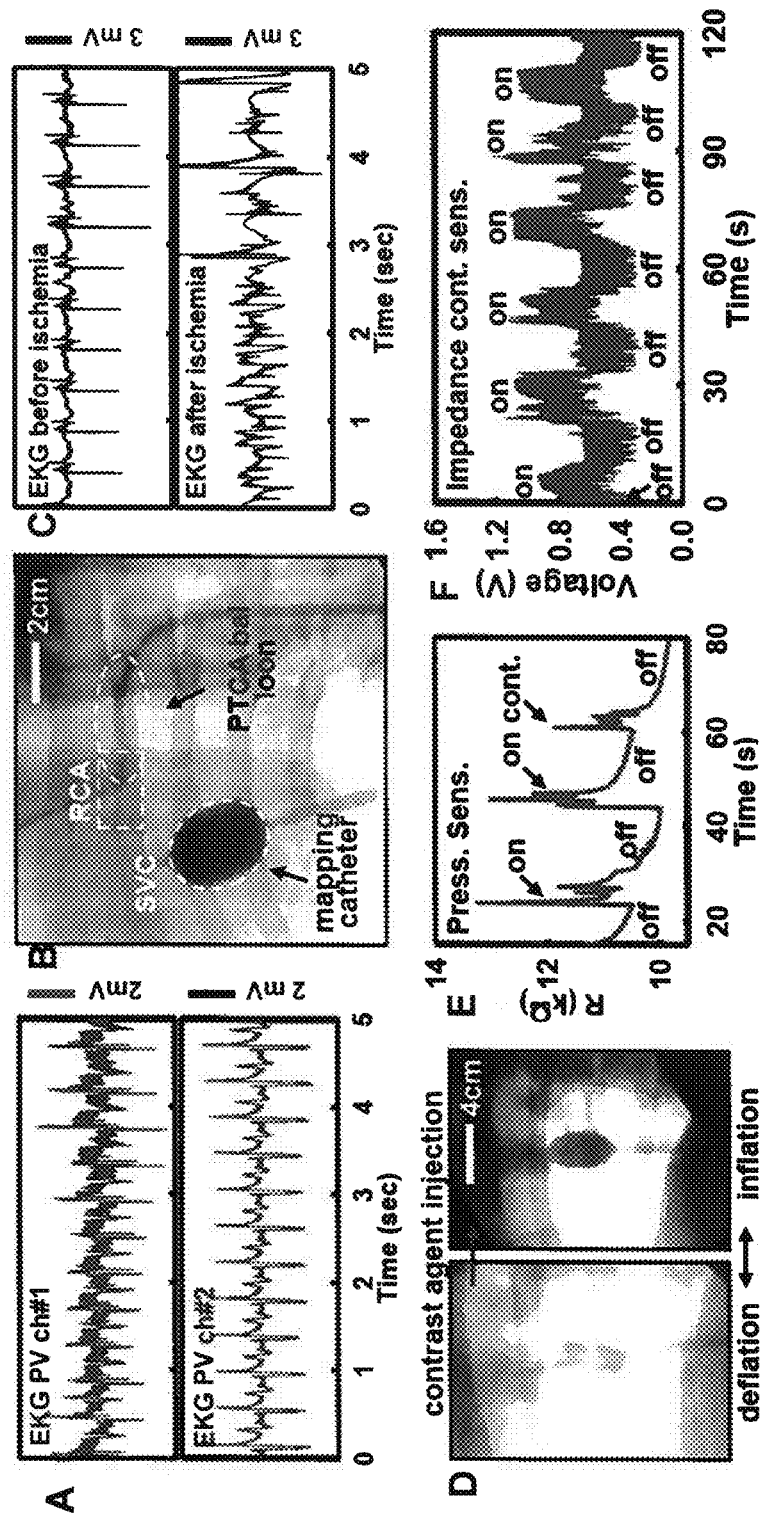
FIGS. 18A-18F show non-limiting examples of balloon catheters and measurements conducted using these catheters, according to the principles herein.

Balloon based catheters provided by illustrative examples are used for mapping the areas surrounding the ostia of the pulmonary veins. Balloon catheter designs provide a platform for heterogeneous collections of high-performance semiconductor devices and sensors. The result is a cardiac catheter that provides versatile modes of operation with high sensor densities. Non-limiting examples of balloon catheters embedded with electrodes, temperature and pressure sensors are shown in FIGS. 11 and 18A-18F. Measurements conducted with these catheters show that they can collect atrial and ventricular signals (FIGS. 18C and 18E). Catheters fitted with conformal sensors, using non-standard balloon shapes (Advanced Polymers Inc.) that conform to the atrial walls may also be implemented in various examples. The durability of these conformal sensors can be tested following deployment through sheaths and signal fidelity can be evaluated during mechanical maneuvering. Preliminary measurements using conformal electrode arrays (FIG. 18D) deployed in the right and left atria can be sufficiently durable. Flex ribbon connectors interfacing the conformal electrodes and thin wires running along the shaft provide strong adhesion to survive bending and torsional stresses.

Electrical Circuitry

Systems or apparatus are also described herein for readout of one or more multiplexed signals. The apparatus can include a flexible substrate and a plurality of active electrical circuits disposed on the substrate. The plurality of active electrical circuits are configured to transmit one or more multiplexed signals to a signal processor. In one non-limiting example, the active electrical circuit can include an electrode and a differential pair amplifier coupled to the electrode. In another non-limiting example, the active electrical circuit can include an electrode and a source-follower amplifier coupled to the electrode. According to the principles herein, the plurality of active electrical circuits are arranged on the flexible substrate in a distributed circuit arrangement such that the apparatus is conformable to a contour of a surface to be measured.

Figure 19:
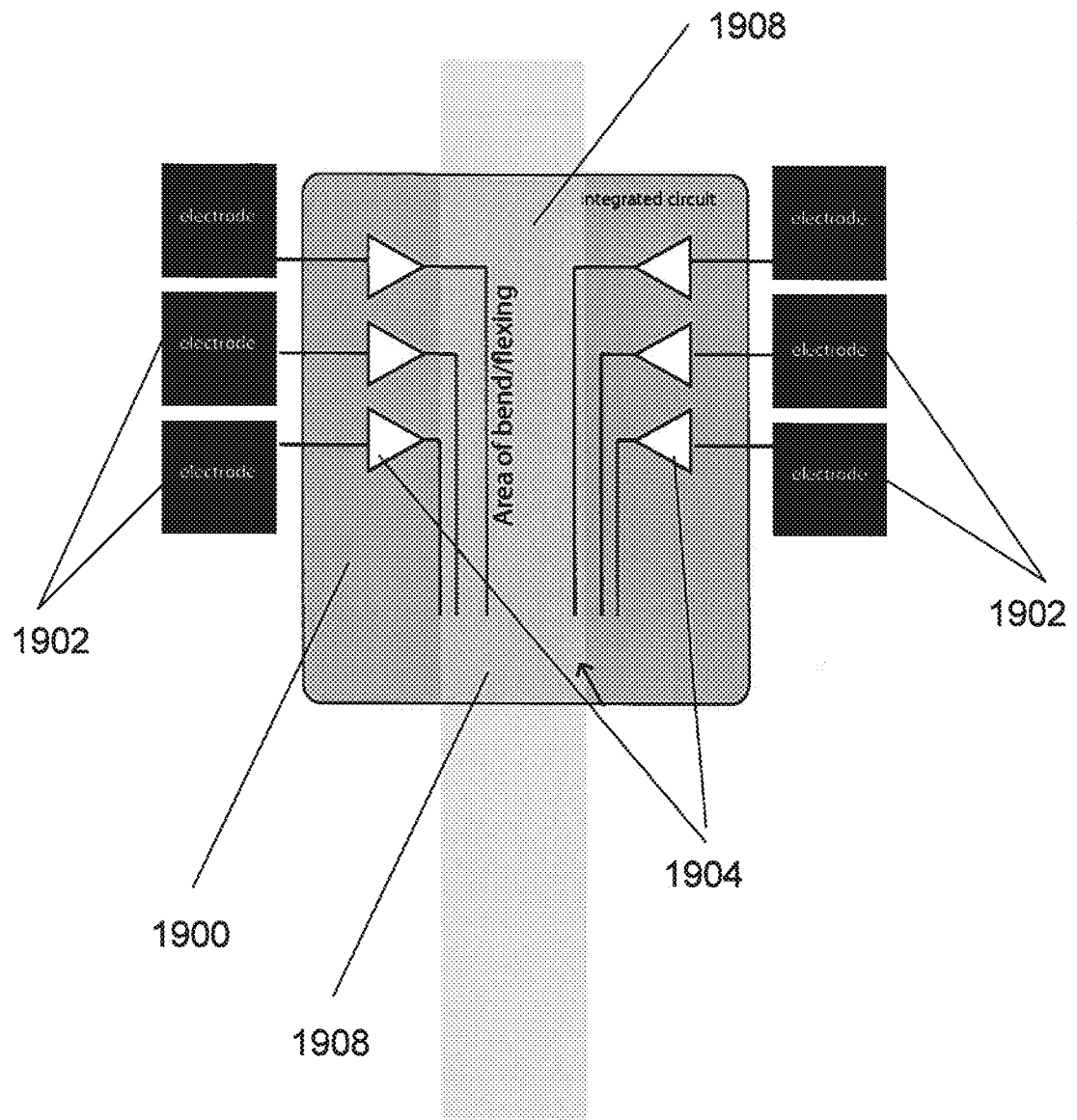
FIG. 19 shows an example arrangement of circuit elements, according to the principles herein.

FIG. 19 shows an example arrangement of circuit elements where the components are grouped over a given area. As shown in FIG. 19, the integrated circuit (IC) components 1900 that couple to the electrodes 1902 are generally grouped at a local area. For example, the circuit components can be arranged such that the local area encompasses several amplifiers. This type of arrangement has several advantages in a traditionally rigid system since it can simplify the IC fabrication processes and be cheaper to manufacture.

In an apparatus or system based on a flexible substrate flexible system, such as the systems and apparatus described herein, such a localized area arrangement presents potential points of failure for the devices. For example, there is the possibility that the local IC areas will be positioned at areas of bending and/or flexing of the substrate (see, e.g., area 1908 of FIG. 19). For example, portions of a flexible substrate of an inflatable body can be subjected to very high levels of stress and folding when the inflatable body is deflated (see, e.g., FIGS. 3A and 6D). A flexible substrate that is part of a patch, a bandage, or other similar system also can be subjected to bending, flexing or folding stresses that would not be encountered in a rigid system. These stresses can cause mechanical and/or electrical failure of the components at the local IC area if these stresses exceed a tolerance of the IC components. Such an area of failure can be catastrophic to the function to the overall electrical circuitry since, as shown in FIG. 19, several essential IC components can be damaged at once. These IC components serve several unit cells of a larger array of electrical circuits, and as a result, the functioning of large areas of the array can be disrupted, causing failure of the array of electrical circuits. Furthermore, a more traditional circuit design that integrates a large number of transistors or other circuit components in one chip, or one area of a chip, can create large areas that is not as conformal or conformable to a contour of a surface.

Figure 20:
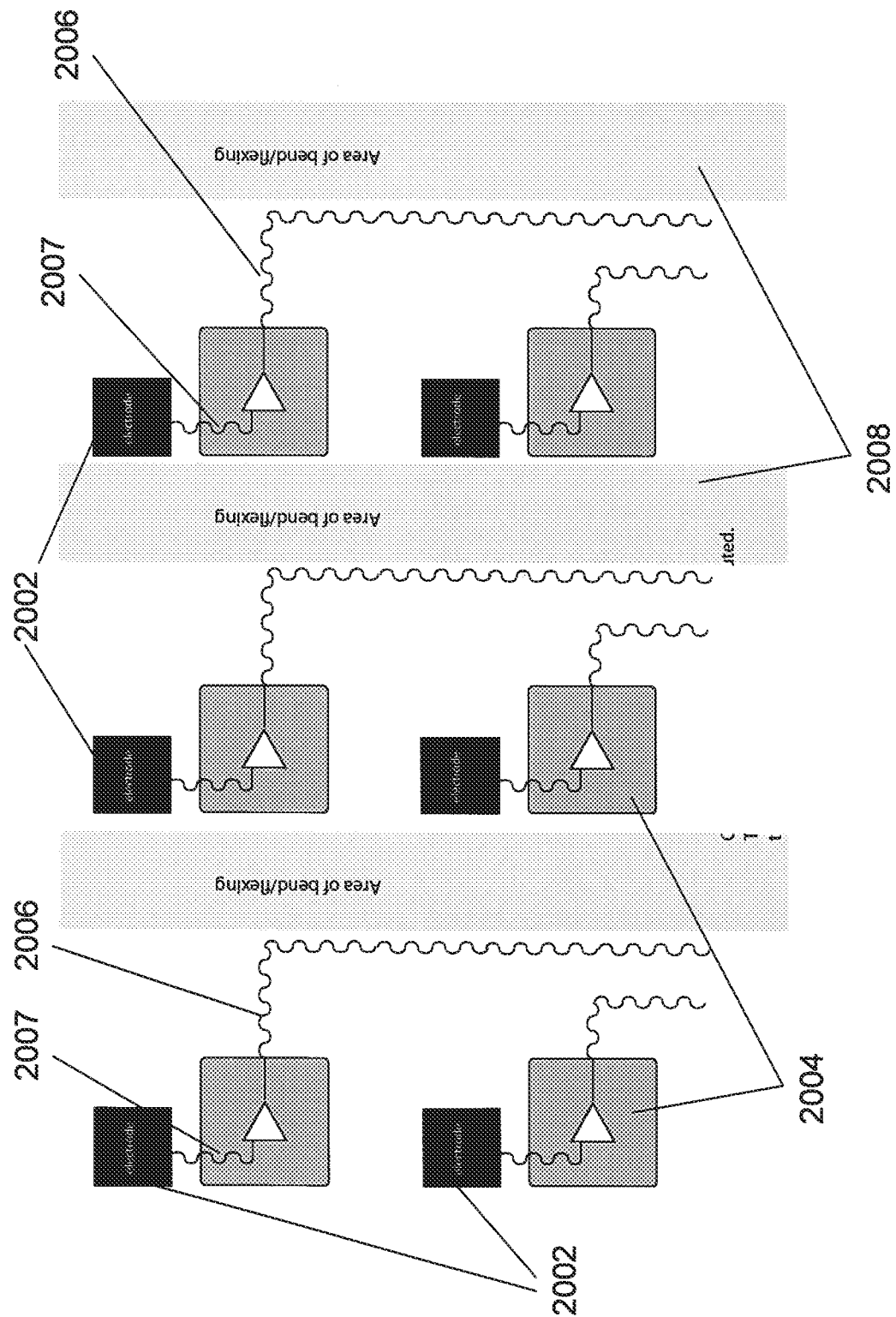
FIG. 20 illustrates a non-limiting example of a distributed arrangement of circuit elements, according to the principles herein.

According to the systems and methods described herein, the active electrical circuits are arranged in a distributed arrangement of circuit elements, in a web or mesh of circuit components. FIG. 20 illustrates a non-limiting example of a distributed arrangement of circuit elements. The electrodes 2002 are distributed across an area of a flexible substrate. IC components of the apparatus or system are also distributed. For example, the amplifiers 2004 are distributed across the flexible substrate. The system or apparatus also includes multiple interconnects (as described herein), such as interconnects 2006 that couple the IC components to other components (such as the signal processor), or interconnects 2007 that couple the electrodes 2002 (or other similar component of a sensing element) to the IC components 2004. These interconnects are illustrated, as non-limiting examples, as components 1204 of FIG. 12 or the intermediate bus of FIGS. 4, 5B and 6A.

As shown in FIG. 20, the distributed arrangement of circuit elements provides an apparatus or system that can be positioned on a flexible substrate such that there is significantly less risk that the more delicate components fall at areas 2008 of higher bending or flexing stress of the flexible substrate. The distributed arrangement of circuit elements provide a web or mesh of circuit components that support a more conformal apparatus or system that is conformable to a contour of a surface to be measured. The distributed arrangement of circuit elements described herein breaks up the overall circuit into islands separated by interconnects, such as but not limited to the serpentine interconnects. This can cause the conformal system to be more resilient to bending and/of flexing stresses. The distributed arrangement affords more flexibility by allowing the separation of the circuit islands. The distributed circuit elements can be positioned selectively and strategically at low stress areas of the flexible substrate to improve reliability. That is, the distributed arrangement allows for strategic placement of circuit islands and interconnects to be positioned on the flexible substrate outside of higher-stress/higher-flex areas.

In addition, the distributed arrangement of circuit elements described herein can be more resilient to failures in any one or more region. Damage to a single cell in the distributed arrangement of circuit elements may result in a row and column readout of a given cell to fail, but the remaining cells of the array of the distributed arrangement of circuit elements can continue to operate normally.

Components of the distributed arrangement of circuit elements are described as follows. The distributed arrangement of circuit elements can be used with any array of sensing elements, including arrays where the sensing elements and/or the active electrical circuits include the electrodes described below. For example, the distributed arrangement of circuit elements can be positioned in the region of the plurality of sensing elements and the at least one intermediate bus, according to the principles herein and as described in connection with any of FIGS. 4 through 8. As another example, the distributed arrangement of circuit elements can be positioned in the region of the plurality of active electrical circuits and the at least one conductive flexible interconnection, according to the principles herein and as described in connection with any of FIGS. 11 through 13. Furthermore, the readout of the one or more multiplexed signals from the circuit components described hereinbelow can be used to obtain readings from the sensing elements and active electrical circuits described herein above.

Figure 21:
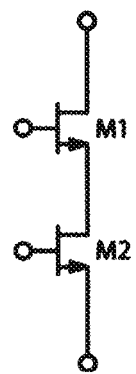
FIG. 21 depicts an example active electrical circuit, according to the principles herein.

FIG. 21 depicts an active electrical circuit implemented according to principles described herein. This circuit, which may be utilized in neural flexible electronic applications, includes a source follower with a pass-through transistor for multiplexing as shown in FIG. 1.

Figure 22:
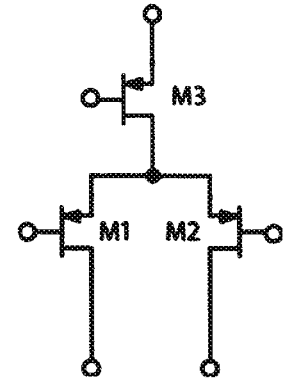
FIG. 22 illustrates another example active electrical circuit, according to the principles herein.

FIG. 22 illustrates another active electrical circuit implemented according to principles described herein. In this non-limiting example, the circuit is illustrated as including a positive or p-type metal oxide semiconductor (PMOS) differential pair amplifier with a tail. This circuit also may be utilized in neural flexible electronic applications. In some examples, the tail is a transistor functioning as a current mirror.

Figure 23:
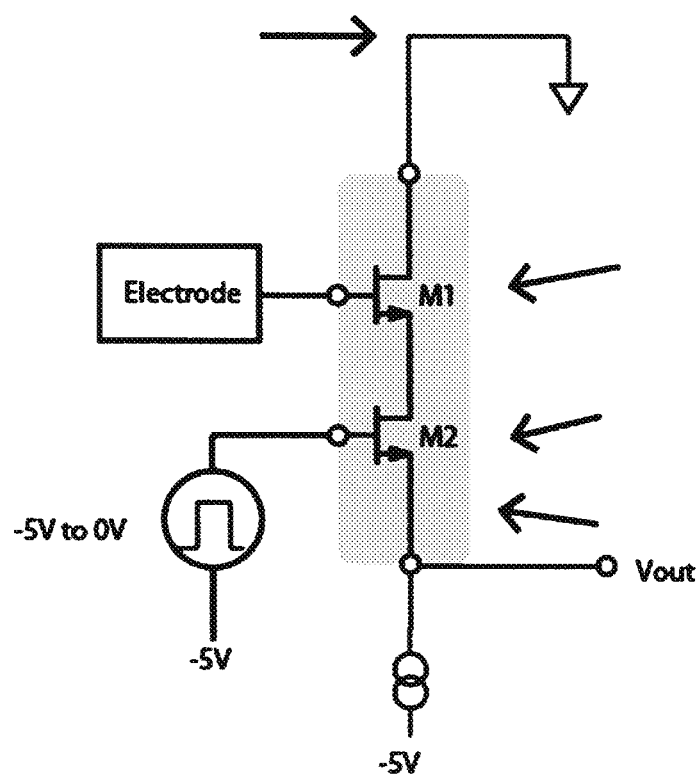
FIG. 23 demonstrates the characteristics of the active electrical circuit shown in FIG. 21, according to the principles herein.

FIG. 23 demonstrates the characteristics of the active electrical circuit shown in FIG. 21. The active electrical circuit of FIG. 21 buffers the electrode input signal and passes that to the output. Provided transistor M1 is sized and biased properly, gain is approximately 1. Multiplexing transistor, M2, serves as a pass-through transistor. In operation, M2 is turned on hard, allowing the signal at the source of M1 to pass through to the output, $V_{out}$. Accordingly, M2 acts as a switch allowing the signal to pass to $V_{out}$. The drain of M1 drain is tied to ground to help prevent the circuit from leaking current. In a medical application, such a current could be leaked into a patient, for example, if the circuit in comes in contact with, e.g., leaked saline (even if the circuit is in encapsulated form). Configuring the circuit so that the drain of M1 is tied or biased to ground can minimize the potential difference between a surface upon which the flexible substrate and electrical circuits are disposed. In non-limiting examples, the surface can be the brain, the heart, or other internal or external body surface.

In some examples, the area of the input transistor, M1, may be maximized and the gate width to length ratio (W/L) of M1 may be increased to reduce noise.

Figure 24:
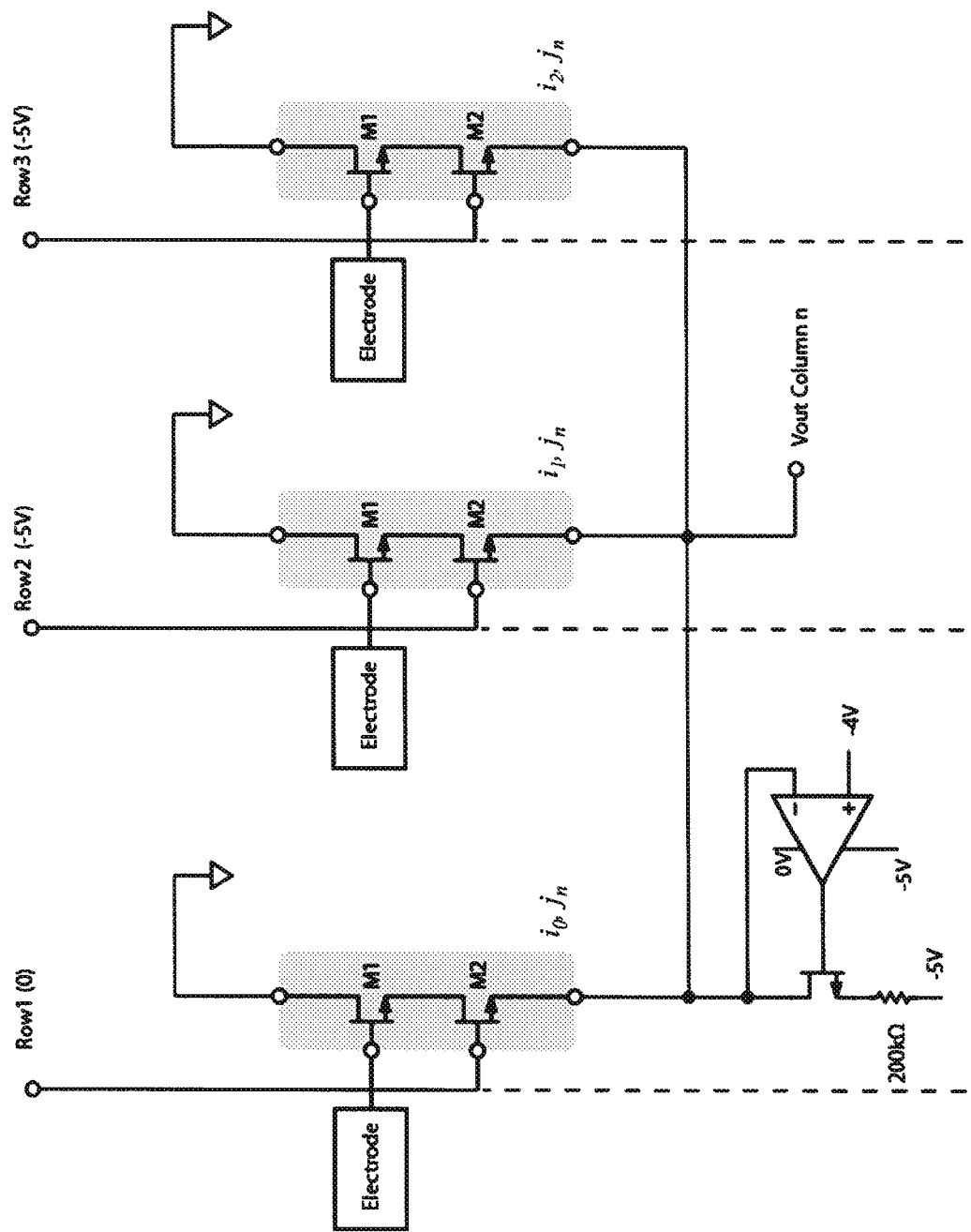
FIGS. 24 and 25 illustrates a plurality of example active electrical circuits, according to the principles herein.
Figure 25:
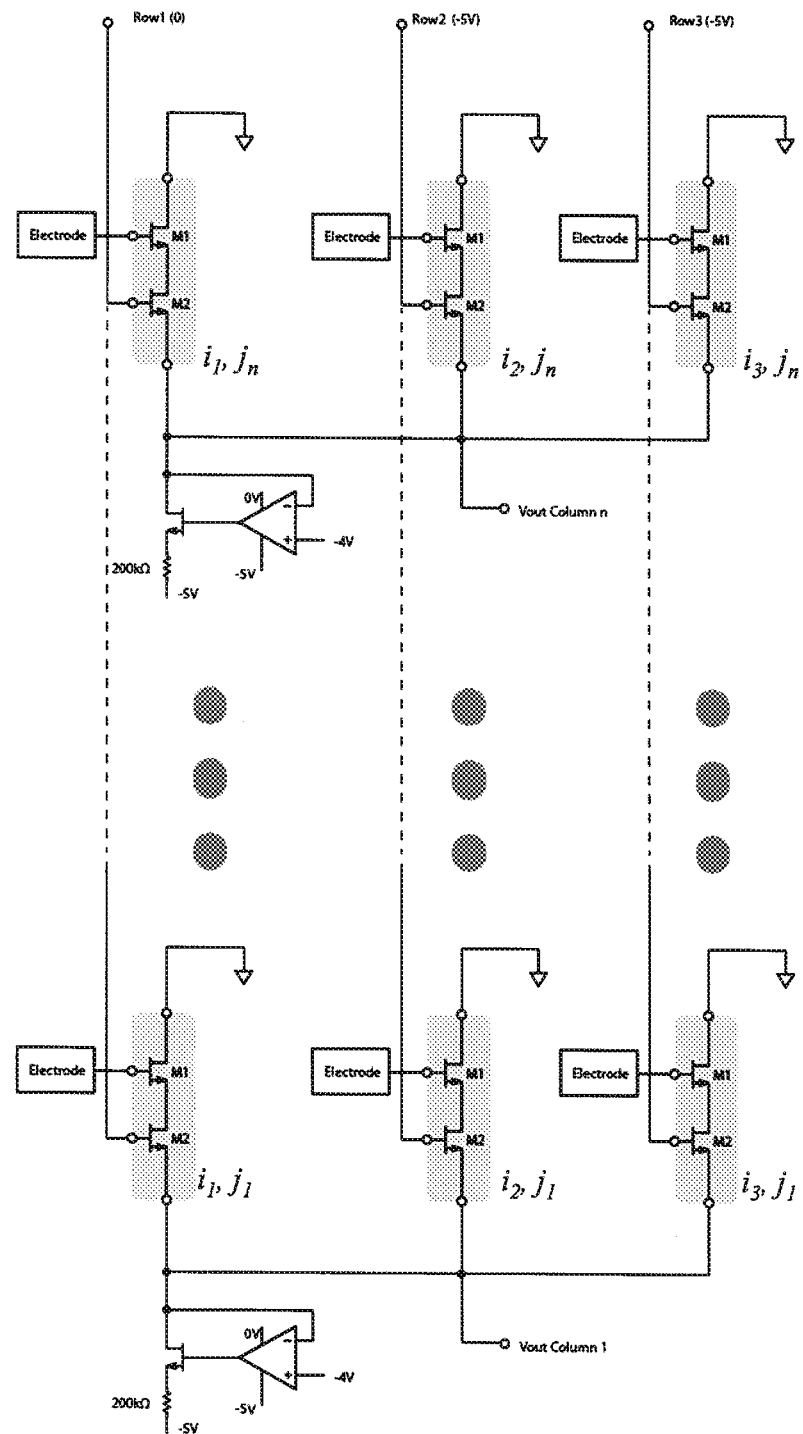

FIGS. 24 and 25 illustrates a plurality of active electrical circuits of FIG. 21 electrically coupled in accordance with principles described herein. The array illustrated in FIGS. 24 and 25 include m rows ($i_1, \ldots, i_m$) and n columns ($j_1, \ldots, j_n$). In an example implementation, all n columns are read simultaneously. In this example, only one row is active at a time so when the data acquisition system reads the outputs of each column, only data from that row is sent. One row is switched on at a time; all the outputs from a column are read simultaneously. The illustration in FIGS. 24 and 25 show row 1 activated (ON) and all the other rows not activated (OFF). Thus, the n electrodes from row 1 are read simultaneously. The total number of exposed ports for a plurality of circuits configured as demonstrated in FIGS. 24 and 25 (in a n rows by m columns configuration), is one more (for a single source power supply) than the sum of the number of rows plus the number of columns/outputs.

TABLE 1

The number of exposed ports for an m × n array.

| Port Name | Number |
| --- | --- |
| Positive Supply | 1 |
| Row Control | N |
| Output | M |
| Total Number of Ports | 1 + n + m |

As indicated above, the active electrical circuit of FIG. 21 is configured as a follower followed by a pass-through switch that serves as a multiplexer. The voltage at the gate determines the source of the input transistor, M1. Accordingly, the electrode voltage determines the voltage at the source. A constant current serves as the load and provides the drain current for both the input transistor and pass-through transistor, M2. Using Equation 1 shown below, the gate-source voltage, Vgs, for M1 and M2 may be calculated.

Gate-source voltage equation  Equation 1

$$V_{gs} = \sqrt{I_d \frac{L}{W} \frac{2}{\mu_n C_{ox}}} + V_{th}.$$

Figure 26:
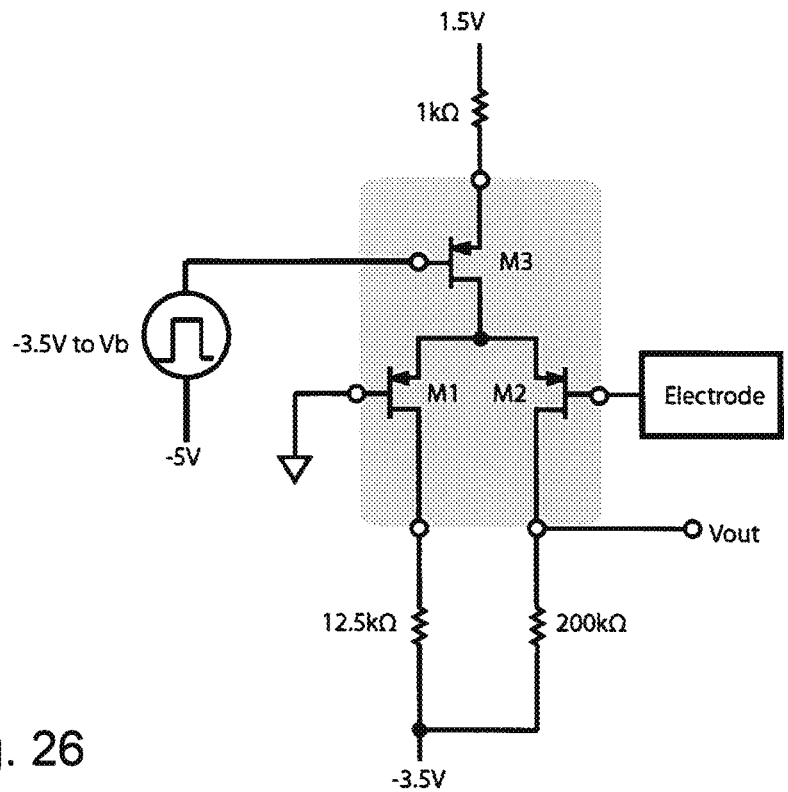
FIGS. 26 and 27 illustrate the characteristics of example active electrical circuits, according to the principles herein.
Figure 27:
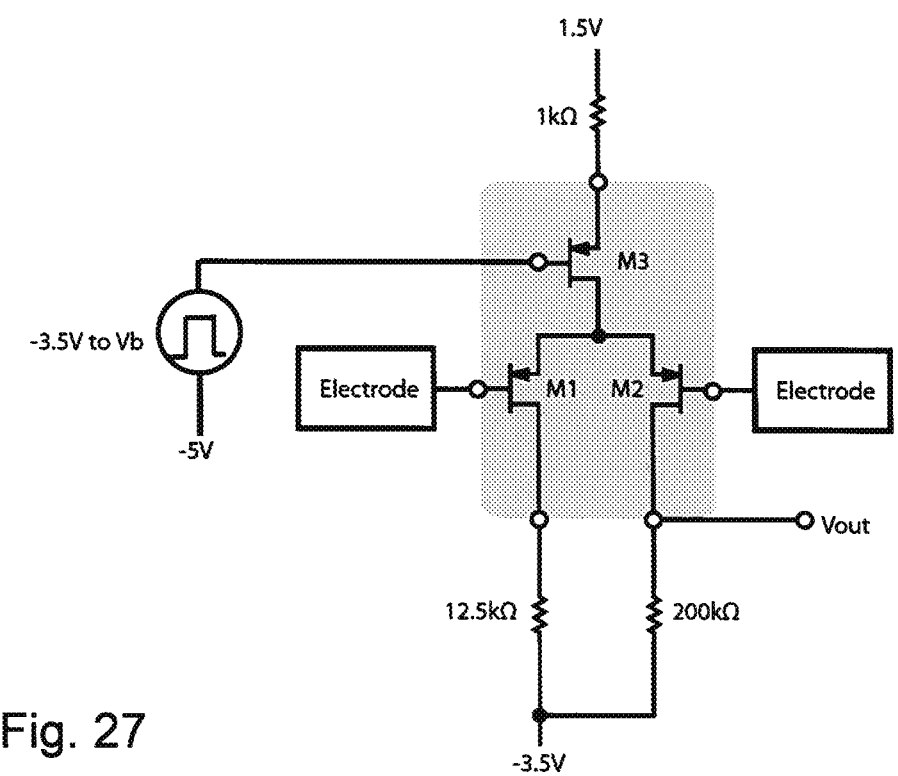

FIGS. 26 and 27 illustrate the characteristics of the active electrical circuit shown in FIG. 22 in a single-ended connection (FIG. 26) and in a differential connection (FIG. 27). As noted above, the active electrical circuit illustrated in FIGS. 21, 23 and 24 are in the source follower configuration. The circuit configuration of FIGS. 22, 26 and 27 gains a differential signal and helps to reject noise. If $g_m R_s$ dominates the functional form of Equation 2, then the gain may be slightly less than 1. In the illustrated example, $R_s$ is based on M1, and the load created from the active load is in series with the resistance of M2. The gain of the voltage follower in the configuration demonstrated in FIGS. 21 and 22 may be calculated using Equation 2.

Gate of voltage-follower  Equation 2

$$A_v = \frac{g_m R_s}{1 + (g_m + g_{mb})R_s}.$$

Since the transistors used can have a large W/L to reduce noise in some examples, a low current (for example 10 μA) may be used to run the devices at sub-threshold levels. Accordingly, the $g_m$ may be calculated using the weak-inversion formula given by Equation 3:

calculation of $g_m$ in weak-inversion  Equation 3

$$gm_{weak-inversion} = \frac{I_d}{nV_t}$$
$$n = 1.5 \text{ to } 2;$$
$$V_t = \frac{kT}{q} \approx 26 \text{ mV}.$$

The active electrical circuit of FIGS. 22, 26 and 27 achieves gain using a different procedure than that of the circuits of FIGS. 21, 23 and 24. The active electrical circuit of FIGS. 22, 26 and 27 gains the signal, boosting the magnitude of the signal while reducing the effect of noise due to M1 and M2. In addition, the circuit of FIGS. 22, 26 and 27 conditions the signal differently from the circuit of FIGS. 1 and 3, by using a differential-pair configuration. The circuit of FIG. 26 compares the signal on the associated electrode with ground and gains that difference. The potential of the underlying contact surface (for example the surface of the brain tissue) is at ground, so the differential-pair is effectively only gaining the relevant signal. More importantly, differential signal processing allows for better rejection of noise. Noise that is picked up on both gates of M1 and M2 is rejected. The circuit of FIG. 27 compares the signal on one associated electrode with the signal on the other associated electrode, and any noise identified based on the comparison is rejected. Additionally, noise at the drain of M3 is also rejected. To avoid the saline leakage problem mentioned above, if and when the encapsulation layer breaks, current limiting resistors, for example resistors having 1 kΩ and 12.5 kΩ, may be positioned in the circuit line. The size of this resistor may be dictated by the amount of common-mode headroom required. The current limiting resistor, $R_D$, may be shared among multiple differential pairs. If, for example, the current limiting resister, $R_D$, were shared amongst 16 differential-pairs, $R_D$ would have 16*Id/2 current flowing through it and may be sized based on this required current capacity. In medical applications, this current is maintained at 10 μA or less. While not shown, the gate of M3 is driven by a current-mirror. The mirror drives all the corresponding M3 gates in that array's row. To multiplex that row, the current mirror may be biased on or off. When it is biased off, a pull-up resistor is switched in to pull the gate of M3 high and the differential-pair collapses. Stated differently, when the mirror is turned off, the unit cell turns off.

Figure 28:
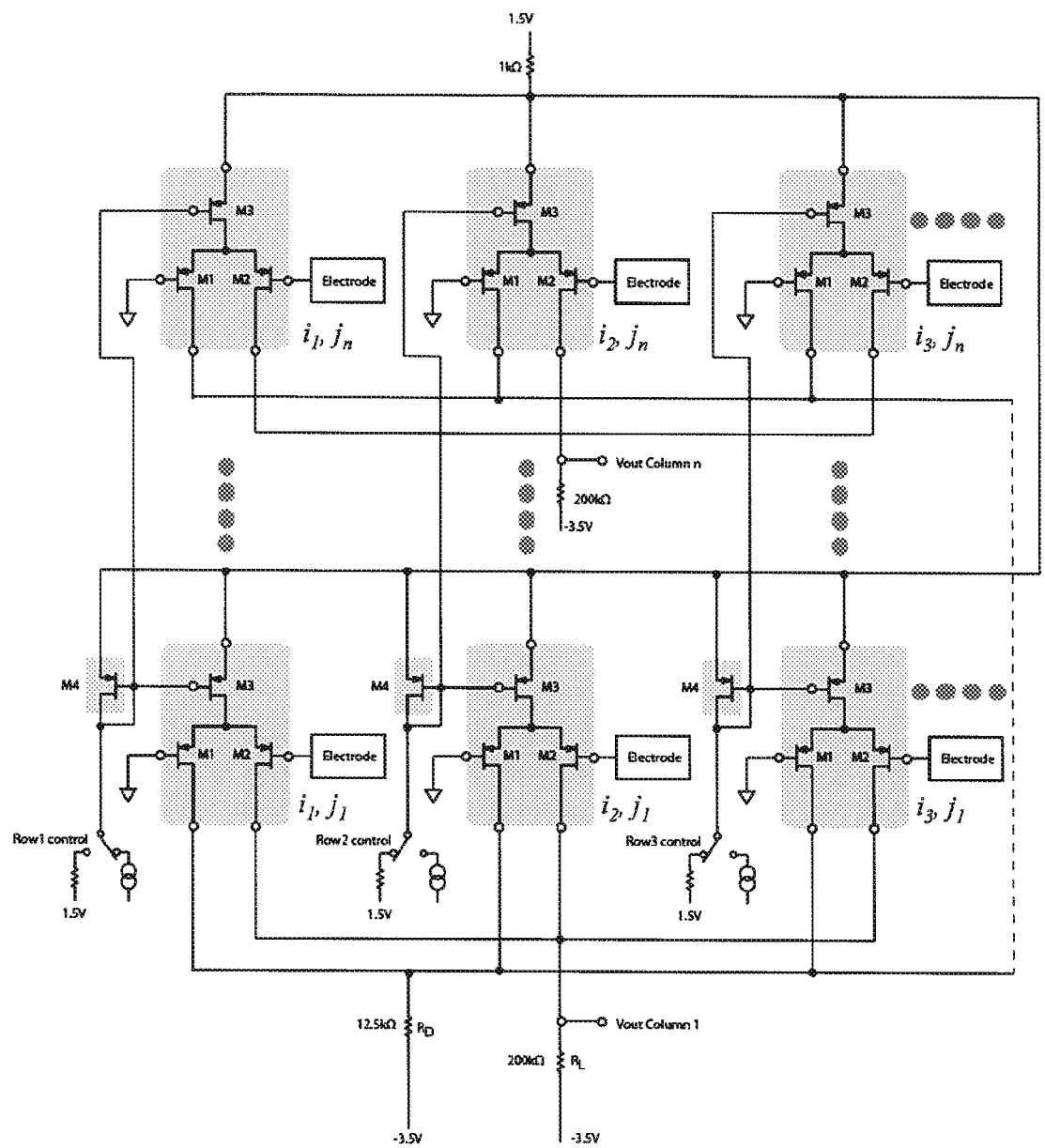
FIG. 28 illustrates a plurality of example active electrical circuits, according to the principles herein.

FIG. 28 illustrates a plurality of active electrical circuits of FIGS. 22 and 26 electrically coupled in accordance with principles described herein. All columns are read simultaneously. In this example, only one row is activated to ON at a time. In the example illustrated in FIG. 6, Row1 is activated to ON, and all the electrodes in row 1 are being read simultaneously. Data is output through $V_{out}$ Column 1 to Column n. Similar to circuit arrays shown in FIGS. 24 and 25, the arrays shown in FIG. 28 may include an m by n array of amplifiers [m rows ($i_1, \ldots, i_m$) and n columns ($j_1, \ldots, j_n$)]. In an example, one row is on at any given time and data is read from that row simultaneously. In FIG. 28, row 1 is on. Each column shares one output node but since only row 1 is active, an output node of a column delivers signal from only row 1.

The multiplexing mechanism of the configuration shown in FIG. 28 differs from the configuration shown in FIG. 25 in that the row control switch either draws current, for example 10 μA of current, to bias the current-mirror (at M4), thereby activating the neural amplifier, or the row control switch pulls the gates of M3 and M4 high to turn off the respective amplifier.

To keep the number of input output I/O ports at a minimum, $R_D$ may be shared amongst all the drains of M1. In examples where the signal is conditioned and measured only at the drain of M2, the current path at the drain of M1 may be shared, provided that M1 is biased properly. $R_D$ is sized to generate the same quiescent voltage at the drain of M2 as $R_L$ generates at the drain of M3—providing a balanced differential pair. While the drain of M2 is not very sensitive to variations in voltage at the drain, an effort is made to keep symmetry. There is one resistive load, $R_L$, at each column but they are shared across each row. For an m×n array, there are n number of $R_L$s. The n loads help to generate the gain for the n output channels. All sources of M3 share a positive supply port. A current limiting resistor limits the current flowing through the supply. In an example, only one row is active at a time so the limiting resistor will typically have Id*16 flowing through it. Each row of active electrical circuit configuration shown in FIG. 28 has a current-mirror bias transistor (M4) that forms a current-mirror with all the M3s in a given row. All the mirrors share one positive supply port. The drain of the current-mirror is exposed and is used to control the current through the mirror and to switch off a row. The total number of exposed ports required for a plurality of circuits configured as demonstrated in FIG. 28 (i.e., in a n rows by m columns configuration), is two more (for a single source power supply) than the sum of the number of rows plus the number of columns/outputs, as further described in Table 2 below. For example, there are 34 exposed ports for a 16 row by 16 column system configured as shown in FIG. 28.

TABLE 2

The number of exposed ports for an m × n Active electrical circuit Design.

| Port Name | Number |
| --- | --- |
| Positive Supply | 1 |
| Row Control | N |
| $R_L$ (Output) | M |
| $R_D$ | 1 |
| Total Number of Ports | 1 + n + m + 1 |

A reference current and the voltage at the gates of M1 and M2 determine the operation of the differential-pair/amplifier. As previously mentioned, each row has a current-mirror that determines the bias voltage levels for that row's amplifier. Ten micro-amps current drawn through M4 creates a Vgs that is applied to the gate of M3. As shown in Equation 4, Vgs is a function of $I_d$.

By setting $I_d$, Vgs of M4 is determined, all other terms are defined $$V_{gs} = \sqrt{\left|-I_d \frac{L}{W} \frac{2}{\mu_p C_{ox}}\right|} + V_{th}.$$

Equation 4

The values of W, L, $\mu_p$, $C_{ox}$, $V_{th}$ can be found in Tables 3, 4 and 5 below. Sizing of W and L are described below in connection with noise and matching.

TABLE 3

Process Parameters and Transistor Sizing

| | Constants | |
| --- | --- | --- |
| k (Boltzmann's constant) | 1.38E−23 | J/K |
| T | 300 | K |
| K | 1.00E−25 | V²F |
| n (subthreshold slope factor*) | 2 | |

*typically between 1.5-2. It is also equal to 1 + $C_d/C_{ox}$; however, n = 2 is used to better match the simulation results

TABLE 4

Neural Array #1

| M1 W/L PMOS | 300/2 | µm/µm |
| --- | --- | --- |
| M2 W/L PMOS | 120/0.6 | µm/µm |
| $\mu_p$ | 145 | cm²/(Vs) |
| $C_{ox}$ | 2.76 | fF/µm² |
| $V_{th}$ | 0.95 | V |

TABLE 5

Neural Array #2

| M1 W/L PMOS | 300/2 | µm/µm |
| --- | --- | --- |
| M2 W/L PMOS | 300/2 | µm/µm |
| M3 W/L PMOS | 48/0.8 | µm/µm |
| $\mu_p$ | 145 | cm²/(Vs) |
| $C_{ox}$ | 2.76 | fF/µm² |
| $V_{th}$ | 0.95 | V |

Figure 29:
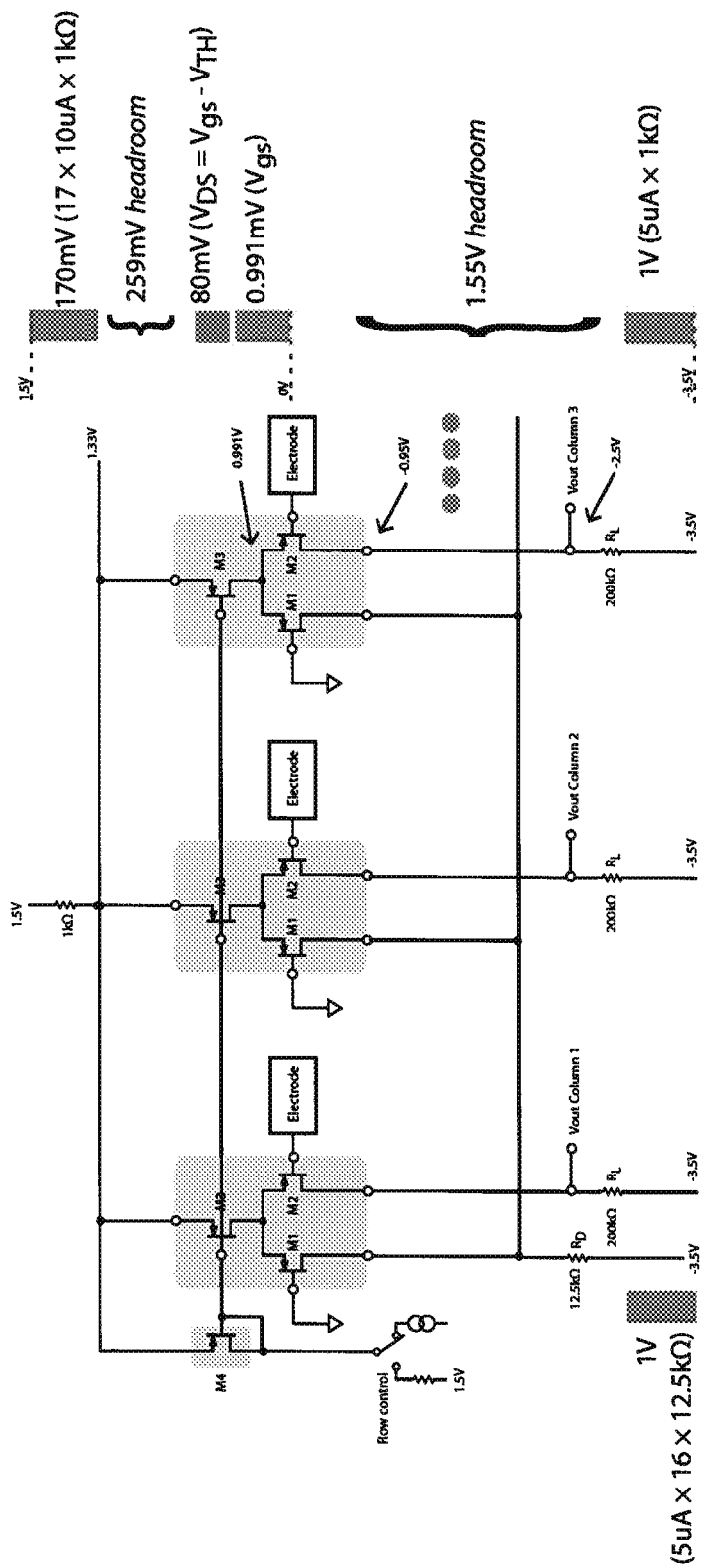
FIG. 29 illustrates an example DC operating points for a plurality of coupled active electrical circuits, according to the principles herein.

FIG. 29 illustrates the DC operating points for a plurality of coupled active electrical circuits of FIG. 22 in accordance with principles described herein. FIG. 29 demonstrates $I_d$ set at 10 µA for a medical application, because that is the maximum allowable leakage current under IEC60601 guidelines. In some examples, the leakage limit of the entire system may be set to 10 µA.

Using Equation 4, it is seen that a 1.04V Vgs is generated across M4's gate and source. Similarly, M3 sees the same 1.04V Vgs and, thus, a 10 µA current Id is delivered via M3 into M1 and M2. The 10 µA is sourced via the positive supply, through a 1 kΩ current-limiting resistor. Since one current source plus 16 differential-pairs pull 10 µA through that 1 kΩ resistor, a voltage drop of 170 mV is seen.

A Vgs of M1 and M2 of 0.991 V rides on the respective gate voltages of M1 and M2. This means that if the common-mode voltage at the gates of M1 and M2 rise, the source of M1 and M2 also rises. Enough headroom is left so that common-mode voltage swings do not saturate M1, M2 and M3. As shown in FIG. 29, the positive supply is set to 1.5V. Between the 80 mV from M3's Vgs-Vth and the 170 mV across the current limiting resistor at the positive supply, leaving with 259 mV of headroom, which is more than adequate for common-mode fluctuations and the intracranial EEG signals (10-20 mV) expected.

On the negative swing, there is 1.55V of headroom when using a −3.5V negative supply. With this negative, headroom swing gain is applied so headroom and the amount of voltage across $R_L$ determines the upper-limit of the gain applied. Using these values, a 1V output swing is the maximum swing (neglecting offset).

A system or apparatus that includes a distributed arrangement according to the principles of the active electrical circuit of FIGS. 22, 26 and 27 can be operated with reduced noise. Since electroencephalography (EEG) is measured over 0.5 Hz to 500 Hz, and possibly up to 1 kHz, the dominant noise is characterized as 1/f. To reduce the noise, the area of input transistors M1 and M2 may be increased. In one example, the area of the transistors can be increased by making W=300 um and L=2 um. As shown in Equation 26, which is an approximation of flicker noise, a 4 fold increase in area results in a 2 fold reduction in noise.

Figure 30:
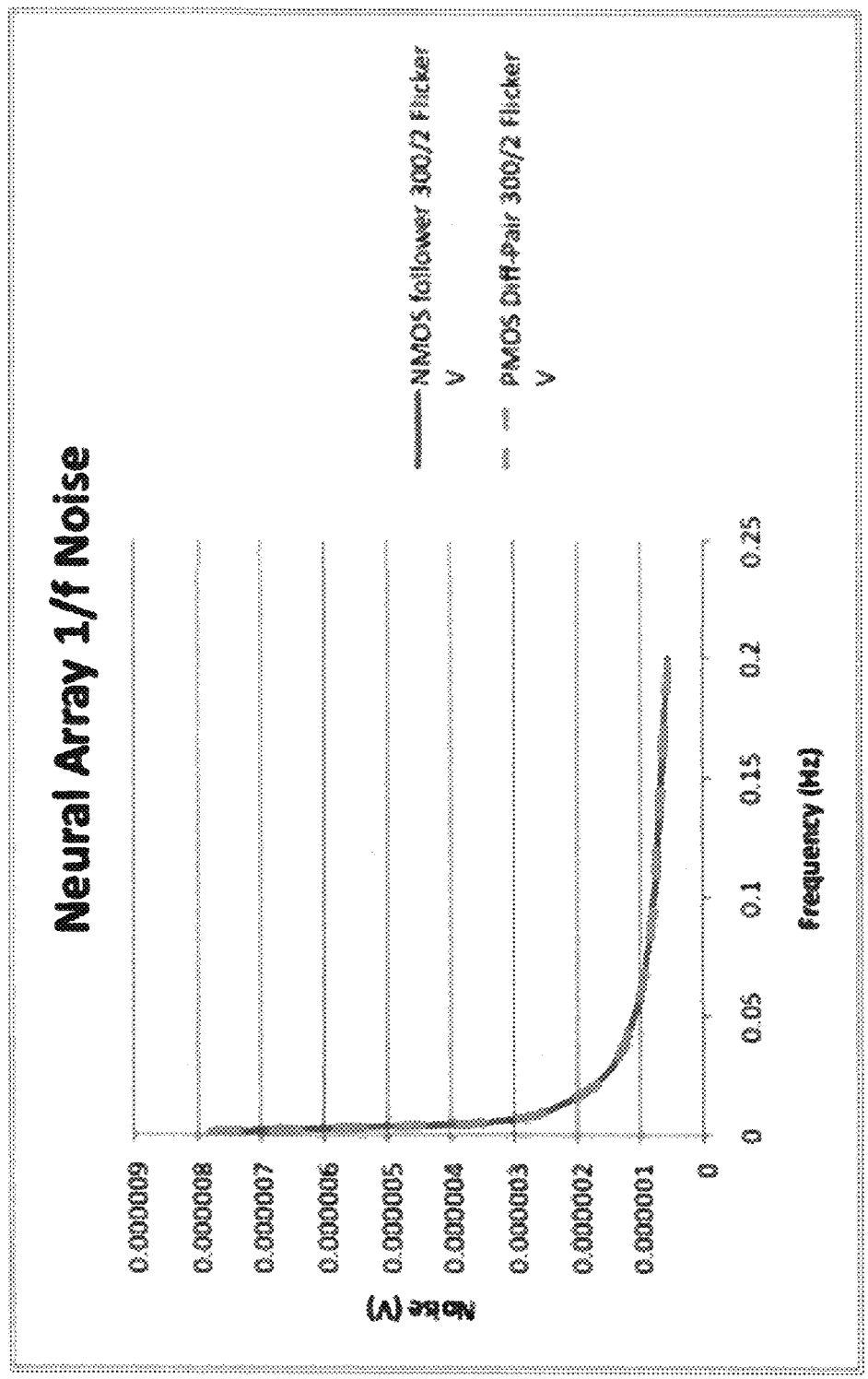
FIG. 30 is a graph illustrating the properties of transistors, according to the principles herein.

FIG. 30 is a graph illustrating the relationship between flicker noise, described as 1/f, and frequency for negative and positive metal oxide semiconductors (NMOS and PMOS respectively) implemented in accordance with principles described herein. While Equation 5 does not distinguish between NMOS and PMOS, PMOS may be characterized by exhibiting less 1/f noise since PMOS carries holes in a "buried channel." Examples according to the principles described herein may use PMOS input transistors to take advantage of the lower 1/f noise.

Approximation of flicker noise; Equation 5
it is dominated by the area of the transistor $$V_{Flicker} = \sqrt{\frac{K}{C_{ox}WL}\frac{1}{f}}.$$

In some examples, the ratio of W/L may be made large to increase transconductance, gm, as expressed in Equation 6. A large transconductance reduces thermal noise density in the differential-pair, as expressed in Equation 7. The thermal noise over 500 Hz is 180 nV.

General transconductance expression Equation 6

$$g_m = \mu_p C_{ox} \frac{W}{L}(V_{gs} - V_{th}).$$

Thermal noise density, normalized to 1 Hz, Equation 7
can be reduced by increasing transconductance
(and gain, gm² $R_D$)

$$V_{Diff-Pair\ Thermal} = \sqrt{8kT\left(\frac{2}{3g_m} + \frac{1}{g_m^2 R_D}\right)}$$

Electroencephalograph (EEG) signals are small and the contribution of noise from the instrument degrades the signal to noise. Applying gain at the input increases the size of the signal and reduces the affect of noise that is injected later in the signal chain, thus it is advantageous to apply gain early in the EEG measurement.

An example measurement of a single-ended output is described. The gain is defined by:

Gain of differential-pair with single-ended output. Equation 8
$R_L$ is a resistive load $$A_v = \frac{gm_2(r_o||R_L)}{2}.$$

Figure 31:
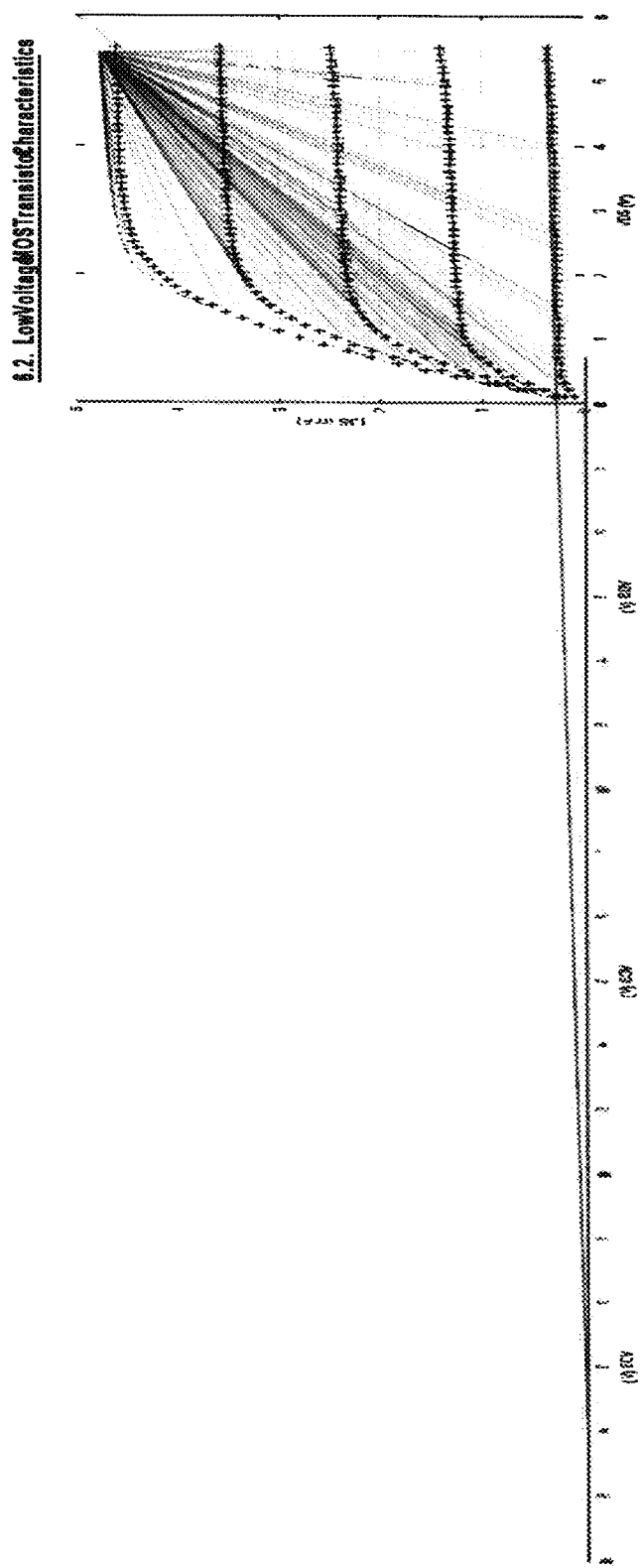
FIG. 31 shows a current-voltage curves, according to the principles herein.

M1 and M2 may be large in some examples. For example M1 and M2 may be characterized by W/L=300 um/2 um. With a small current such as 5 µA (10 µA/2) flowing through M1 and M2 respectively, the circuits are running at a sub-threshold level. In this sub-threshold level gm is modeled by equation 10, which under the current exemplary parameters provides a gm of 96.7 uA/V. If inversion were strong, Equation 9 may be used to determine the gain. Equation 10 may also be used to calculate ro or ro may be estimated from the IV curve of M2 as demonstrated in FIG. 31.

gm in stronger-inversion Equation 9

$$g_m = \mu_p C_{ox} \frac{W}{L}(V_{gs} - V_{th})$$

$$g_m = \sqrt{2\mu_n C_{ox} \frac{W}{L} I_d}$$

$$g_m = \frac{2I_d}{V_{gs} - V_{th}}.$$

gm in weak-inversion Equation 10

$$gm_{weak-inversion} = \frac{I_d}{nV_t}$$

$$n = 1.5 \text{ to } 2; V_t = \frac{kT}{q} \approx 26 \text{ mV}.$$

M3 serves as a current source for the differential-pair. The current of M3 is controlled by the ratio of its W/L with the W/L of M4. In the exemplary example, M3 is sized 1:1 to M4. Matching W/L determines how closely the tail current of the differential pair matches that of the reference current.

The optimal size of M3 can depend on two factors: (a) ability to match W/L and (b) the amount of drain current—which is the same as the reference current in the exemplary example. To match W/L, sizing L larger than minimum length improves matching because photolithographic variation generally has a smaller effect on larger lengths than the variation has on smaller ones.

Drain current as a function to W, L and Vgs Equation 11

$$I_d = -\frac{1}{2}\mu_p C_{ox} \frac{W}{L}(V_{gs} - V_{th})^2.$$

M3 has a fixed $I_d$ in the exemplary example. Since an $I_d$=10 µA is used in this example, per Equation 12, $V_{gs}$-$V_{th}$ is a very small value. To ensure M3's $I_d$ matches M4's reference $I_d$, $V_{gs}$ compensates for variances in Vth. To alleviate the amount $V_{gs}$ has to compensate, $I_d$ may be increased in some examples. Alternatively, small W/L factor may be utilized.

Vgs as a function of $I_d$ and $V_{th}$ Equation 12

$$V_{gs} = \sqrt{\left|-I_d \frac{L}{W}\frac{2}{\mu_p C_{ox}}\right|} + V_{th}$$

Figure 32B:
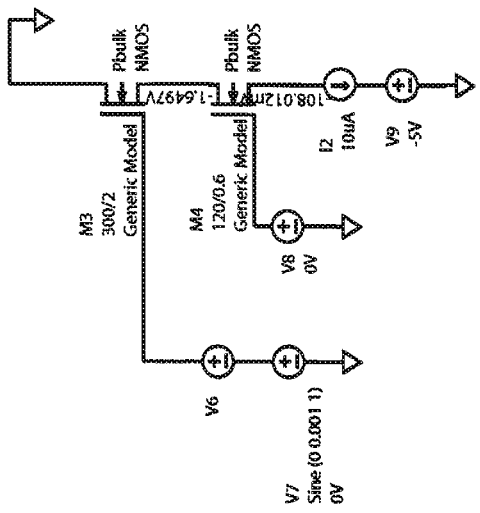
FIGS. 32A-32C shows schematics of the source follower plus pass-through transistor array designs, according to the principles herein.
Figure 32C:
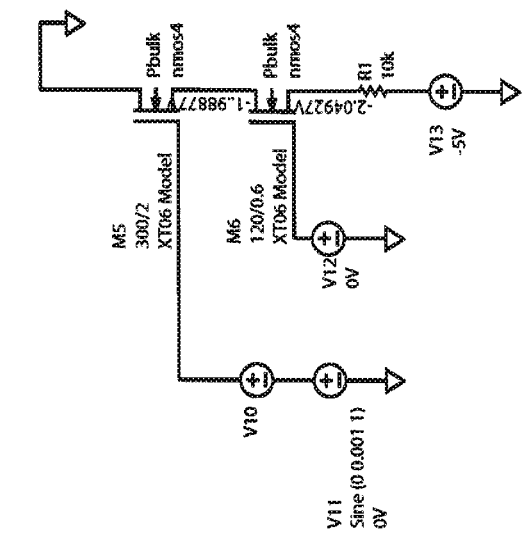
Figure 32A:
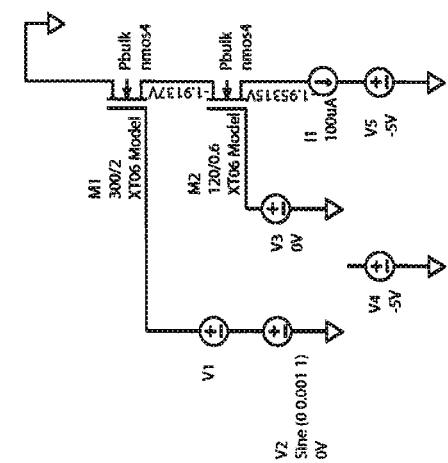

FIGS. 32A to 34 show example results of a simulation of an array based on source follower amplifiers and pass-through switches. FIGS. 32A-32C shows schematics of the source follower plus pass-through transistor array designs. FIG. 32A is the typical case, using XT06 models. FIG. 32B uses generic transistor models. FIG. 32C uses XT06 models with a passive load.

Figure 33:
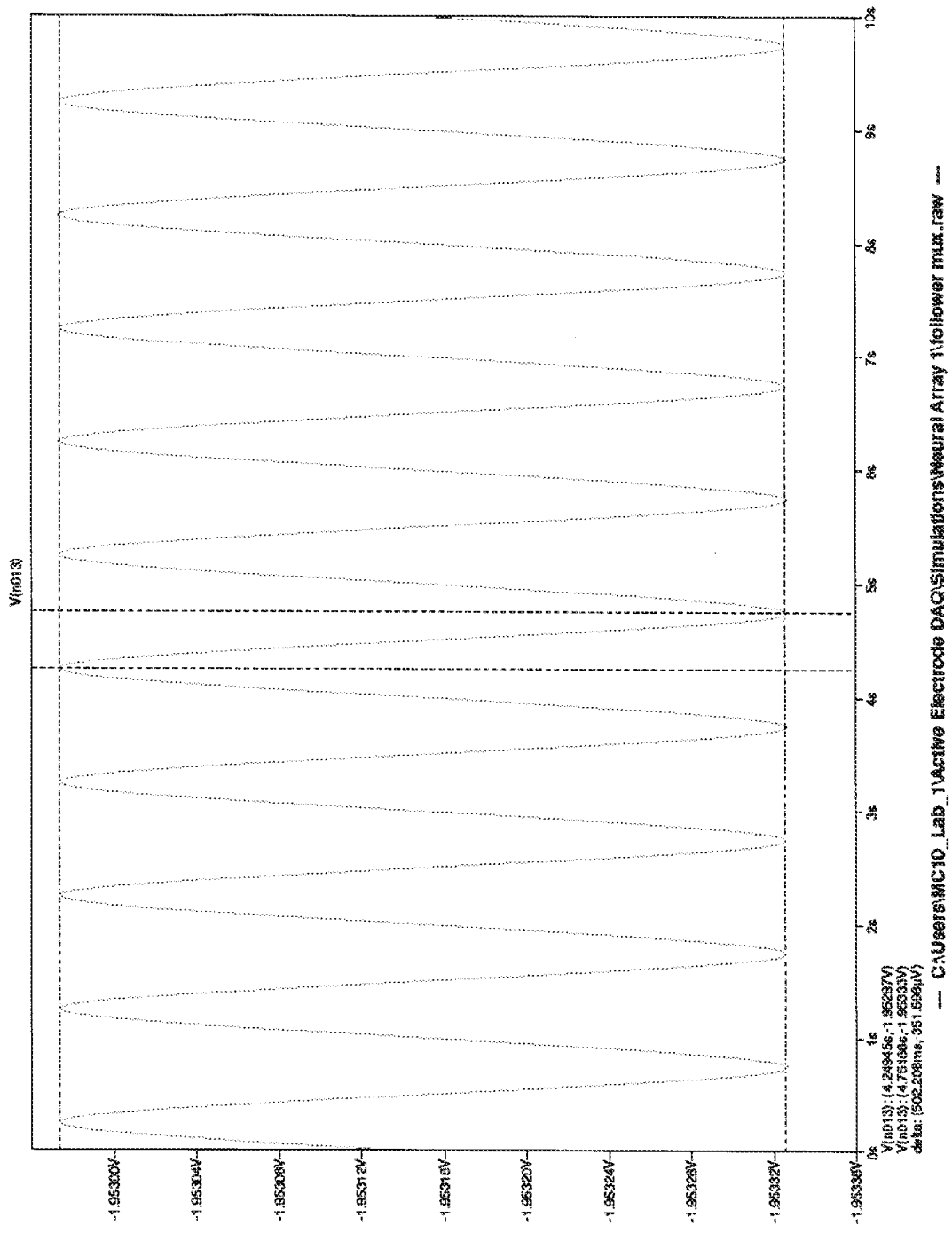
FIG. 33 shows an example output for the schematic of FIG. 32A, according to the principles herein.

FIG. 33 shows an example output for the schematic of FIG. 32A, taken between M2's source and active load (current source).

Figure 34:
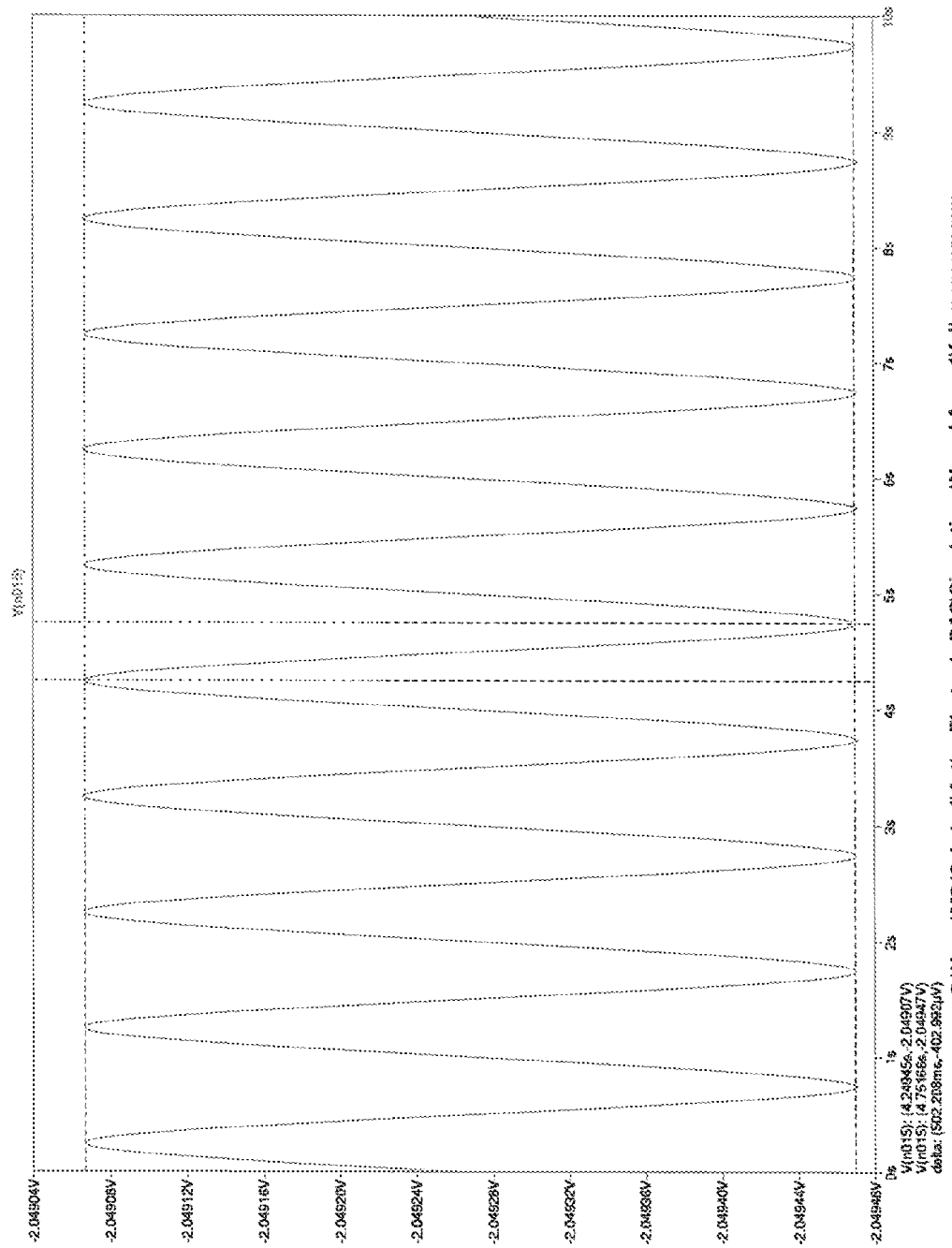
FIG. 34 shows example output for the schematic of FIG. 32C, according to the principles herein.

FIG. 34 shows output for the schematic of FIG. 32C, taken between M2's source and the passive load (resistor).

Figure 35:
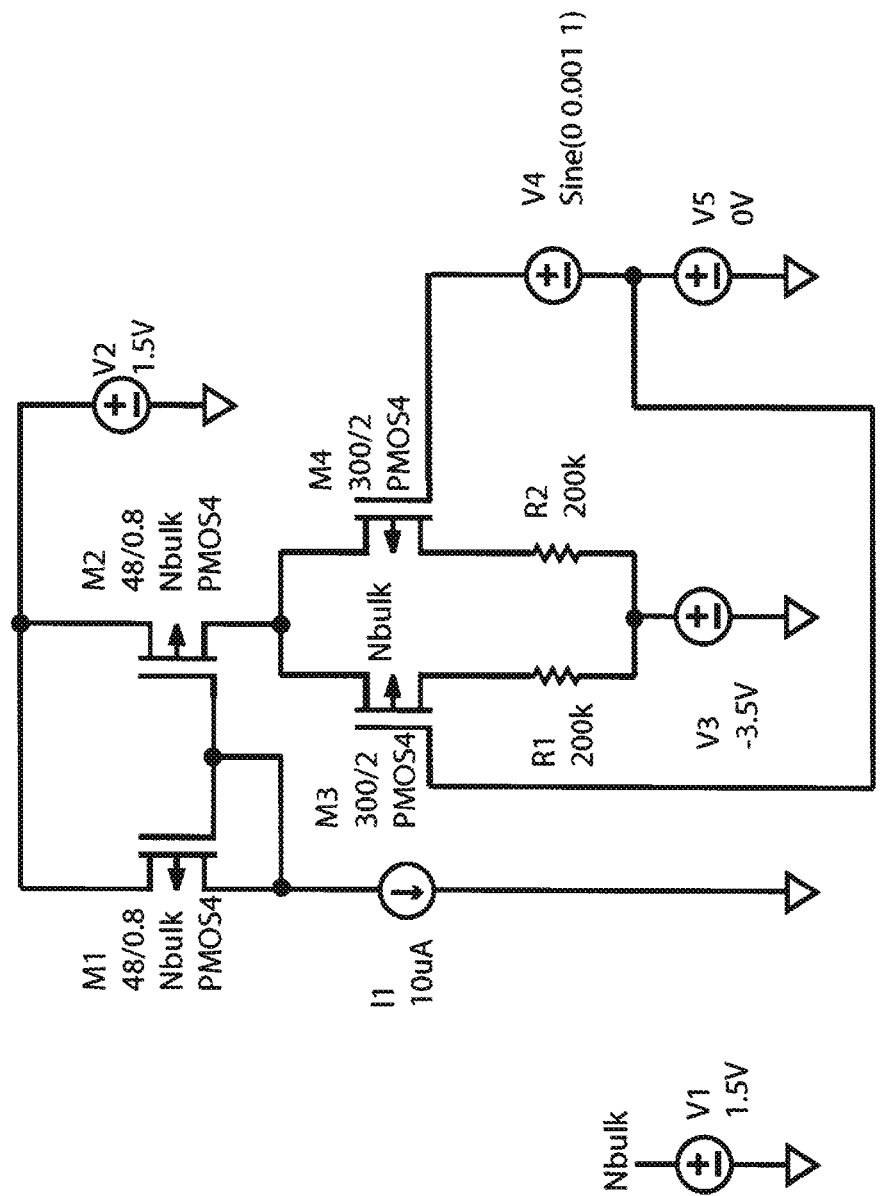
FIG. 35 shows an example single unit cell of a neural array, according to the principles herein.
Figure 36:
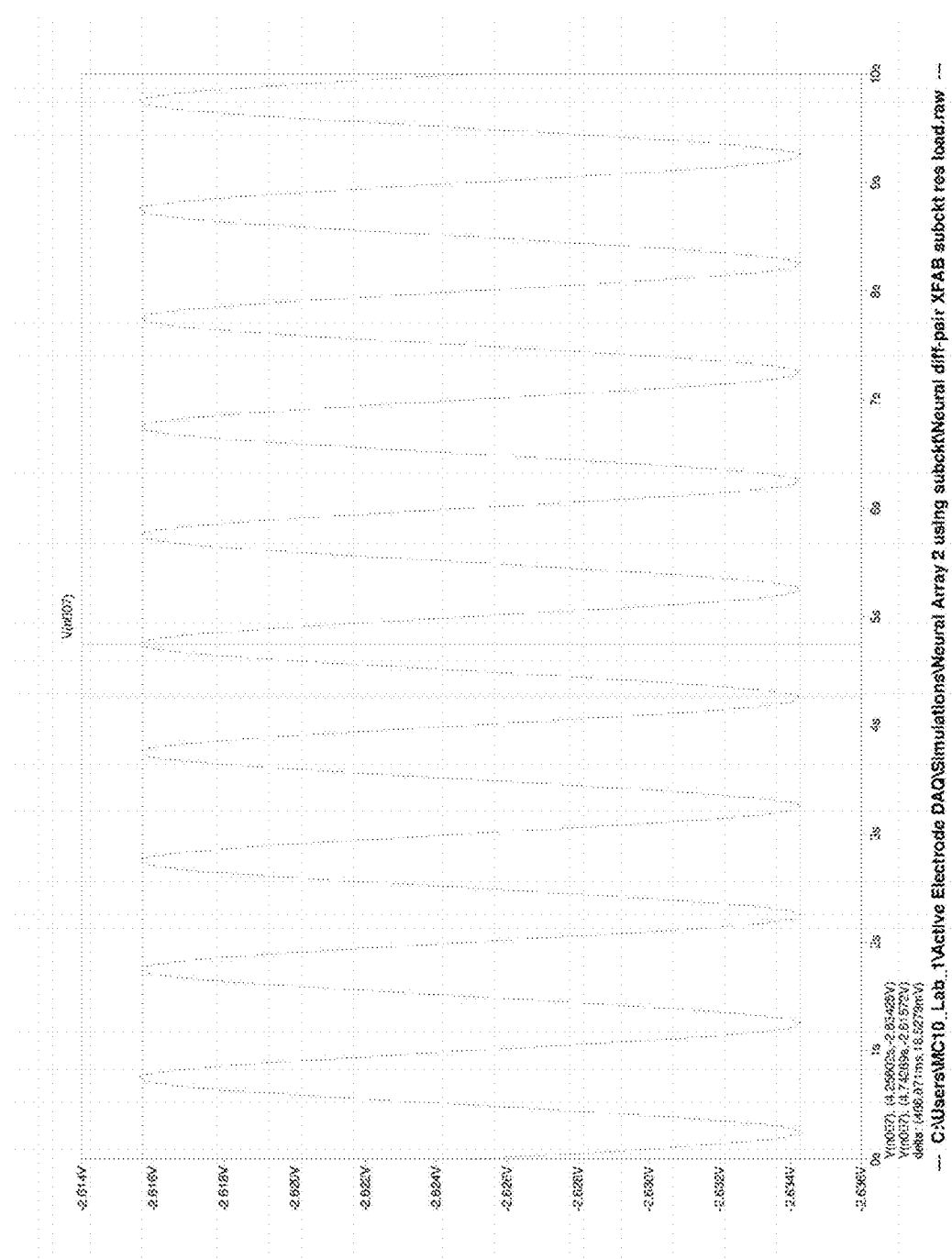
FIG. 36 shows an example output from the array of FIG. 35, according to the principles herein.

FIGS. 35 to 38 show example results of a simulation of an array based on differential-pair amplifiers. FIG. 35 shows a single unit cell of a neural array that includes M2, M3 and M4. FIG. 36 shows an output from the array of FIG. 35 with a gain of about 8.8.

Figure 37A:
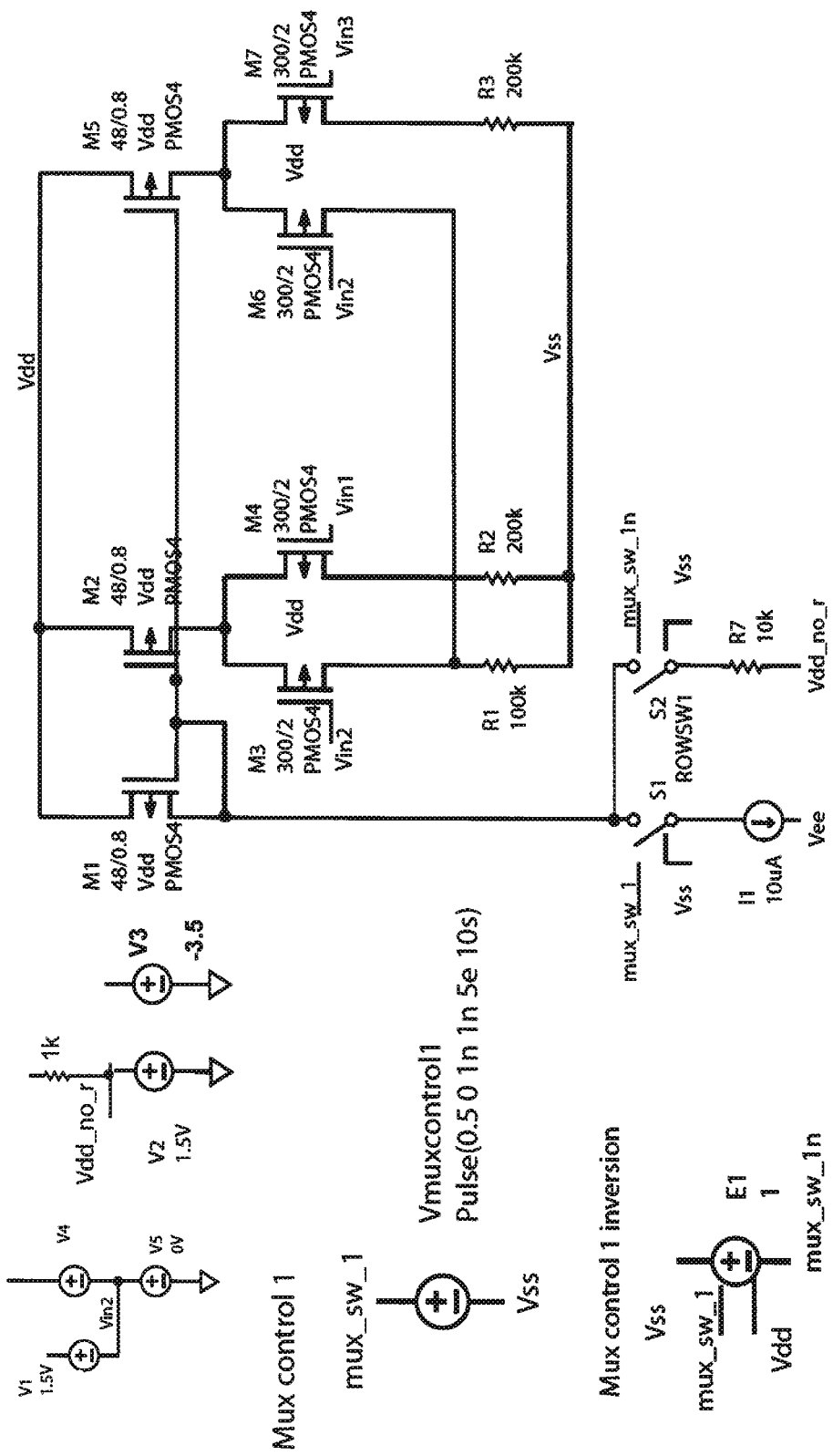
FIGS. 37A and 37B show an example schematic of a 2×2 circuit array, according to the principles herein.
Figure 37B:
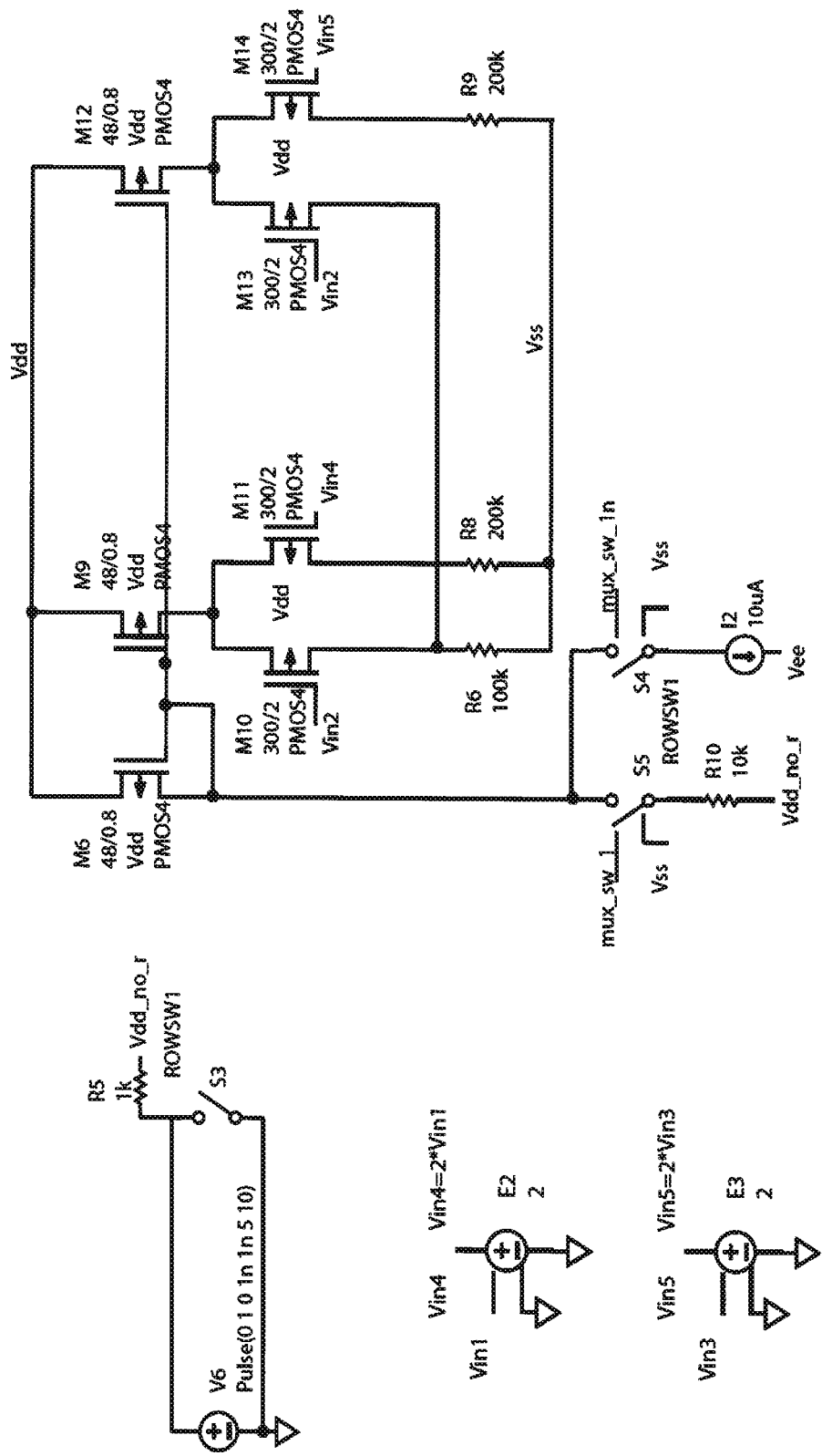

FIGS. 37A and 37B show a schematic of a 2×2 circuit array. Row 1 is ON initially. The inputs are 1 mV sine wave and square wave. Then Row 2 is turned ON. All the columns of a row are read simultaneously. The magnitude of Vin1 and Vin3 is 1 mV. The magnitude of Vin4 and Vin5 is 2 mV.

Figure 38:
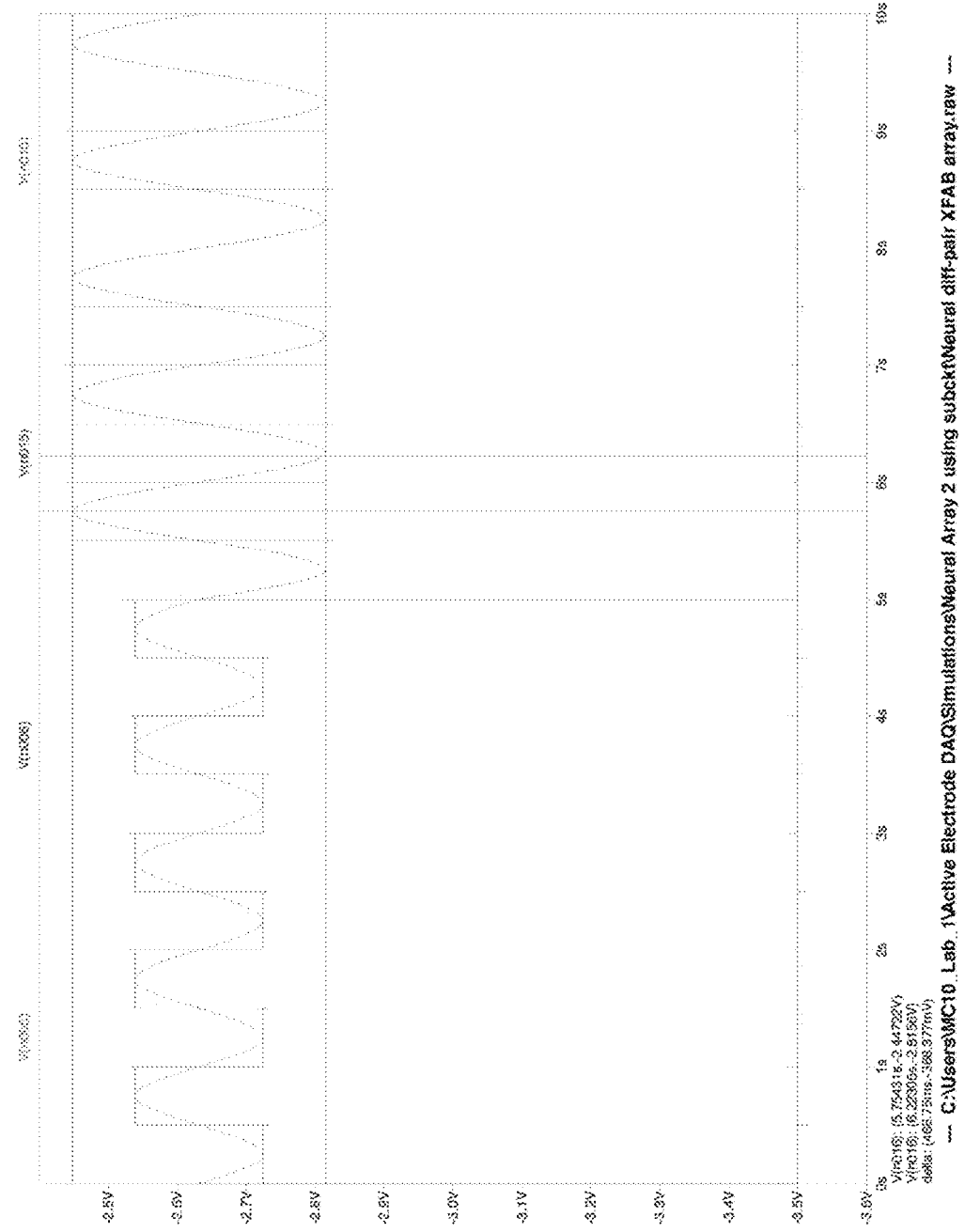
FIG. 38 shows an example output of the 2×2 array of FIGS. 37A and 37B, according to the principles herein.

FIG. 38 shows an output of the 2×2 array of FIGS. 37A and 37B. The outputs of row 1 are read simultaneously. Both the square wave and sine wave are read. At time=5 s, row 1 is deactivated and row 2 is activated. The signals from the second row are then read. The gain for this circuit is about 8.8.

Example Interfaces

Figure 39:
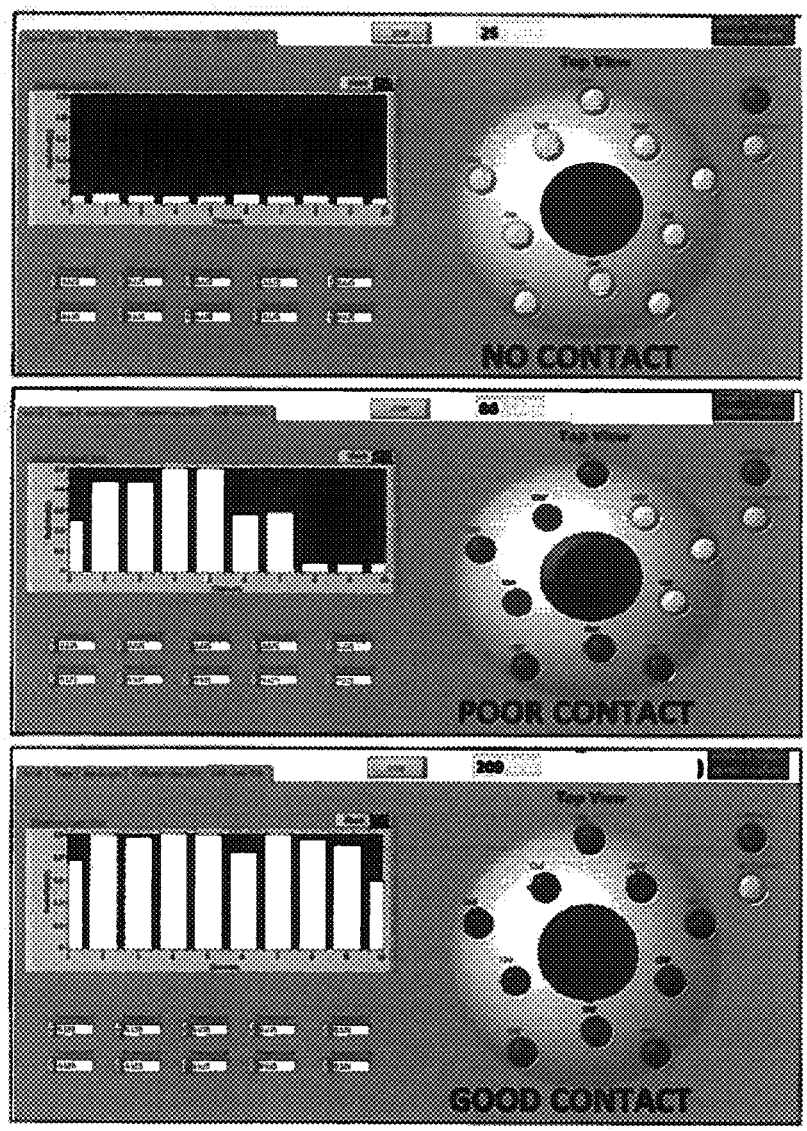
FIG. 39 provides an example series of screen shots of an example graphical user interface, according to the principles herein.

FIG. 39 provides a series of screen shots of an example graphical user interface demonstrating a variety of conditions simulated with an apparatus or system described herein. In this example, each circle in the user interface is used to indicate a state of contact or no contact between a sensing element and/or an active electrical circuit with a surface. Each circle can be configured to correspond to a single sensing element, or a specified group of sensing elements.

In the example of FIG. 39, each circle can be configured to provides a representation of a state of the sensing element (or group of sensing elements). In this example, an open circle on the display corresponds to no contact between a sensing element and the tissue, and the shaded circle indicates an amount of contact between a sensing element and the tissue. In another example, circles of a first color of the screenshots are used to indicate a first state (such as no contact), while circles of a second color are used to indicate a second state (such as contact above a certain threshold value).

In another example, the circles of the user interface can be used to indicate whether a specific sensing element in an array has made a measurement, such as a pressure, temperature, electrical property, or chemical measurement, that is above or below a threshold value.

The intermediate bus and/or flexible interconnection can be used to establish an electrical communication between the sensing elements and a data acquisition system.

In a non-limiting example, an impedance can be measured upon insertion and inflation of an inflatable body within a lumen to perform another operation, such as but not limited to, a cryoablation.

Use of an encapsulant according to the principles herein, in addition to reducing a chance of delamination of the apparatus from the flexible substrate, can reduced the thermal effects of having sensing elements and/or active electrical circuits on the balloon during cryoablation and minimized the effect of cryo-thermal cycling on performance of the sensing elements.

To establish a robust quantitative means of assessing a mapping operation, the changes in impedance measured during mapping can be assessed using an apparatus or system described herein and shown using the user interface. The results provide, for the first time, a new way to assess mapping while concurrently allowing the collection of new data on the behavior and successes of individual cryoballoon operators. The contact between a cryoballoon can be measured using impedance measurements.

Figure 40A:
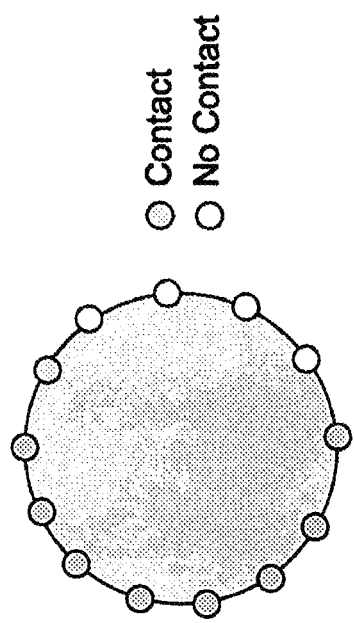
FIGS. 40A and 40B illustrate another example a visualization of measurements, according to the principles herein.
Figure 40B:
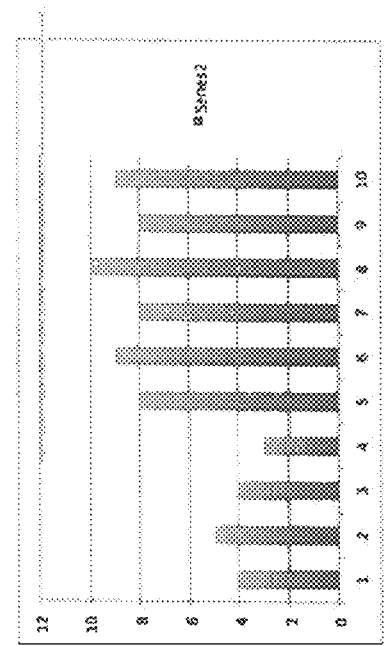

FIGS. 40A and 40B illustrate another example a visualization of sensing element and/or active electrical circuit measurements of a surface from measured data. Such visualization can help personnel in making assessments on the surface, such as its disease state. Through color or texture of the small circles representing each sensor (or specified group of sensors), the example user interface can be used to indicate whether a given measurement value is derived for a given sensing element and/or active electrical circuit. For example, a measured value of the sensing element and/or active electrical circuit above a threshold value can be decided as an indicator that the sensor has established contact with a portion of tissue, a measured value of the sensing element below the threshold value can be decided as an indicator that the sensor has not established contact with a portion of tissue. FIG. 40B is an example chart representation of a measure of contact force experienced by each sensor.

While the user interface of FIGS. 40A and 40B are described in terms of indication of contact force between the sensing elements and the surface, the user interface and visualization technique can be applied to display the results of other measurements, including impedance, temperature, pressure, or any other type of measurement that sensing elements according to the principles herein can be used to measure.

In an example, display of FIGS. 40A and 40B can be considered as a user interface displaying binary read outs of sensing elements and/or active electrical circuits disposed on a flexible substrate.

Figure 41:
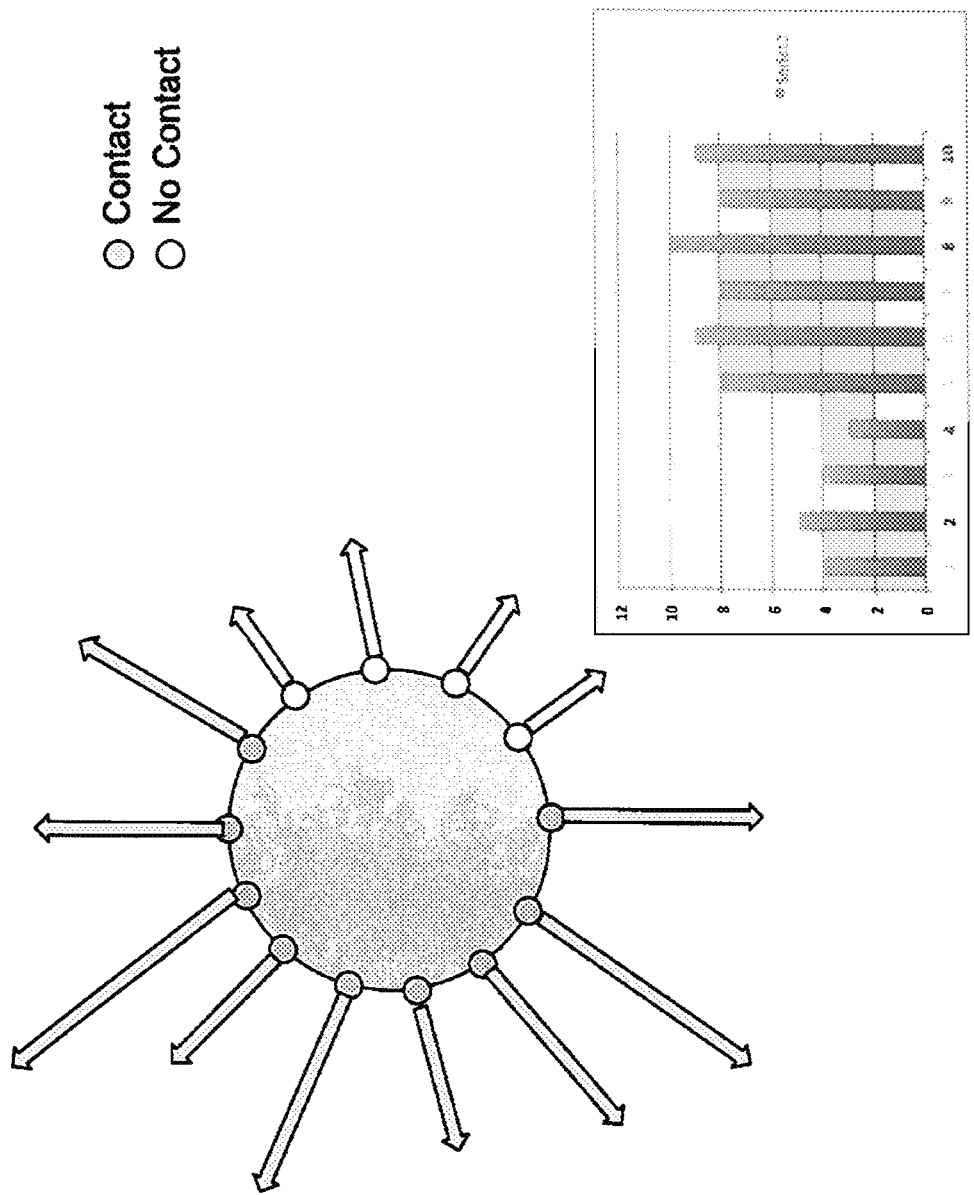
FIG. 41 demonstrates another example user interface, according to the principles herein.

FIG. 41 demonstrates another example user interface displaying quantitative read outs of sensing elements and/or active electrical circuits disposed on a flexible substrate. In this example, a length of an arrow at each sensing element and/or active electrical circuit element representation serves as an indicator of the amount of a measurement from the respective sensing element and/or active electrical circuit element.

CONCLUSION

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While various examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific examples described herein. It is, therefore, to be understood that the foregoing examples are presented by way of example only and that, within the scope of the appended claims and equivalents thereto, examples may be practiced otherwise than as specifically described and claimed. examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described examples can be implemented in any of numerous ways. For example, some examples may be implemented using hardware, software or a combination thereof. When any aspect of an example is implemented at least in part in software, the software code can be executed on any suitable processor or collection of processors, whether provided in a single computer or distributed among multiple computers.

In this respect, various aspects may be embodied at least in part as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium or non-transitory medium) encoded with one or more programs that, when executed on one or more computers or other processors, perform methods that implement the various examples of the technology described above. The computer readable medium or media can be transportable, such that the program or programs stored thereon can be loaded onto one or more different computers or other processors to implement various aspects of the present technology as described above.

The terms "program" or "software" are used herein in a generic sense to refer to any type of computer code or set of computer-executable instructions that can be employed to program a computer or other processor to implement various aspects of the present technology as described above. Additionally, it should be appreciated that according to one aspect of this example, one or more computer programs that when executed perform methods of the present technology need not reside on a single computer or processor, but may be distributed in a modular fashion amongst a number of different computers or processors to implement various aspects of the present technology.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various examples.

Also, the technology described herein may be embodied as a method, of which at least one example has been provided. The acts performed as part of the method may be ordered in any suitable way. Accordingly, examples may be constructed in which acts are performed in an order different than illustrated, which may include performing some acts simultaneously, even though shown as sequential acts in illustrative examples.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one example, to A only (optionally including elements other than B); in another example, to B only (optionally including elements other than A); in yet another example, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one example, to at least one, optionally including more than one, A, with no B present (and optionally including elements other than B); in another example, to at least one, optionally including more than one, B, with no A present (and optionally including elements other than A); in yet another example, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The claims should not be read as limited to the described order or elements unless stated to that effect. It should be understood that various changes in form and detail may be made by one of ordinary skill in the art without departing from the spirit and scope of the appended claims. All examples that come within the spirit and scope of the following claims and equivalents thereto are claimed.

The invention claimed is:

1. An apparatus for medical diagnosis and/or treatment, the apparatus comprising: a flexible substrate disposed on a catheter; a plurality of sensing elements disposed in a close-packed array; a first intermediate bus coupled to one or more sensing elements of the plurality of sensing elements disposed in a first quadrant of the flexible substrate; a second intermediate bus coupled to one or more sensing elements of the plurality of sensing elements disposed in a second quadrant of the flexible substrate, opposite the first quadrant; a third intermediate bus coupled to one or more sensing elements of the plurality of sensing elements disposed in a third quadrant of the flexible substrate; and a fourth intermediate bus coupled to one or more sensing elements of the plurality of sensing elements disposed in a fourth quadrant of the flexible substrate, opposite the third quadrant.

2. The apparatus of claim 1, wherein the sensing elements are disposed at areas of minimum bending and/or flexing of the flexible substrate.

3. The apparatus of claim 1, wherein a measurement of the plurality of sensing elements provides a measure of an amount of contact between the flexible substrate and a surface.

4. The apparatus of claim 3, wherein the surface is a portion of a tissue, and a measurement from the plurality of sensing elements provides an indication of an arrhythmia condition of the tissue.

5. The apparatus of claim 3, wherein the surface is a portion of a tissue, and a measurement from the plurality of sensing elements provides an indication of an atrial fibrillation or a ventricular fibrillation of the tissue.

6. The apparatus of claim 1, wherein the flexible substrate forms an inflatable body, and a portion of the first intermediate bus, the second intermediate bus, the third intermediate bus, and/or the fourth intermediate bus is disposed about a distal region of the inflatable body.

7. The apparatus of claim 6, wherein a measurement of the plurality of sensing elements provides a measure of an amount of contact between the inflatable body and a tissue.

8. The apparatus of claim 7, wherein the measurement of the plurality of sensing elements provides a mapping of the tissue.

9. The apparatus of claim 7, wherein the measurement of the plurality of sensing elements provides a spatial mapping and/or a temporal mapping of an arrhythmia.

10. An apparatus for medical diagnosis and/or treatment, the apparatus comprising: a flexible substrate forming an inflatable body and being disposed on a catheter; a plurality of sensing elements disposed on the flexible substrate proximate to a distal region of the inflatable body in an array; a first intermediate bus coupled to one or more sensing elements of the plurality of sensing elements disposed in a first quadrant of the inflatable body; a second intermediate bus coupled to one or more sensing elements of the plurality of sensing elements disposed in a second quadrant of the inflatable body, opposite the first quadrant; a third intermediate bus coupled to one or more sensing elements of the plurality of sensing elements disposed in a third quadrant of the inflatable body; and a fourth intermediate bus coupled to one or more sensing elements of the plurality of sensing elements disposed in a fourth quadrant of the inflatable body, opposite the third quadrant, wherein the third quadrant is oriented at substantially a 90° angle relative to the first quadrant, and a portion of the first intermediate bus, the second intermediate bus, the third intermediate bus, and/or the fourth intermediate bus is disposed about the distal region of the inflatable body.

11. The apparatus of claim 10, wherein the first intermediate bus, the second intermediate bus, the third intermediate bus, and the fourth intermediate bus are electrically conductive.

12. The apparatus of claim 11, wherein portions of the first intermediate bus, the second intermediate bus, the third intermediate bus, and the fourth intermediate bus are formed from a non-conductive material.

13. The apparatus of claim 10, further comprising at least one coupling structure disposed about the distal region of the inflatable body, wherein a portion of the first intermediate bus, the second intermediate bus, the third intermediate bus, and/or the fourth intermediate bus is coupled to a portion of the at least one coupling bus.

14. The apparatus of claim 13, wherein the coupling structure is a non-conductive structure.

15. The apparatus of claim 10, wherein the plurality of sensing elements are disposed in the array at an area of minimum curvature of the inflatable body proximate to the distal region of the inflatable body.

16. The apparatus of claim 10, wherein the first intermediate bus, the second intermediate bus, the third intermediate bus, and the fourth intermediate bus electronically connects the plurality of sensing elements with an electrical source.

17. The apparatus of claim 10, wherein the plurality of sensing elements are disposed in the array in the first, second, third, and fourth quadrants of the distal region of the inflatable body.

18. The apparatus of claim 10, wherein the first intermediate bus, the second intermediate bus, the third intermediate bus, and the fourth intermediate bus are collections of serpentine buses, and wherein the serpentine buses electrically couple to the plurality of sensing elements.

19. The apparatus of claim 10, further comprising an encapsulation material disposed over substantially a portion of the first intermediate bus, the second intermediate bus, the third intermediate bus, and/or the fourth intermediate bus and/or the plurality of sensing elements.

20. The apparatus of claim 19, wherein the encapsulation material comprises a polyurethane.

21. The apparatus of claim 10, wherein the plurality of sensing elements comprise at least one of a pressure sensor and/or at least one impedance sensor.

22. The apparatus of claim 10, wherein one or more of the sensing elements of the plurality of sensing elements comprises contact sensors.

23. The apparatus of claim 10, further comprising an encapsulation layer disposed over the plurality of sensing elements, wherein the encapsulation layer positions the sensing elements at a neutral mechanical plane.

24. The apparatus of claim 23, wherein the encapsulation layer comprises a polymer.

25. The apparatus of claim 10, wherein the inflatable body is disposed near a distal end of the catheter.

26. The apparatus of claim 25, wherein the catheter comprises a cryoablation device, a laser ablation device, a high intensity ultrasound, and/or a RF device.

27. The apparatus of claim 10, wherein the inflatable body is a balloon.

28. The apparatus of claim 27, wherein the balloon is cylindrical, onion-shaped, cone-shaped, dog-bone-shaped, barrel-shaped.

29. The apparatus of claim 10, wherein the sensing elements are formed from a conductive material.

30. The apparatus of claim 10, wherein the first intermediate bus, the second intermediate bus, the third intermediate bus, and the fourth intermediate bus are formed from a conductive material.

31. A system for mapping contact with a surface, the system comprising: an inflatable body having a distal portion and being disposed on a catheter; a plurality of sensing elements disposed on the inflatable body proximate to the distal portion; a first intermediate bus coupled to one or more sensing elements of the plurality of sensing elements disposed in a first quadrant of the inflatable body; a second intermediate bus coupled to one or more sensing elements of the plurality of sensing elements disposed in a second quadrant of the inflatable body, opposite the first quadrant; a third intermediate bus coupled to one or more sensing elements of the plurality of sensing elements disposed in a third quadrant of the inflatable body; a fourth intermediate bus coupled to one or more sensing elements of the plurality of sensing elements disposed in a fourth quadrant of the inflatable body, opposite the third quadrant; and an electronic display electrically coupled to the plurality of sensing elements, the electronic display providing a visual representation of the spatial orientation of the plurality of sensing elements on the inflatable body, the electronic display changing a visual attribute of an electrode in the plurality of sensing elements in response to a change in an electrical signal produced by the electrode, and the change in the electrical signal identifying a contact condition of the electrode with respect to the surface, wherein the third quadrant is oriented at substantially a 90° angle relative to the first quadrant, and a portion of the first intermediate bus, the second intermediate bus, the third intermediate bus, and/or the fourth intermediate bus is disposed about the distal portion of the inflatable body.

32. The apparatus of claim 31, wherein the visual attribute is a binary representation.

33. The apparatus of claim 31, wherein the visual attribute is a quantitative representation.

34. An apparatus for readout of one or more multiplexed signals, the apparatus comprising: a flexible substrate forming an inflatable body and being disposed on a catheter; a plurality of active electrical circuits disposed on the flexible substrate, the plurality of active electrical circuits configured to transmit one or more multiplexed signals to at least one signal processor, at least one active electrical circuit of the plurality of active electrical circuits comprising: at least one electrode; and at least one source-follower amplifier coupled to the at least one electrode; wherein the plurality of active electrical circuits are disposed in a distributed arrangement on the substrate such that the apparatus is conformable to a contour of a surface to be measured; a first conductive intermediate bus coupled to one or more active electrical circuits of the plurality of active electrical circuits disposed in a first quadrant of the inflatable body; a second conductive intermediate bus coupled to one or more active electrical circuits of the plurality of active electrical circuits disposed in a second quadrant of the inflatable body, opposite the first quadrant; a third conductive intermediate bus coupled to one or more active electrical circuits of the plurality of active electrical circuits disposed in a third quadrant of the inflatable body; and a fourth conductive intermediate bus coupled to one or more active electrical circuits of the plurality of active electrical circuits disposed in a fourth quadrant of the inflatable body, opposite the third quadrant, wherein the third quadrant is oriented at substantially a 90° angle relative to the first quadrant.

35. The apparatus of claim 34, wherein the plurality of active electrical circuits are disposed at areas of minimal curvature of the inflatable body in the distributed arrangement.

36. The apparatus of claim 34, wherein each active electrical circuit of the plurality of active electrical circuits is coupled to at least one adjacent active electrical circuit of the plurality of active electrical circuits via at least one conductive flexible interconnection.

37. The apparatus of claim 34, wherein each active electrical circuit of the plurality of active electrical includes at least one sensing element.

38. The apparatus of claim 37, wherein the plurality of active electrical circuits is configured to transmit one or more multiplexed signals to the at least one signal processor via the first conductive intermediate bus, the second conductive intermediate bus, the third conductive intermediate bus, and/or the fourth conductive intermediate bus.

39. The apparatus of claim 34, wherein the at least one active electrical circuit of the plurality of active electrical circuits further comprises at least one pass-through switch, and wherein the at least one source-follower amplifier is coupled to the at least one pass-through switch.

40. The apparatus of claim 34, wherein each of the active electrical circuit of the plurality of active electrical circuits comprises:
at least one electrode;
at least one source-follower amplifier coupled to the at least one electrode; and
at least one pass-through switch coupled to the at least one source-follower amplifier.

41. The apparatus of claim 40, wherein the at least one source-follower amplifier is an input transistor having a drain coupled to ground, and wherein the pass-through switch is a pass-through transistor coupled to the input transistor.

42. The apparatus of claim 41, wherein a source of the input transistor is coupled to a drain of the pass-through transistor.

43. The apparatus of claim 42, wherein a source of the pass-through transistor is coupled to the drain of that respective pass-through transistor, and wherein the respective at least one electrode of each active electrical circuit is coupled to a gate of the respective input transistor.

44. The apparatus of claim 42, wherein the input transistor is a NMOS transistor.

45. The apparatus of claim 42, wherein the pass-through transistor is a NMOS transistor.

46. The apparatus of claim 42, wherein the plurality of active electrical circuits are read in a row-column arrangement, and wherein each row-column element of the row-column arrangement corresponds to at least one active electrical circuit of the plurality of active electrical circuits.

47. The apparatus of claim 46, wherein the source of the pass-through transistor of each respective active electrical circuits is coupled to a column output of each respective row-column element.

48. The apparatus of claim 47, wherein all columns of the row-column arrangement are read substantially simultaneously, and wherein a single row of the row-column arrangement is active when the columns of the row-column arrangement are read.

49. The apparatus of claim 47, wherein the source of the pass-through transistor of at least two active electrical circuits are coupled to the column output of each respective row-column element.

50. The apparatus of claim 47, wherein each row input of the row-column arrangement is coupled to a gate of a pass-through transistor of each active electrical circuit of the plurality of active electrical circuits.

51. The apparatus of claim 47, wherein the voltage at the gate of the input transistor determines the voltage at the source of the input transistor.

* * * * *